(12) United States Patent
Ruben et al.

(10) Patent No.: US 7,012,134 B2
(45) Date of Patent: Mar. 14, 2006

(54) DENDRITIC ENRICHED SECRETED LYMPHOCYTE ACTIVATION MOLECULE

(75) Inventors: Steven M. Ruben, Olney, MD (US); Paul E. Young, Gaithersburg, MD (US)

(73) Assignee: Human Genome Sciences, Inc., Rockville, MD (US)

(*) Notice: Subject to any disclaimer, the term of this patent is extended or adjusted under 35 U.S.C. 154(b) by 459 days.

(21) Appl. No.: 10/062,523

(22) Filed: Feb. 5, 2002

(65) Prior Publication Data

US 2003/0022327 A1 Jan. 30, 2003

Related U.S. Application Data

(63) Continuation-in-part of application No. PCT/US00/21130, filed on Aug. 3, 2000, and a continuation-in-part of application No. 09/369,248, filed on Aug. 5, 1999, which is a continuation-in-part of application No. PCT/US99/02415, filed on Feb. 4, 1999, and a continuation-in-part of application No. 09/244,110, filed on Feb. 4, 1999.

(60) Provisional application No. 60/267,523, filed on Feb. 6, 2001, provisional application No. 60/190,062, filed on Mar. 17, 2000, provisional application No. 60/078,572, filed on Mar. 19, 1998, and provisional application No. 60/073,962, filed on Feb. 6, 1998.

(51) Int. Cl.
*C07K 16/18* (2006.01)
*C07K 16/24* (2006.01)
*A61K 39/395* (2006.01)

(52) U.S. Cl. ............... 530/387.9; 530/387.1; 530/387.7; 530/388.1; 530/388.15; 430/69.1; 430/320; 536/23.5

(58) Field of Classification Search ............ 530/387.9, 530/387.1, 387.3, 387.7, 388.1, 388.15; 430/69.1, 430/320; 536/23.5
See application file for complete search history.

(56) References Cited

U.S. PATENT DOCUMENTS 5,576,423 A    11/1996  Aversa et al.

FOREIGN PATENT DOCUMENTS

| WO | 94/01548 | 1/1994 |
|---|---|---|
| WO | 99/40184 | 8/1999 |
| WO | 00/18800 | 4/2000 |
| WO | 01/011046 A1 | 2/2001 |
| WO | 01/046260 A2 | 12/2001 |

OTHER PUBLICATIONS

U.S. patent application Ser. No. 09/912,292, Rosen et al.
U.S. patent application Ser. No. 09/912,293, Rosen et al.
Cocks et al., "A novel receptor involved in T-cell activation", Nature 376:260–263 (1995).
Ferrante et al. "Cytokine production and surface marker expression in acute and stable multiple sclerosis: altered IL–12 production and augmented signaling lymphocytic activation molecule (SLAM)–expressing lymphocytes in acute multiple sclerosis", J. Immunol. 160:1514–1521 (1998).
Kingsbury et al. "Cloning, expression, and function of BLAME, a novel member of the CD2 family" J. Immunol. 166:5675–5680 (2001).
Punnonen et al. "Soluble and membrane–bound forms of signaling lymphocytic activation molecules (SLAM) induce proliferation and Ig synthesis by activated human B lymphocytes" J. Exp. Med. 185(6):993–1004 (1997).
GenBank Accession No. N62522, Hiller et al. (Mar. 1, 1996).
GenBank Accession No. AF144235, Zhang et al., (Jun. 1, 1999).
GenBank Accession No. AA627522, Strausberg et al. (Oct. 31, 1997).
GenBank Accession No. AA320408, Adams et al. (Apr. 19, 1997).
GenBank Accession No. R11635, Hillier et al., (Apr. 11, 1995).
GenBank Accession No. AA379112, Adams et al. (Apr. 21, 1997).
GenBank Accession No. R09841, Hiller et al. (Apr. 6, 1995).
GenBank Accession No. Z20320 (Feb. 7, 1995).
GenBank Accession No. N79421, Hillier et al. (Apr. 2, 1996).
GenBank Accession No. D45800, Itoh et al. (Feb. 20, 1995).
GenBank Accession No. AA917335, Strausberg et al. (Jun. 24, 1998).
GenBank Accession No. AI094818, Strausberg et al., (Oct. 1, 1998).
GenBank Accession No. G22227, Hudson et al. (May 31, 1996).
GenBank Accession No. NP_064510, Kingsbury et al., (Sep. 6, 2003).
GenBank Accession No. NM_020125, Kingsbury et al., (Sep. 6, 2003).
Genseq Accession No. Q76829, Gross et al. (1994).
Database Genbank Nucleotide (P.R. China), Accession No. AF4146761, "Novel human cell membrane protein" (Zhang et al.), May 4, 2000.
International Search Report, Application No. PCT/US02/03227, mailed Oct. 15, 2003.

*Primary Examiner*—Gary Kunz
*Assistant Examiner*—Fozia Hamud
(74) *Attorney, Agent, or Firm*—Human Genome Sciences, Inc.

(57) ABSTRACT

The present invention relates to a novel human protein called Dendritic Enriched Secreted Lymphocyte Activation Molecule, and isolated polynucleotides encoding this protein. Also provided are vectors, host cells, antibodies, and recombinant methods for producing this human protein. The invention further relates to diagnostic and therapeutic methods useful for diagnosing and treating disorders related to this novel human protein.

93 Claims, 6 Drawing Sheets

```
  1 GAAGGACCACAGCTCCTCCCGTGCATCCACTCGGCCTGGGAGGTTCTGGATTTTGGCTGT 60

61 CGAGGGAGTTTGCCTGCCTCTCCAGAGAAAGATGGTCATGAGGCCCCTGTGGAGTCTGCT 120
  1                                   M   V   M   R   P   L   W   S   L   L   10

121 TCTCTGGGAAGCCCTACTTCCCATTACAGTTACTGGTGCCCAAGTGCTGAGCAAAGTCGG 180
 10  L   W   E   A   L   L   P   I   T   V   T   G   A   Q   V   L   S   K   V   G   30

181 GGGCTCGGTGCTGCTGGTGGCAGCGCGTCCCCCTGGCTTCCAAGTCCGTGAGGCTATCTG 240
 30  G   S   V   L   L   V   A   A   R   P   P   G   F   Q   V   R   E   A   I   W   50

241 GCGATCTCTCTGGCCTTCAGAAGAGCTCCTGGCCACGTTTTTCCGAGGCTCCCTGGAGAC 300
 50  R   S   L   W   P   S   E   E   L   L   A   T   F   F   R   G   S   L   E   T   70

301 TCTGTACCATTCCCGCTTCCTGGGCCGAGCCCAGCTACACAGCAACCTCAGCCTGGAGCT 360
 70  L   Y   H   S   R   F   L   G   R   A   Q   L   H   S   N   L   S   L   E   L   90

361 CGGGCCGCTGCAGTCTGGAGACAGCGGCAACTTCTCCGTGTTCATGGTGGACACAAGGGG 420
 90  G   P   L   E   S   G   D   S   G   N   F   S   V   L   M   V   D   T   R   G   110

421 CCAGCCCTGGACCCAGACCCTCCAGCTCAAGGTGTACGATGCAGTGCCCAGGCCCGTGGT 480
110  Q   P   W   T   Q   T   L   Q   L   K   V   Y   D   A   V   P   R   P   V   V   130

481 ACAAGTGTTCATTGCTGTAGAAAGGGATGCTCAGCCCTCCAAGACCTGCCAGGTTTTCTT 540
130  Q   V   F   I   A   V   E   R   D   A   Q   P   S   K   T   C   Q   V   F   L   150

541 GTCCTGTTGGGCCCCCAACATCAGCGAAATAACCTATAGCTGGCGACGGGAGACAACCAT 600
150  S   C   W   A   P   N   I   S   E   I   T   Y   S   W   R   R   E   T   T   M   170

601 GGACTTTGGTATGGAACCACACAGCCTCTTCACAGACGGACAGGTGCTGAGCATTTCCCT 660
170  D   F   G   M   E   P   H   S   L   F   T   D   G   Q   V   L   S   I   S   L   190

661 GGGACCAGGAGACAGAGATGTGGCCTATTCCTGCATTGTCTCCAACCCTGTCAGCTGGGA 720
190  G   P   G   D   R   D   V   A   Y   S   C   I   V   S   N   P   V   S   W   D   210

721 CTTGGCCACAGTCACGCCCTGGGATAGCTGTCATCATGAGGCAGCACCAGGGAAGGCCTC 780
210  L   A   T   V   T   P   W   D   S   C   H   H   E   A   A   P   G   K   A   S   230

781 CTACAAAGATGTGCTGCTGGTGGTGGTGCCTGTCTCGCTGCTCCTGATGCTGGTTACTCT 840
230  Y   K   D   V   L   L   V   V   V   P   V   S   L   L   L   M   L   V   T   L   250
```

FIG. 1A

```
841 CTTCTCTGCCTGGCACTGGTGCCCCTGCTCAGGGAAAAAGAAAAAGGATGTCCATGCTGA 900
250  F  S  A  W  H  W  C  P  C  S  G  K  K  K  D  V  H  A  D   270

901 CAGAGTGGGTCCAGAGACAGAGAACCCCCTTGTGCAGGATCTGCCATAAAGGACAATATG 960
270  R  V  G  P  E  T  E  N  P  L  V  Q  D  L  P  *             285

961 AACTGATGCCTGGACTATCAGTAACCCCACTGCACAGGCACACGATGCTCTGGGACATAA 1020

1021 CTGGTGCCTGGAAATCACCATGGTCCTCATATCTCCCATGGGAATCCTGTCCTGCCTCGA 1080

1081 AGGAGCAGCCTGGGCAGCCATCACACCACGAGGACAGGAAGCACCAGCACGTTTCACACC 1140

1141 TCCCCCTTCCCTCTCCCATCTTCTCATATCCTGGCTCTTCTCTGGGCAAGATGAGCCAAG 1200

1201 CAGAACATTCCATCCAGGACACTGGAAGTTCTCCAGGATCCAGATCCATGGGACATTAA 1260

1261 TAGTCCAAGGCATTCCCTCCCCCACCACTATTCATAAAGTATTAACCAACTGGCACCAAG 1320

1321 GAATTGCCTCCAGCCTGAGTCCTAGGCTCTAAAAGATATTACATATTTGAACTAATAGAG 1380

1381 GAACTCTGAGTCACCCATGCCAGCATCAGCTTCAGCCCCAGACCCTGCAGTTTGAGATCT 1440

1441 GATGCTTCCTGAGGGCCAAGGCATTGCTGTAAGAAAAGGTCTAGAAATAGGTGAAAGTGA 1500

1501 GAGGTGGGGGACAGGGGTTTCTCTTTCTGGCCTAAGGACTTTCAGGTAATCAGAGTTCAT 1560

1561 GGGCCCTCAAAGGTAAATTGCAGTTGTAGACACCGAGGATGGTTGACAACCCATGGTTGA 1620

1621 GATGGGCACCGTTTTGCAGGAAACACCATATTAATAGACATCCTCACCATCTCCATCCGC 1680

1681 TCTCACGCCTCCTGCAGGATCTGGGAGTGAGGGTGGAGAGTCTTTCCTCACGCTCCAGCA 1740

1741 CAGTGGCCAGGAAAAGAAATACTGAATTTGCCCCAGCCAACAGGACGTTCTTGCACAACT 1800

1801 TCAAGAAAAGCAGCTCAGCTCAGGATGAGTCTTCCTGCCTGAAACTGAGAGAGTGAAGAA 1860

1861 CCATAAAACGCTATGCAGAAGGAACATTATGGAGAGAAAGGGTACTGAGGCACTCTAGAA 1920
```

FIG. 1B

```
1921 TCTGCCACATTCATTTTCAAATGCAAATGCAGAAGACTTACCTTAGTTCAAGGGGAGGGG 1980

1981 ACAAAGACCCCACAGCCCAACAGCAGGACTGTAGAGGTCACTCTGACTCCATCAAACTTT 2040

2041 TTATTGTGGCCATCTTAGGAAAATACATTCTGCCCCTGAATGATTCTGTCTAGAAAAGCT 2100

2101 CTGGAGTATTGATCACTACTGGAAAAACACTTAAGGAGCTAAACTTACCTTCGGGGATTA 2160

2161 TTAGCTGATAAGGTTCACAGTTTCTCTCACCCAGGTGTAACTGGATTTTTTCTGGGGCCT 2220

2221 CAATCCAGTCTTGATAACAGCGAGGAAAGAGGTATTGAAGAAACAGGGGTGGGTTTGAAG 2280

2281 TACTATTTTCCCCAGGGTGGCTTCAATCTCCCCACCTAGGATGTCAGCCCTGTCCAAGGA 2340

2341 CCTTCCCTCTTCTCCCCCAGTTCCCTGGGCAATCACTTCACCTTGGACAAAGGATCAGCA 2400

2401 CAGCTGGCCTCCAGATCCACATCACCACTCTTCCACTCGATTGTTCCCAGATCCTCCCTG 2460

2461 CCTGGCCTGCTCAGAGGTTCCCTGTTGGTAACCTGGCTTTATCAAATTCTCATCCCTTTC 2520

2521 CCACACCCACTTCTCTCCTATCACCTTCCCCCAAGATTACCTGAACAGGGTCCATGGCCA 2580

2581 CTCAACCTGTCAGCTTGCACCATCCCCACCTGCCACCTACAGTCAGGCCACATGCCTGGT 2640

2641 CACTGAATCATGCAAAACTGGCCTCAGTCCCTAAAAATGATGTGGAAAGGAAAGCCCAGG 2700

2701 ATCTGACAATGAGCCCTGGTGGATTTGTGGGGAAAAAATACACAGCACTCCCCACCTTTC 2760

2761 TTTCGTTCATCTCCAGGGCCCCACCTCAGATCAAAGCAGCTCTGGATGAGATGGGACCTG 2820

2821 CAGCTCTCCCTCCACAAGGTGACTCTTAGCAACCTCATTTCGACAGTGGTTTGTAGCGTG 2880

2881 GTGCACCAGGGCCTTGTTGAACAGATCCACACTGCTCTAATAAAGTTCCCATCCTTAATG 2940

2941 ACTCACTTGTCAACTAGTGGACTAATTAACCCTCCACCAAAAAAACACAAAGTGCTTCTG 3000

3001 TGAGACCAATTTTGTGCTAATGAGCATTGAGACTGATGCTTTGTAAGTCACACCACAACA 3060
```

FIG. 1C

```
3061 AATATTCATTGAGGGCGCTGCATGTCCTGGGTACATTTCTTGGCACTTGGGAATCAGTAG 3120

3121 TCAAGCGAAACCCTTGCCTTTGAGAGTTTATGGTCTGGATAATATAAATAAACAAGTAAG 3180

3181 CATAAAAAAAAAAAAAAAAAAAAAAAAAAAAAAAAAAAAA 3220
```

FIG. 1D

```
                    10               20               30               40
  1  M V M R P L W S L - - - - L L W E A L P I T V T G A Q - - - - - - - V L S K V G   HDPJP39.AA
  1  M D P K G L L S L T F V L F L S L A F G A S Y G T G G R M M N C P K I L R Q L G   gi/984969

50               60               70               80
 31  G S V L L V A A R P P G F Q - V R E A I W R S L W P S E E L - - - L A T F F R G   HDPJP39.AA
 41  S K V L L - - - - P L T Y E R I N K S M N K S I H L V V T M A K S L E N S V E N   gi/984969

90              100              110              120
 67  S L E T L Y H S - - - - - R F L G - R A Q L H - S N L S L E L G P L E S G D S G   HDPJP39.AA
 77  K I V S L D P S E A G P P R Y L G D R Y K F Y L E N L T L G I R E S R K E D E G   gi/984969

130              140              150              160
100  N F S V L M V D T R G Q P W T Q T L Q L K V Y D A V P R P V V Q F I A V E R D     HDPJP39.AA
117  W Y - L M T L E K N V S V Q R F C L Q L R I Y F Q V S T P E L K V L - - - - N K   gi/984969

170              180              190              200
140  A Q P S K T C Q V F L S C W A P N I S E I T Y S W R R E T T M D F G M E P H S L   HDPJP39.AA
152  T Q E N G T C T L I L G C T V E K G D H V A Y S W S E K A - - - - G T H P L N P   gi/984969

210              220              230              240
180  F T D G Q V L S I S L G P G D R D V A Y S C I V S N P V S W D L A T V T P W D S   HDPJP39.AA
188  A N S S H L L S L T L G P Q H A D N L I Y I C T V S N P I S N N S Q T F S P W P G   gi/984969

250              260              270              280
220  C H H E A P G K - - A S Y K D V L V V P V S L L L M L V T L F S - - - A W         HDPJP39.AA
228  C R T D P S E T K P W A V Y A G L L G G V I M I L I M V V I L Q L R R R G K T N   gi/984969

290              300              310              320
255  H W C P C S G K K K K D V - - H A D R V G P - - - - - - - - - - - - - - - -       HDPJP39.AA
268  H Y Q T T V E K K S L T L Y A Q V Q K P G P L Q K K L D S F P A Q D P C T T I Y   gi/984969

330              340
275  - E T E N P L V Q D L P .                                                         HDPJP39.AA
308  V A A T E P V P E S V Q E T N S I T V Y A S V T L P E S                           gi/984969
```

FIG. 2

DENDRITIC ENRICHED SECRETED LYMPHOCYTE ACTIVATION MOLECULE

CROSS REFERENCE TO RELATED APPLICATIONS

This application claims benefit of 35 U.S.C. §119(e) based on U.S. Provisional Application Ser. No. 60/267,523, filed Feb. 6, 2001 and is a continuation-in-part of, and claims priority under 35 U.S.C. §120 to International Patent Application No: PCT/US00/21130, filed Aug. 3, 2000, which claims benefit under 35 U.S.C. §119(e) of U.S. Provisional Application No. 60/190,062, filed Mar. 17, 2000 and which is a continuation-in-part of, and claims priority under 35 U.S.C. §120 to U.S. application Ser. No. 09/369,248, filed Aug. 5, 1999, which is a continuation-in-part of, and claims priority under 35 U.S.C. §120 to International Patent Application No:PCT/US99/02415, filed Feb. 4, 1999 and of U.S. application Ser. No. 09/244,110 filed Feb. 4, 1999, which claims benefit of 35 U.S.C. §119(e) based on U.S. Provisional Application Ser. Nos. 60/073,962, filed Feb. 6, 1998, and 60/078,572, filed Mar. 19, 1998. Each of the above referenced applications is hereby incorporated by reference herein in its entirety.

FIELD OF THE INVENTION

The present invention relates to a novel human gene encoding a polypeptide which is a member of the Secreted Lymphocyte Activation Molecule (SLAM) family. More specifically, the present invention relates to a polynucleotide encoding a novel human polypeptide named Dendritic Enriched Secreted Lymphocyte Activation Molecule, or "D-SLAM." This invention also relates to D-SLAM polypeptides, as well as vectors, host cells, antibodies directed to D-SLAM polypeptides, and the recombinant methods for producing the same. Also provided are diagnostic methods for detecting disorders related to the immune system, and therapeutic methods for treating, diagnosing, detecting, and/or preventing such disorders. The invention further relates to screening methods for identifying agonists and antagonists of D-SLAM activity.

BACKGROUND OF THE INVENTION

A member of the immunoglobulin gene superfamily, SLAM is rapidly induced after activation of naive T- and B-cells. (Cocks, B. G., "A Novel Receptor Involved in T-Cell Activation," Nature 376:260–263 (1995); Aversa, G., "Engagement of the Signaling Lymphocytic Activation Molecule (SLAM) on Activated T Cells Results in Il-2-Independent, Cyclosporin A-Sensitive T Cell Proliferation and IFN-gamma Production," J. Immun. 4036–4044 (1997).) A multifunctional 70 kDa glycoprotein, SLAM causes proliferation and differentiation of immune cells. (Punnonen, J., "Soluble and Membrane-bound Forms of Signaling Lymphocytic Activation Molecule (SLAM) Induce Proliferation and Ig Synthesis by Activated Human B Lymphocytes," J. Exp. Med. 185:993–1004 (1997).) To elicit an immune response, both a secreted form of SLAM, as well as a membrane bound SLAM, are thought to interact.

It is also known that dendritic cells (DC) are the principal antigen presenting cells involved in primary immune responses; their major function is to obtain antigen in tissues, migrate to lymphoid organs, and activate T cells. (Mohamadzadeh, M. et al., J. Immunol. 156: 3102–3106 (1996).) In fact, DC are usually the first immune cells to arrive at sites of inflammation on mucous membranes. (See, e.g., Weissman, D. et al., J. Immunol. 155:4111–4117 (1995).) DC are also known to directly interact with B cells. There is a constant need to identify new polypeptide factors which may mediate interactions between DC and T cells and/or B cells, leading to the activation and/or proliferation of immune cells. To date, however, SLAM molecules have not been identified on DC cells.

Thus, there is a need for polypeptides that affect the proliferation, activation, survival, and/or differentiation of immune cells, such as T- and B-cells, since disturbances of such regulation may be involved in disorders relating to immune system. Therefore, there is a need for identification and characterization of such human polypeptides which can play a role in detecting, preventing, ameliorating or correcting such disorders.

SUMMARY OF THE INVENTION

The present invention relates to a novel polynucleotide and the encoded polypeptide of D-SLAM. Moreover, the present invention relates to vectors, host cells, antibodies, and recombinant methods for producing the polypeptides and polynucleotides. Also provided are diagnostic methods for detecting and/or diagnosing disorders relates to the polypeptides, and therapeutic methods for treating and/or preventing such disorders. The invention further relates to screening methods for identifying binding partners of D-SLAM.

In accordance with one embodiment of the present invention, there is provided a novel mature D-SLAM polypeptide, as well as biologically active and diagnostically or therapeutically useful fragments, analogs and derivatives thereof.

In a preferred embodiment, the invention provides for D-SLAM polypeptides and/or polynucleotides (including, but not limited to, fragments and/or variants thereof), and/or agonists thereof, which can be used, for example, to inhibit B-cell proliferation.

In a further preferred embodiment, the invention provides for D-SLAM polypeptides (including, but not limited to, soluble forms of D-SLAM) and/or D-SLAM antagonists, which can be used, for example, to enhance B-cell proliferation.

In accordance with another embodiment of the present invention, there are provided isolated nucleic acid molecules encoding human D-SLAM, including mRNAs, DNAs, cDNAs, genomic DNAs as well as analogs and biologically active and diagnostically or therapeutically useful fragments and derivatives thereof.

The present invention provides isolated nucleic acid molecules comprising, or alternatively, consisting of, a polynucleotide encoding a cytokine that are structurally similar to Secreted Lymphocyte Activation Molecules (SLAM) and related cytokines and have similar biological effects and activities. This cytokine is named D-SLAM and the invention includes D-SLAM polypeptides having at least a portion of the amino acid sequence in FIGS. 1A, 1B, 1C, and 1D (SEQ ID NO:2) or amino acid sequence encoded by the cDNA clone (HDPJO39) deposited on Feb. 6, 1998 assigned ATCC number 209623. The nucleotide sequence determined by sequencing the deposited D-SLAM clone, which is shown in FIGS. 1A, 1B, 1C, and 1D (SEQ ID NO:1), contains an open reading frame encoding a complete polypeptide of 285 amino acid residues including an N-terminal methionine (i.e., amino acid residues 1–285 of SEQ ID NO:2), a predicted signal peptide of about 22 amino acid residues (i.e., amino acid residues 1–22 of SEQ ID NO:2), a predicted mature form of about 263 amino acids (i.e., amino acid residues 23–285 of SEQ ID NO:2), and a deduced molecular weight for the complete protein of about 34.2 kDa.

Thus, one embodiment of the invention provides an isolated nucleic acid molecule comprising, or alternatively consisting of, a polynucleotide having a nucleotide sequence selected from the group consisting of: (a) a nucleotide sequence encoding a full-length D-SLAM polypeptide having the complete amino acid sequence in FIGS. 1A, 1B, 1C, and 1D (SEQ ID NO:2) or as encoded by the cDNA clone contained in the deposit having ATCC accession number 209623; (b) a nucleotide sequence encoding the predicted extracellular domain of the D-SLAM polypeptide having the amino acid sequence at positions 23 to 232 in FIGS. 1A, 1B, 1C, and 1D (SEQ ID NO:2) or as encoded by the clone contained in the deposit having ATCC accession number 209623; (c) a nucleotide sequence encoding a fragment of the polypeptide of (b) having D-SLAM functional activity (e.g., biological acitivity); (d) a nucleotide sequence encoding a polypeptide comprising the D-SLAM intracellular domain (predicted to constitute amino acid residues from about 256 to about 285 in FIGS. 1A, 1B, 1C, and 1D (SEQ ID NO:2)) or as encoded by the clone contained in the deposit having ATCC accession number 209623; (e) a nucleotide sequence encoding a polypeptide comprising the D-SLAM transmembrane domain (predicted to constitute amino acid residues from about 233 to about 255 in FIGS. 1A, 1B, 1C, and 1D (SEQ ID NO:2) or as encoded by the cDNA clone contained in the deposit having ATCC accession number 209623; (f) a nucleotide sequence encoding a soluble D-SLAM polypeptide having the extracellular and intracellular domains but lacking the transmembrane domain; and (g) a nucleotide sequence complementary to any of the nucleotide sequences in (a), (b), (c), (d), (e) or (f) above.

Further embodiments of the invention include isolated nucleic acid molecules that comprise, or alternatively consist of, a polynucleotide having a nucleotide sequence at least 80%, 85% or 90% identical, and more preferably at least 95%, 96%, 97%, 98% or 99% identical, to any of the nucleotide sequences in (a), (b), (c), (d), (e), (f) or (g) above, or a polynucleotide which hybridizes under stringent hybridization conditions to a polynucleotide in (a), (b), (c), (d), (e), (f) or (g) above. This polynucleotide which hybridizes does not hybridize under stringent hybridization conditions to a polynucleotide having a nucleotide sequence consisting of only A residues or of only T residues.

In additional embodiments, the nucleic acid molecules of the invention comprise, or alternatively consist of, a polynucleotide which encodes the amino acid sequence of an epitope-bearing portion of a D-SLAM polypeptide having an amino acid sequence in (a), (b), (c), (d), (e), (f) or (g) above. A further nucleic acid embodiment of the invention relates to an isolated nucleic acid molecule comprising, or alternatively consisting of, a polynucleotide which encodes the amino acid sequence of a D-SLAM polypeptide having an amino acid sequence which contains at least one amino acid addition, substitution, and/or deletion but not more than 50 amino acid additions, substitutions and/or deletions, even more preferably, not more than 40 amino acid additions, substitutions, and/or deletions, still more preferably, not more than 30 amino acid additions, substitutions, and/or deletions, and still even more preferably, not more than 20 amino acid additions, substitutions, and/or deletions. Of course, in order of ever-increasing preference, it is highly preferable for a polynucleotide which encodes the amino acid sequence of a D-SLAM polypeptide to have an amino acid sequence which contains not more than 10, 9, 8, 7, 6, 5, 4, 3, 2 or 1 or 1–100, 1–50, 1–25, 1–20, 1–15, 1–10, or 1–5 amino acid additions, substitutions and/or deletions. Conservative substitutions are preferable.

The present invention also relates to recombinant vectors, which include the isolated nucleic acid molecules of the present invention, and to host cells containing the recombinant vectors, as well as to methods of making such vectors and host cells and for using them for production of D-SLAM polypeptides by recombinant techniques.

In accordance with a further embodiment of the present invention, there is provided a process for producing such polypeptides by recombinant techniques comprising culturing recombinant prokaryotic and/or eukaryotic host cells, containing a D-SLAM nucleic acid sequence of the invention, under conditions promoting expression of said polypeptide and subsequent recovery of said polypeptide.

The invention further provides an isolated D-SLAM polypeptide comprising, or alternatively consisting of, an amino acid sequence selected from the group consisting of: (a) the amino acid sequence of the full-length D-SLAM polypeptide having the complete amino acid sequence shown in FIGS. 1A, 1B, 1C, and 1D (i.e., positions 1–285 of SEQ ID NO:2) or as encoded by the cDNA plasmid contained in the deposit having ATCC accession number 209623; (b) the amino acid sequence of the full-length D-SLAM polypeptide having the complete amino acid sequence shown in SEQ ID NO:2 excepting the N-terminal methionine (i.e., positions 2 to 285 of SEQ ID NO:2); (c) a fragment of the polypeptide of (b) having D-SLAM functional activity (e.g., biological activity (such as, for example, inhibition of B-cell proliferation)); (d) the amino acid sequence of the predicted extracellular domain of the D-SLAM polypeptide having the amino acid sequence at positions 23 to 232 in FIGS. 1A, 1B, 1C, and 1D (SEQ ID NO:2) or as encoded by the cDNA plasmid contained in the deposit having ATCC accession number 209623; (e) the amino acid sequence of the D-SLAM intracellular domain (predicted to constitute amino acid residues from about 256 to about 285 in FIGS. 1A, 1B, 1C, and 1D (SEQ ID NO:2)) or as encoded by the cDNA plasmid contained in the deposit having ATCC accession number 209623; (f) the amino acid sequence of the D-SLAM transmembrane domain (predicted to constitute amino acid residues from about 233 to about 255 in FIGS. 1A, 1B, 1C, and 1D (SEQ ID NO:2)) or as encoded by the cDNA plasmid contained in the deposit having ATCC accession number 209623; (g) the amino acid sequence of the soluble D-SLAM polypeptide having the extracellular and intracellular domains but lacking the transmembrane domain, wherein each of these domains is defined above; and (h) fragments of the polypeptide of (a), (b), (c), (d), (e), (f) or (g). The polypeptides of the present invention also include polypeptides having an amino acid sequence at least 80% identical, more preferably at least 85% or 90% identical, and still more preferably 95%, 96%, 97%, 98% or 99% identical to those described in (a), (b), (c), (d), (e), (f) or (g) above, as well as polypeptides having an amino acid sequence with at least 80%, 85%, or 90% similarity, and more preferably at least 95% similarity, to those above. Additional embodiments of the invention relates to polypeptides which comprise, or alternatively consist of, the amino acid sequence of an epitope-bearing portion of a D-SLAM polypeptide having an amino acid sequence described in (a), (b), (c), (d), (e), (f), (g) or (h) above. Polypeptides having the amino acid sequence of an epitope-bearing portion of a D-SLAM polypeptide of the invention include portions of such polypeptides with at least 4, at least 5, at least 6, at least 7, at least 8, and preferably at least 9, at least 10, at least 11, at least 12, at least 13, at least 14, at least 15, at least 20, at least 25, at least 30, at least 40, at least 50, and more preferably at least about 30 amino acids to about 50 amino acids, although epitope-bearing polypeptides of any length up to and including the entire amino acid sequence of a polypeptide of the invention described above also are included in the invention.

The present invention also encompasses the above polynucleotide sequences fused to a heterologous polynucleotide sequence. Polypeptides encoded by these polynucleotides and nucleic acid molecules are also encompassed by the invention.

Certain non-exclusive embodiments of the invention relate to a polypeptide which has the amino acid sequence of an epitope-bearing portion of a D-SLAM polypeptide having an amino acid sequence described in (a), (b), (c), (d), (e), (f), (g), (h) or (i) above. In other embodiments, the invention provides an isolated antibody that binds specifically (i.e., uniquely) to a D-SLAM polypeptide having an amino acid sequence described in (a), (b), (c), (d), (e), (f), (g), (h) or (i) above.

The invention further provides methods for isolating antibodies that bind specifically (i.e., uniquely) to a D-SLAM polypeptide having an amino acid sequence as described herein. Such antibodies are useful diagnostically or therapeutically as described below.

The invention also provides for pharmaceutical compositions comprising soluble D-SLAM polypeptides, particularly human D-SLAM polypeptides, and/or anti-D-SLAM antibodies which may be employed, for instance, to treat, prevent, prognose and/or diagnose tumor and tumor metastasis, infections by bacteria, viruses and other parasites, immunodeficiencies, inflammatory diseases, lymphadenopathy, autoimmune diseases, graft versus host disease, stimulate peripheral tolerance, destroy some transformed cell lines, mediate cell activation, survival and proliferation, to mediate immune regulation and inflammatory responses, and to enhance or inhibit immune responses.

In certain embodiments, soluble D-SLAM polypeptides of the invention, and/or antagonists of D-SLAM, are administered, to treat, prevent, prognose and/or diagnose an immunodeficiency (e.g., severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency) or conditions associated with an immunodeficiency.

In a specific embodiment, D-SLAM polypeptides or polynucleotides of the invention, or antagonists thereof, is administered to treat, prevent, prognose and/or diagnose common variable immunodeficiency.

In a specific embodiment, D-SLAM polypeptides or polynucleotides of the invention, or antagonists thereof, is administered to treat, prevent, prognose and/or diagnose X-linked agammaglobulinemia.

In another specific embodiment, D-SLAM polypeptides or polynucleotides of the invention, or antagonists thereof, is administered to treat, prevent, prognose and/or diagnose severe combined immunodeficiency (SCID).

In another specific embodiment, D-SLAM polypeptides or polynucleotides of the invention, or antagonists thereof, is administered to treat, prevent, prognose and/or diagnose Wiskott-Aldrich syndrome.

In another specific embodiment, D-SLAM polypeptides or polynucleotides of the invention, or antagonists thereof, is administered to treat, prevent, prognose and/or diagnose X-linked Ig deficiency with hyper IgM.

In another embodiment, D-SLAM agonists are administered to treat, prevent, prognose and/or diagnose an autoimmune disease (e.g., rheumatoid arthritis, systemic lupus erhythematosus, idiopathic thrombocytopenia purpura, autoimmune hemolytic anemia, autoimmune neonatal thrombocytopenia, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders) or conditions associated with an autoimmune disease. In a specific preferred embodiment, rheumatoid arthritis is treated, prevented, prognosed and/or diagnosed using D-SLAM and/or other agonists of the invention. In another specific preferred embodiment, systemic lupus erythemosus is treated, prevented, prognosed, and/or diagnosed using D-SLAM and/or other agonists of the invention. In another specific preferred embodiment, idiopathic thrombocytopenia purpura is treated, prevented, prognosed, and/or diagnosed using D-SLAM and/or other agonists of the invention. In another specific preferred embodiment IgA nephropathy is treated, prevented, prognosed and/or diagnosed using D-SLAM and/or other agonists of the invention. In a preferred embodiment, the autoimmune diseases and disorders and/or conditions associated with the diseases and disorders recited above are treated, prevented, prognosed and/or diagnosed using D-SLAM.

The invention further provides compositions comprising a D-SLAM polynucleotide, a D-SLAM polypeptide, and/or an anti-D-SLAM antibody, for administration to cells in vitro, to cells ex vivo, and to cells in vivo, or to a multicellular organism. In preferred embodiments, the compositions of the invention comprise a D-SLAM polynucleotide for expression of a D-SLAM polypeptide in a host organism for treatment of disease. In a most preferred embodiment, the compositions of the invention comprise a D-SLAM polynucleotide for expression of a D-SLAM polypeptide in a host organism for treatment of an immunodeficiency and/or conditions associated with an immunodeficiency. Particularly preferred in this regard is expression in a human patient for treatment of a dysfunction associated with aberrant endogenous activity of a D-SLAM gene.

The present invention also provides a screening method for identifying compounds capable of enhancing or inhibiting a cellular response induced by D-SLAM which involves contacting cells which express D-SLAM with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another embodiment, a method for identifying D-SLAM receptors is provided, as well as a screening assay for agonists and antagonists using such receptors. This assay involves determining the effect a candidate compound has on D-SLAM binding to the D-SLAM receptor. In particular, the method involves contacting a D-SLAM receptor with a D-SLAM polypeptide of the invention and a candidate compound and determining whether D-SLAM polypeptide binding to the D-SLAM receptor is increased or decreased due to the presence of the candidate compound. The agonists may be employed to prevent septic shock, inflammation, cerebral malaria, activation of the HIV virus, graft-host rejection, bone resorption, rheumatoid arthritis, cachexia (wasting or malnutrition), immune system function, lymphoma, and autoimmune disorders (e.g., rheumatoid arthritis and systemic lupus erythematosus).

The present inventors have discovered that D-SLAM is highly expressed in dendritic cells and lymph node, and to a lesser extent in spleen, thymus, small intestine, PBLs, bone marrow, T cell lymphoma, and even lesser extent in placenta and lung. For a number of disorders of these tissues and cells, such as tumor and tumor metastasis, infection of bacteria, viruses and other parasites, immunodeficiencies (e.g., chronic variable immunodeficiency), septic shock, inflammation, cerebral malaria, activation of the HIV virus, graft-host rejection, bone resorption, rheumatoid arthritis, autoimmune diseases (e.g., rheumatoid arthritis and systemic lupus erythematosus) and cachexia (wasting or malnutrition) it is believed that D-SLAM polynucleotides and/or polypeptides of the inventon are useful for diagnosis, prevention, treatment, and/or amelioration. It is believed that significantly higher or lower levels of D-SLAM gene expression can be detected in certain tissues (e.g., bone marrow) or bodily fluids (e.g., serum, plasma, urine, synovial fluid or spinal fluid) taken from an individual having such a disorder, relative to a "standard" D-SLAM gene expression level, i.e., the D-SLAM expression level in tissue or bodily fluids from an individual not having the disorder. Thus, the invention provides a diagnostic method useful during diagnosis of a disorder, which involves: (a) assaying D-SLAM gene expression level in cells or body fluid of an individual; (b) comparing the D-SLAM gene expression level with a standard D-SLAM gene expression level, whereby an increase or decrease in the assayed D-SLAM gene expression level compared to the standard expression level is indicative of a disorder.

An additional embodiment of the invention is related to a method for treating an individual in need of an increased or constitutive level of D-SLAM activity in the body comprising administering to such an individual a composition comprising a therapeutically effective amount of an isolated D-SLAM polypeptide of the invention or an agonist thereof.

Additionally, anti-D-SLAM antibodies (including anti-D-SLAM antibody fragments) against the polypeptides of the invention may be used to quantitate or qualitate concentrations of cells of dendritic cell lineage (e.g., dendritic cell related leukemias or lymphomas) expressing D-SLAM on their cell surfaces.

A still further embodiment of the invention is related to a method for treating an individual in need of a decreased level of D-SLAM activity in the body comprising, administering to such an individual a composition comprising a therapeutically effective amount of an D-SLAM antagonist. Preferred antagonists for use in the present invention are D-SLAM-specific antibodies.

BRIEF DESCRIPTION OF THE DRAWINGS

FIGS. 1A–1D show the nucleotide sequence (SEQ ID NO:1) and the deduced amino acid sequence (SEQ ID NO:2) of D-SLAM. The predicted leader sequence located at about amino acids 1–22 is underlined.

FIG. 2 shows the regions of identity between the amino acid sequence of the D-SLAM protein and the translation product of the human SLAM (Accession No. gi/984969) (SEQ ID NO:3), determined by BLAST analysis. Identical amino acids between the two polypeptides are shaded, while conservative amino acids are boxed. By examining the regions of amino acids shaded and/or boxed, the skilled artisan can readily identify conserved domains between the two polypeptides. These conserved domains are preferred embodiments of the present invention.

Figure 3:
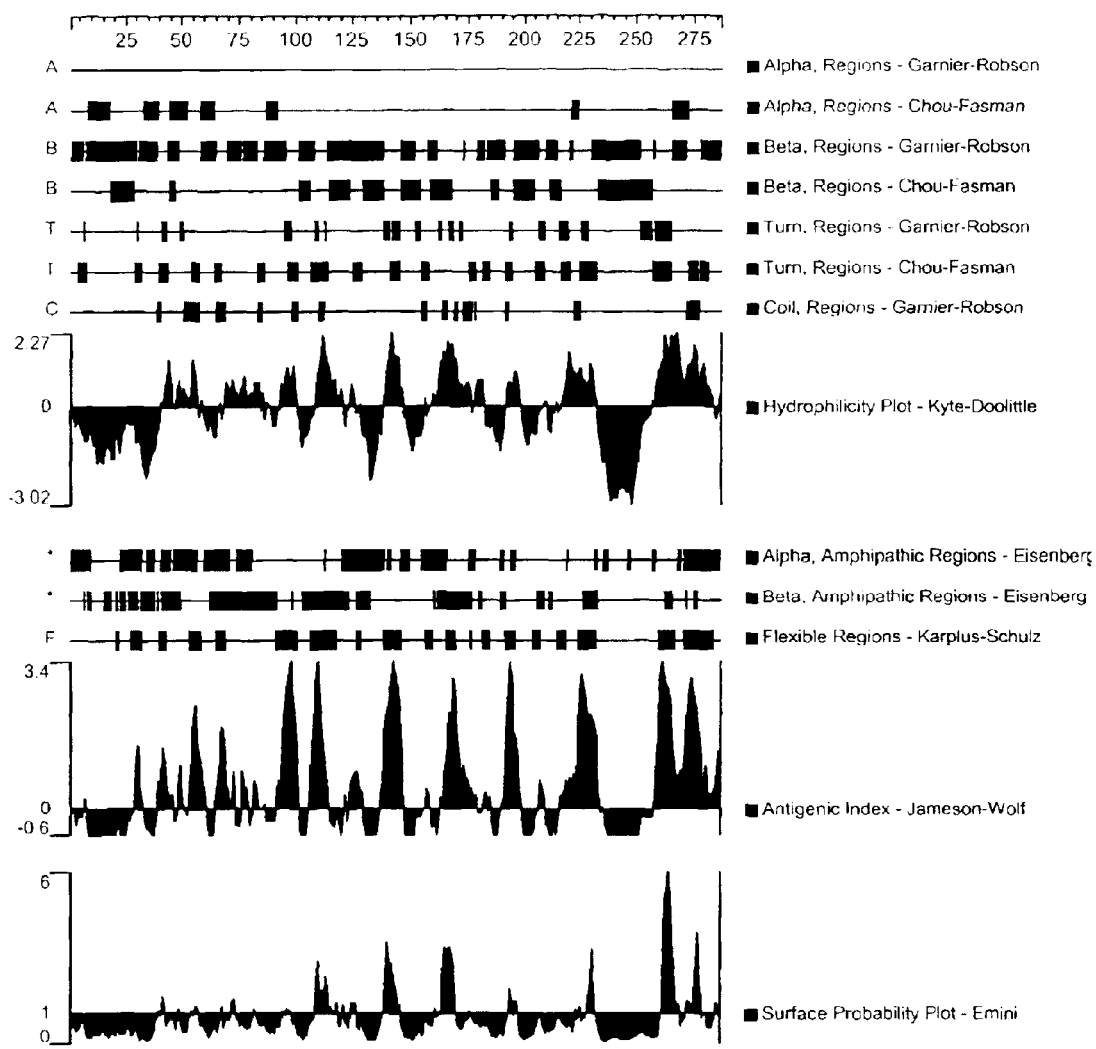
FIG. 3 shows an analysis of the D-SLAM amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the D-SLAM protein, i.e., regions from which epitope-bearing peptides of the invention can be obtained. The domains defined by these graphs are contemplated by the present invention. Tabular representation of the data summarized graphically in FIG. 3 can be found in Table 1.

The columns are labeled with the headings "Res", "Position", and Roman Numerals I–XIV. The column headings refer to the following features of the amino acid sequence presented in FIG. 3, and Table I "Res": amino acid residue of SEQ ID NO:2 and FIGS. 1A and 1B; "Position": position of the corresponding residue within SEQ ID NO:2 and FIGS. 1A and 1B; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Anphipathic Regions—Eisenberg; XII: Flexible Regions—Karplus-Schulz; XIII: Antigenic Index—Jameson-Wolf; and XIV: Surface Probability Plot—Emini.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome removed from a cell or a cell lysate (e.g., a "chromosome spread", as in a karyotype), or a preparation of randomly sheared genomic DNA or a preparation of genomic DNA cut with one or more restriction enzymes is not "isolated" for the purposes of this invention. As discussed further herein, isolated nucleic acid molecules according to the present invention may be produced naturally, recombinantly, or synthetically.

In the present invention, a "secreted" D-SLAM protein refers to a protein capable of being directed to the ER, secretory vesicles, or the extracellular space as a result of a signal sequence, as well as a D-SLAM protein released into the extracellular space without necessarily containing a signal sequence. If the D-SLAM secreted protein is released into the extracellular space, the D-SLAM secreted protein can undergo extracellular processing to produce a "mature" D-SLAM protein. Release into the extracellular space can occur by many mechanisms, including exocytosis and proteolytic cleavage.

As used herein, a D-SLAM "polynucleotide" refers to a molecule having a nucleic acid sequence contained in SEQ ID NO:1 or the cDNA contained within the clone deposited with the ATCC. For example, the D-SLAM polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a D-SLAM "polypeptide" refers to a molecule having the translated amino acid sequence generated from the polynucleotide as broadly defined.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of D-SLAM coding sequence, but do not comprise all or a portion of any D-SLAM intron. In another embodiment, the nucleic acid comprising D-SLAM coding sequence does not contain coding sequences of a genomic flanking gene (i.e., 5' or 3' to the D-SLAM gene in the genome).

In the present invention, the full length D-SLAM sequence identified as SEQ ID NO:1 was generated by overlapping sequences of the deposited clone (contig analysis). A representative clone containing all or most of the sequence for SEQ ID NO:1 was deposited with the American Type Culture Collection ("ATCC") on Feb. 6, 1998, and was given the ATCC Deposit Number 209623. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A D-SLAM "polynucleotide" also includes those polynucleotides capable of hybridizing, under stringent hybridization conditions, to sequences contained in SEQ ID NO:1, the complement thereof, or the cDNA within the deposited clone. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the D-SLAM polynucleotides at moderatetly high stringency hybridization conditions. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37 C in a solution comprising 6×SSPE (20×SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50 C with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The D-SLAM polynucleotide can be composed of any polyribonucleotide or polydeoxribonucleotide, which may be unmodified RNA or DNA or modified RNA or DNA. For example, D-SLAM polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the D-SLAM polynucleotides can be composed of triple-stranded regions comprising RNA or DNA or both RNA and DNA. D-SLAM polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

D-SLAM polypeptides can be composed of amino acids joined to each other by peptide bonds or modified peptide bonds, i.e., peptide isosteres, and may contain amino acids other than the 20 gene-encoded amino acids. The D-SLAM polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the D-SLAM polypeptide, including the peptide backbone, the amino acid side-chains and the amino or carboxyl termini. It will be appreciated that the same type of modification may be present in the same or varying degrees at several sites in a given D-SLAM polypeptide. Also, a given D-SLAM polypeptide may contain many types of modifications. D-SLAM polypeptides may be branched, for example, as a result of ubiquitination, and they may be cyclic, with or without branching. Cyclic, branched, and branched cyclic D-SLAM polypeptides may result from posttranslation natural processes or may be made by synthetic methods. Modifications include, but are not limited to, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, derivatization by known protecting/blocking groups, disulfide bond formation, demethylation, formation of covalent cross-links, formation of cysteine, formation of pyroglutamate, formylation, gamma-carboxylation, glycosylation, GPI anchor formation, hydroxylation, iodination, linkage to an antibody molecule or other cellular ligand, methylation, myristoylation, oxidation, pegylation, proteolytic processing (e.g., cleavage), phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).) Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein. In addition, polypeptides of the invention may be modified by iodination.

In one embodiment, D-SLAM polypeptides of the invention may also be labeled with biotin. In other related embodiments, biotinylated D-SLAM polypeptides of the invention may be used, for example, as an imaging agent or as a means of identifying one or more D-SLAM receptor(s) or other coreceptor or coligand molecules.

Also provided by the invention are chemically modified derivatives of D-SLAM which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59–72 (1996); Vorobjev et al., Nucleosides Nucleotides 18:2745–2750 (1999); and Caliceti et al., Bioconjug. Chem. 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($CISO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

The D-SLAM polypeptides can be recovered and purified by known methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

"SEQ ID NO:1" refers to a D-SLAM polynucleotide sequence while "SEQ ID NO:2" refers to a D-SLAM polypeptide sequence.

A D-SLAM polypeptide "having biological activity" refers to polypeptides exhibiting activity similar, but not necessarily identical to, an activity of a D-SLAM polypeptide, including mature forms, (e g., bind monocyte derived dendritic cells, upregulate cell surface markers indicative of dendritic cell maturation or activation (such as, for example, HLA-DR, CD54, CD86, CD83), inhibit B-cell proliferation, inhibit BLyS induced cell proliferative activity, bind an antibody which binds D-SLAM) as measured in a particular biological assay, with or without dose dependency. In the case where dose dependency does exist, it need not be identical to that of the D-SLAM polypeptide, but rather substantially similar to the dose-dependence in a given activity as compared to the D-SLAM polypeptide (i.e., the candidate polypeptide will exhibit greater activity or not more than about 25-fold less and, preferably, not more than about tenfold less activity, and most preferably, not more than about three-fold less activity relative to the D-SLAM polypeptide.)

D-SLAM Polynucleotides and Polypeptides

Clone HDPJO39 was isolated from a dendritic cell cDNA library. This clone contains the entire coding region identified as SEQ ID NO:2. The deposited clone contains a cDNA having a total of 3220 nucleotides, which encodes a predicted open reading frame of 285 amino acid residues. (See FIGS. 1A–1D.) The open reading frame begins at a N-terminal methionine located at nucleotide position 92, and ends at a stop codon at nucleotide position 947. The predicted molecular weight of the D-SLAM protein should be about 34.2 kDa.

Subsequent Northern analysis also showed D-SLAM expression in dendritic cells, T cell lymphoma, lymph node, spleen, thymus, small intestine, and uterus tissues, a pattern consistent with hematopoietic specific expression. Expression is highest in tissues involved in immune recognition, consistent with the enriched expression in dendritic cells and APC's. A single primary transcript of approximately 3.5–4.0 kb is observed, with a minor transcript of 7–9 kb that likely represents an unprocessed RNA precursor. The expression of the major 3.5–4 kb transcript is highest in lymph node, spleen, thymus, and, to a lesser degree, in small intestine. The highest expression of the 7–9 kb transcript is observed in the uterus.

Using BLAST analysis, SEQ ID NO:2 was found to be homologous to members of the Secreted Lymphocyte Activation Molecule (SLAM) family. Particularly, SEQ ID NO:2 contains domains homologous to the translation product of the human mRNA for SLAM (Accession No. gi/984969) (FIG. 2) (SEQ ID NO:3), including the following conserved domains: (a) a predicted transmembrane domain located at about amino acids 233–255; (b) a predicted extracellular domain located at about amino acids 23–232; and (c) a predicted intracellular domain located at about amino acids 256–285. These polypeptide fragments of D-SLAM are specifically contemplated in the present invention. Because SLAM (Accession No. gi/984969) is thought to be important in the activation and proliferation of T- and B-cells, the homology between SLAM (Accession No. gi/984969) and D-SLAM suggests that D-SLAM may also be involved in the activation and proliferation of T- and B-cells.

Moreover, the encoded polypeptide has a predicted leader sequence located at about amino acids 1–22. (See FIGS. 1A–1D.) Also shown in FIGS. 1A–1D, the predicted secreted form of D-SLAM encompasses about amino acids 23–232. These polypeptide fragments of D-SLAM are specifically contemplated in the present invention.

The D-SLAM nucleotide sequence identified as SEQ ID NO:1 was assembled from partially homologous ("overlapping") sequences obtained from the deposited clone, and in some cases, from additional related DNA clones. The overlapping sequences were assembled into a single contiguous sequence of high redundancy (usually three to five overlapping sequences at each nucleotide position), resulting in a final sequence identified as SEQ ID NO:1.

Therefore, SEQ ID NO:1 and the translated SEQ ID NO:2 are sufficiently accurate and otherwise suitable for a variety of uses well known in the art and described further below. For instance, SEQ ID NO:1 is useful for designing nucleic acid hybridization probes that will detect nucleic acid sequences contained in SEQ ID NO:1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used to generate antibodies which bind specifically to D-SLAM.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a human cDNA of D-SLAM deposited with the ATCC. The nucleotide sequence of the deposited D-SLAM clone can readily be determined by sequencing the deposited clone in accordance with known methods. The predicted D-SLAM amino acid sequence can then be verified from such deposits. Moreover, the amino acid sequence of the protein encoded by the deposited clone can also be directly determined by peptide sequencing or by expressing the protein in a suitable host cell containing the deposited human D-SLAM cDNA, collecting the protein, and determining its sequence.

The present invention also relates to the D-SLAM gene corresponding to SEQ ID NO:1, SEQ ID NO:2, or the deposited clone. The D-SLAM gene can be isolated in accordance with known methods using the sequence information disclosed herein. Such methods include preparing probes or primers from the disclosed sequence and identifying or amplifying the D-SLAM gene from appropriate sources of genomic material.

Also provided in the present invention are species homologs of D-SLAM. Species homologs may be isolated and identified by making suitable probes or primers from the sequences provided herein and screening a suitable nucleic acid source for the desired homologue.

The D-SLAM polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The D-SLAM polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

D-SLAM polypeptides are preferably provided in an isolated form, and preferably are substantially purified. A recombinantly produced version of a D-SLAM polypeptide, including the secreted polypeptide, can be substantially purified by the one-step method described in Smith and Johnson, Gene 67:31–40 (1988). D-SLAM polypeptides also can be purified from natural or recombinant sources using antibodies of the invention raised against the D-SLAM protein in methods which are well known in the art.

Polynucleotide and Polypeptide Variants

"Variant" refers to a polynucleotide or polypeptide differing from the D-SLAM polynucleotide or polypeptide, but retaining essential properties thereof. Generally, variants are overall closely similar, and, in many regions, identical to the D-SLAM polynucleotide or polypeptide.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the D-SLAM polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO:1, the ORF (open reading frame), or any fragment specified as described herein.

As a practical matter, whether any particular nucleic acid molecule or polypeptide is at least 80%, 85%, 90%, 92%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequences shown in SEQ ID NO:2 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score= 1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The D-SLAM variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. D-SLAM polynucleotide variants can be produced for a variety of reasons, e.g., to optimize codon expression for a particular host (change codons in the human mRNA to those preferred by a bacterial host such as E. coli).

Naturally occurring D-SLAM variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the D-SLAM polypeptides. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem. 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes D-SLAM polypeptide variants which show substantial biological activity. Such variants include deletions, insertions, inversions, repeats, and substitutions selected according to general rules known in the art so as have little effect on activity.

The present application is directed to nucleic acid molecules at least 80%, 85%, 90%, 92%, 95%, 96%, 97%, 98% or 99% identical to the nucleic acid sequences disclosed herein, (e.g., encoding a polypeptide having the amino acid sequence of an N and/or C terminal deletion disclosed below as m-n of SEQ ID NO:2), irrespective of whether they encode a polypeptide having D-SLAM functional activity. This is because even where a particular nucleic acid molecule does not encode a polypeptide having D-SLAM functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having D-SLAM functional activity include, inter alia, (1) isolating a D-SLAM gene or allelic or splice variants thereof in a cDNA library, (2) in situ hybridization (e.g., "FISH") to metaphase chromosomal spreads to provide precise chromosomal location of the D-SLAM gene, as described in Verma et al., Human Chromosomes: A Manual of Basic Techniques, Pergamon Press, New York (1988); and (3) Northern Blot analysis for detecting D-SLAM mRNA expression in specific tissues.

Preferred, however, are nucleic acid molecules having sequences at least 80%, 85%, 90%, 92%, 95%, 96%, 97%, 98% or 99% identical to the nucleic acid sequences disclosed herein, which do, in fact, encode a polypeptide having D-SLAM functional activity. By "a polypeptide having D-SLAM functional activity" is intended polypeptides capable of exhibiting activity similar, but not necessarily identical, to a known functional activity of the D-SLAM polypeptides of the present invention (e.g., complete (full-length) D-SLAM, mature D-SLAM and soluble D-SLAM (e.g., having sequences contained in the extracellular domain of D-SLAM) as measured, for example, in a particular immunoassay or biological assay. Such functional activities include, but are not limited to, biological activity (e.g., ability to bind monocyte derived dendritic cells, ability to upregulate cell surface markers indicative of dendritic cell maturation or activation (such as, for example, HLA-DR, CD54, CD86, CD83), ability to inhibit B-cell proliferation, ability to inhibit BLyS induced cell proliferative activity, antigenicity (ability to bind or compete with a D-SLAM polypeptide for binding to an anti-D-SLAM antibody), immunogenicity (ability to generate an antibody which specifically binds to a D-SLAM polypeptide), ability to form multimers with D-SLAM polypeptides of the invention, ability to form heteromultimers, ability to bind to a receptor or ligand). For example, a D-SLAM functional activity can routinely be measured by determining the ability of a D-SLAM polypeptide to bind a D-SLAM ligand. D-SLAM functional activity may also be measured by determining the ability of a polypeptide, such as cognate ligand which is free or expressed on a cell surface, to induce cells expressing the polypeptide.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98%, or 99% identical to the nucleic acid sequence of the deposited cDNA, the nucleic acid sequence shown in FIG. 1 (SEQ ID NO:1), or fragments thereof, will encode polypeptides "having D-SLAM functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having D-SLAM functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For example, site directed changes at the amino acid level of D-SLAM can be made by replacing a particular amino acid with a conservative amino acid. Preferred conservative mutations include: M1 replaced with A, G, I, L, S, T, or V; V2 replaced with A, G, I, L, S, T, or M; M3 replaced with A, G, I, L, S, T, or V; R4 replaced with H, or K; L6 replaced with A, G, I, S, T, M, or V; W7 replaced with F, or Y; S8 replaced with A, G, I, L, T, M, or V; L9 replaced with A, G, I, S, T, M, or V; L10 replaced with A, G, I, S, T, M, or V; L11 replaced with A, G, I, S, T, M, or V; W12 replaced with F, or Y; E13 replaced with D; A14 replaced with G, I, L, S, T, M, or V; L15 replaced with A, G, I, S, T, M, or V; L16 replaced with A, G, I, S, T, M, or V; I18 replaced with A, G, L, S, T, M, or V; T19 replaced with A, G, I, L, S, M, or V; V20 replaced with A, G, I, L, S, T, or M; T21 replaced with A, G, I, L, S, M, or V; G22 replaced with A, I, L, S, T, M, or V; A23 replaced with G, I, L, S, T, M, or V; Q24 replaced with N; V25 replaced with A, G, I, L, S, T, or M; L26 replaced with A, G, I, S, T, M, or V; S27 replaced with A, G, I, L, T, M, or V; K28 replaced with H, or R; V29 replaced with A, G, I, L, S, T, or M; G30 replaced with A, I, L, S, T, M, or V; G31 replaced with A, I, L, S, T, M, or V; S32 replaced with A, G, I, L, T, M, or V; V33 replaced with A, G, I, L, S, T, or M; L34 replaced with A, G, I, S, T, M, or V; L35 replaced with A, G, I, S, T, M, or V; V36 replaced with A, G, I, L, S, T, or M; A37 replaced with G, I, L, S, T, M, or V; A38 replaced with G, I, L, S, T, M, or V; R39 replaced with H, or K; G42 replaced with A, I, L, S, T, M, or V; F43 replaced with W, or Y; Q44 replaced with N; V45 replaced with A, G, I, L, S, T, or M; R46 replaced with H, or K; E47 replaced with D; A48 replaced with G, I, L, S, T, M, or V; I49 replaced with A, G, L, S, T, M, or V; W50 replaced with F, or Y; R51 replaced with H, or K; S52 replaced with A, G, I, L, T, M, or V; L53 replaced with A, G, I, S, T, M, or V; W54 replaced with F, or Y; S56 replaced with A, G, I, L, T, M, or V; E57 replaced with D; E58 replaced with D; L59 replaced with A, G, I, S, T, M, or V; L60 replaced with A, G, I, S, T, M, or V; A61 replaced with G, I, L, S, T, M, or V; T62 replaced with A, G, I, L, S, M, or V; F63 replaced with W, or Y; F64 replaced with W, or Y; R65 replaced with H, or K; G66 replaced with A, I, L, S, T, M, or V; S67 replaced with A, G, I, L, T, M, or V; L68 replaced with A, G, I, S, T, M, or V; E69 replaced with D; T70 replaced with A, G, I, L, S, M, or V; L71 replaced with A, G, I, S, T, M, or V; Y72 replaced with F, or W; H73 replaced with K, or R; S74 replaced with A, G, I, L, T, M, or V; R75 replaced with H, or K; F76 replaced with W, or Y; L77 replaced with A, G, I, S, T, M, or V; G78 replaced with A, I, L, S, T, M, or V; R79 replaced with H, or K; A80 replaced with G, I, L, S, T, M, or V; Q81 replaced with N; L82 replaced with A, G, I, S, T, M, or V; H83 replaced with K, or R; S84 replaced with A, G, I, L, T, M, or V; N85 replaced with Q; L86 replaced with A, G, I, S, T, M, or V; S87 replaced with A, G, I, L, T, M, or V; L88 replaced with A, G, I, S, T, M, or V; E89 replaced with D; L90 replaced with A, G, I, S, T, M, or V; G91 replaced with A, I, L, S, T, M, or V; L93 replaced with A, G, I, S, T, M, or V; E94 replaced with D; S95 replaced with A, G, I, L, T, M, or V; G96 replaced with A, I, L, S, T, M, or V; D97 replaced with E; S98 replaced with A, G, I, L, T, M, or V; G99 replaced with A, I, L, S, T, M, or V; N100 replaced with Q; F101 replaced with W, or Y; S102 replaced with A, G, I, L, T, M, or V; V103 replaced with A, G, I, L, S, T, or M; L104 replaced with A, G, I, S, T, M, or V; M105 replaced with A, G, I, L, S, T, or V; V106 replaced with A, G, I, L, S, T, or M; D107 replaced with E; T108 replaced with A, G, I, L, S, M, or V; R109 replaced with H, or K; G110 replaced with A, I, L, S, T, M, or V; Q111 replaced with N; W113 replaced with F, or Y; T114 replaced with A, G, I, L, S, M, or V; Q115 replaced with N; T116 replaced with A, G, I, L, S, M, or V; L117 replaced with A, G, I, S, T, M, or V; Q118 replaced with N; L119 replaced with A, G, I, S, T, M, or V; K120 replaced with H, or R; V121 replaced with A, G, I, L, S, T, or M; Y122 replaced with F, or W; D123 replaced with E; A124 replaced with G, I, L, S, T, M, or V; V125 replaced with A, G, I, L, S, T, or M; R127 replaced with H, or K; V129 replaced with A, G, I, L, S, T, or M; V130 replaced with A, G, I, L, S, T, or M; Q131 replaced with N; V132 replaced with A, G, I, L, S, T, or M; F133 replaced with W, or Y; I134 replaced with A, G, L, S, T, M, or V; A135 replaced with G, I, L, S, T, M, or V; V136 replaced with A, G, I, L, S, T, or M; E137 replaced with D; R138 replaced with H, or K; D139 replaced with E; A140 replaced with G, I, L, S, T, M, or V; Q141 replaced with N; S143 replaced with A, G, I, L, T, M, or V; K144 replaced with H, or R; T145 replaced with A, G, I, L, S, M, or V; Q147 replaced with N; V148 replaced with A, G, I, L, S, T, or M; F149 replaced with W, or Y; L150 replaced with A, G, I, S, T, M, or V; S151 replaced with A, G, I, L, T, M, or V; W153 replaced with F, or Y; A154 replaced with G, I, L, S, T, M, or V; N156 replaced with Q; I157 replaced with A, G, L, S, T, M, or V; S158 replaced with A, G, I, L, T, M, or V; E159 replaced with D; I160 replaced with A, G, L, S, T, M, or V; T161 replaced with A, G, I, L, S, M, or V; Y162 replaced with F, or W; S163 replaced with A, G, I, L, T, M, or V; W164 replaced with F, or Y; R165 replaced with H, or K; R166 replaced with H, or K; E167 replaced with D; T168 replaced with A, G, I, L, S, M, or V; T169 replaced with A, G, I, L, S, M, or V; M170 replaced with A, G, I, L, S, T, or V; D171 replaced with E; F172 replaced with W, or Y; G173 replaced with A, I, L, S, T, M, or V; M174 replaced with A, G, I, L, S, T, or V; E175 replaced with D; H177 replaced with K, or R; S178 replaced with A, G, I, L, T, M, or V; L179 replaced with A, G, I, S, T, M, or V; F180 replaced with W, or Y; T181 replaced with A, G, I, L, S, M, or V; D182 replaced with E; G183 replaced with A, I, L, S, T, M, or V; Q184 replaced with N; V185 replaced with A, G, I, L, S, T, or M; L186 replaced with A, G, I, S, T, M, or V; S187 replaced with A, G, I, L, T, M, or V; I188 replaced with A, G, L, S, T, M, or V; S189 replaced with A, G, I, L, T, M, or V; L190 replaced with A, G, I, S, T, M, or V; G191 replaced with A, I, L, S, T, M, or V; G193 replaced with A, I, L, S, T, M, or V; D194 replaced with E; R195 replaced with H, or K; D196 replaced with E; V197 replaced with A, G, I, L, S, T, or M; A198 replaced with G, I, L, S, T, M, or V; Y199 replaced with F, or W; S200 replaced with A, G, I, L, T, M, or V; I202 replaced with A, G, L, S, T, M, or V; V203 replaced with A, G, I, L, S, T, or M; S204 replaced with A, G, I, L, T, M, or V; N205 replaced with Q; V207 replaced with A, G, I, L, S, T, or M; S208 replaced with A, G, I, L, T, M, or V; W209 replaced with F, or Y; D210 replaced with E; L211 replaced with A, G, I, S, T, M, or V; A212 replaced with G, I, L, S, T, M, or V; T213 replaced with A, G, I, L, S, M, or V; V214 replaced with A, G, I, L, S, T, or M; T215 replaced with A, G, I, L, S, M, or V; W217 replaced with F, or Y; D218 replaced with E; S219 replaced with A, G, I, L, T, M, or V; H221 replaced with K, or R; H222 replaced with K, or R; E223 replaced with D; A224 replaced with G, I, L, S, T, M, or V; A225 replaced with G, I, L, S, T, M, or V; G227 replaced with A, I, L, S, T, M, or V; K228 replaced with H, or R; A229 replaced with G I, L, S, T, M, or V; S230 replaced with A, G, I, L, T, M, or V; Y231 replaced with F, or W; K232 replaced with H, or R; D233 replaced with E; V234 replaced with A, G, I, L, S, T, or M; L235 replaced with A, G, I, S, T, M, or V; L236 replaced with A, G, I, S, T, M, or V; V237 replaced with A, G, I, L, S, T, or M; V238 replaced with A, G, I, L, S, T, or M; V239 replaced with A, G, I, L, S, T, or M; V241 replaced with A, G, I, L, S, T, or M; S242 replaced with A, G, I, L, T, M, or V; L243 replaced with A, G, I, S, T, M, or V; L244 replaced with A, G, I, S, T, M, or V; L245 replaced with A, G, I, S, T, M, or V; M246 replaced with A, G, I, L, S, T, or V; L247 replaced with A, G, I, S, T, M, or V; V248 replaced with A, G, I, L, S, T, or M; T249 replaced with A, G, I, L, S, M, or V; L250 replaced with A, G, I, S, T, M, or V; F251 replaced with W, or Y; S252 replaced with A, G, I, L, T, M, or V; A253 replaced with G, I, L, S, T, M, or V; W254 replaced with F, or Y; H255 replaced with K, or R; W256 replaced with F, or Y; S260 replaced with A, G, I, L, T, M, or V; G261 replaced with A, I, L, S, T, M, or V; K262 replaced with H, or R; K263 replaced with H, or R; K264 replaced with H, or R; K265 replaced with H, or R; D266 replaced with E; V267 replaced with A, G, I, L, S, T, or M; H268 replaced with K, or R; A269 replaced with G, I, L, S, T, M, or V; D270 replaced with E; R271 replaced with H, or K; V272 replaced with A, G, I, L, S, T, or M; G273 replaced with A, I, L, S, T, M, or V; E275 replaced with D; T276 replaced with A, G, I, L, S, M, or V; E277 replaced with D; N278 replaced with Q; L280 replaced with A, G, I, S, T, M, or V; V281 replaced with A, G, I, L, S, T, or M; Q282 replaced with N; D283 replaced with E; L284 replaced with A, G, I, S, T, M, or V.

The resulting constructs can be routinely screened for activities or functions described throughout the specification and known in the art. Preferably, the resulting constructs have an increased D-SLAM activity or function, while the remaining D-SLAM activities or functions are maintained. More preferably, the resulting constructs have more than one increased D-SLAM activity or function, while the remaining D-SLAM activities or functions are maintained.

Besides conservative amino acid substitution, variants of D-SLAM include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, D-SLAM polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

For example, preferred non-conservative substitutions of D-SLAM include: M1 replaced with D, E, H, K, R, N, Q, F, W, Y, P, or C; V2 replaced with D, E, H, K, R, N, Q, F, W, Y, P, or C; M3 replaced with D, E, H, K, R, N, Q, F, W, Y, P, or C; R4 replaced with D, E, A, G, I, L, S, T, M, V, N, Q, F, W, Y, P, or C; P5 replaced with D, E, H, K, R, A, G, I, L, S, T, M, V, N, Q, F, W, Y, or C; L6 replaced with D, E, H, K, R, N, Q, F, W, Y, P, or C; W7 replaced with D, E, H, K, R, N, Q, A, G, I, L, S, T, M, V, P, or C; S8 replaced with D, E, H, K, R, N, Q, F, W, Y, P, or C; L9 replaced with D, E, H, K, R, N, Q, F, W, Y, P, or C; L10 replaced with D, E, H, K, R, N, Q, F, W, Y, P, or C; L11 replaced with D, E, H, K, R, N, Q, F, W, Y, P, or C; W12 replaced with D, E, H, K, R, N, Q, A, G, I, L, S, T, M, V, P, or C; E13 replaced with H, K, R, A, G, I, L, S, T, M, V, N, Q, F, W, Y, P, or C; A14 replaced with D, E, H, K, R, N, Q, F, W, Y, P, or C; L15 replaced with D, E, H, K, R, N, Q, F, W, Y, P, or C; L16 replaced with D, E, H, K, R, N, Q, F, W, Y, P, or C; P17 replaced with D, E, H, K, R, A, G, I, L, S, T, M, V, N, Q, F, W, Y, or C; I18 replaced with D, E, H, K, R, N, Q, F, W, Y, P, or C; T19 replaced with D, E, H, K, R, N, Q, F, W, Y, P, or C; V20 replaced with D, E, H, K, R, N, Q, F, W, Y, P, or C; T21 replaced with D, E, H, K, R, N, Q, F, W, Y, P, or C; G22 replaced with D, E, H, K, R, N, Q, F, W, Y, P, or C; A23 replaced with D, E, H, K, R, N, Q, F, W, Y, P, or C; Q24 replaced with D, E, H, K, R, A, G, I, L, S, T, M, V, F, W, Y, P, or C; V25 replaced with D, E, H, K, R, N, Q, F, W, Y, P, or C; L26 replaced with D, E, H, K, R, N, Q, F, W, Y, P, or C; S27 replaced with D, E, H, K, R, N, Q, F, W, Y, P, or C; K28 replaced with D, E, A, G, I, L, S, T, M, V, N, Q, F, W, Y, P, or C; V29 replaced with D, E, H, K, R, N, Q, F, W, Y, P, or C; G30 replaced with D, E, H, K, R, N, Q, F, W, Y, P, or C; G31 replaced with D, E, H, K, R, N, Q, F, W, Y, P, or C; S32 replaced with D, E, H, K, R, N, Q, F, W, Y, P, or C; V33 replaced with D, E, H, K, R, N, Q, F, W, Y, P, or C; L34 replaced with D, E, H, K, R, N, Q, F, W, Y, P, or C; L35 replaced with D, E, H, K, R, N, Q, F, W, Y, P, or C; V36 replaced with D, E, H, K, R, N, Q, F, W, Y, P, or C; A37 replaced with D, E, H, K, R, N, Q, F, W, Y, P, or C; A38 replaced with D, E, H, K, R, N, Q, F, W, Y, P, or C; R39 replaced with D, E, A, G, I, L, S, T, M, V, N, Q, F, W, Y, P, or C; P40 replaced with D, E, H, K, R, A, G, I, L, S, T, M, V, N, Q, F, W, Y, or C; P41 replaced with D, E, H, K, R, A, G, I, L, S, T, M, V, N, Q, F, W, Y, or C; G42 replaced with D, E, H, K, R, N, Q, F, W, Y, P, or C; F43 replaced with D, E, H, K, R, N, Q, A, G, I, L, S, T, M, V, P, or C; Q44 replaced with D, E, H, K, R, A, G, I, L, S, T, M, V, F, W, Y, P, or C; V45 replaced with D, E, H, K, R, N, Q, F, W, Y, P, or C; R46 replaced with D, E, A, G, I, L, S, T, M, V, N, Q, F, W, Y, P, or C; E47 replaced with H, K, R, A, G, I, L, S, T, M, V, N, Q, F, W, Y, P, or C; A48 replaced with D, E, H, K, R, N, Q, F, W, Y, P, or C; I49 replaced with D, E, H, K, R, N, Q, F, W, Y, P, or C; W50 replaced with D, E, H, K, R, N, Q, A, G, I, L, S, T, M, V, P, or C; R51 replaced with D, E, A, G, I, L, S, T, M, V, N, Q, F, W, Y, P, or C; S52 replaced with D, E, H, K, R, N, Q, F, W, Y, P, or C; L53 replaced with D, E, H, K, R, N, Q, F, W, Y, P, or C; W54 replaced with D, E, H, K, R, N, Q, A, G, I, L, S, T, M, V, P, or C; P55 replaced with D, E, H, K, R, A, G, I, L, S, T, M, V, N, Q, F, W, Y, or C; S56 replaced with D, E, H, K, R, N, Q, F, W, Y, P, or C; E57 replaced with H, K, R, A, G, I, L, S, T, M, V, N, Q, F, W, Y, P, or C; E58 replaced with H, K, R, A, G, I, L, S, T, M, V, N, Q, F, W, Y, P, or C; L59 replaced with D, E, H, K, R, N, Q, F, W, Y, P, or C; L60 replaced with D, F, H, K, R, N, Q, F, W, Y, P, or C; A61 replaced with D, E, H, K, R, N, Q, F, W, Y, P, or C; T62 replaced with D, E, H, K, R, N, Q, F, W, Y, P, or C; F63 replaced with D, E, H, K, R, N, Q, A, G, I, L, S, T, M, V, P, or C; F64 replaced with D, E, H, K, R, N, Q, A, G, I, L, S, T, M, V, P, or C; R65 replaced with D, E, A, G, I, L, S, T, M, V, N, Q, F, W, Y, P, or C; G66 replaced with D, E, H, K, R, N, Q, F, W, Y, P, or C; S67 replaced with D, E, H, K, R, N, Q, F, W, Y, P, or C; L68 replaced with D, E, H, K, R, N, Q, F, W, Y, P, or C; E69 replaced with H, K, R, A, G, I, L, S, T, M, V, N, Q, F, W, Y, P, or C; T70 replaced with D, E, H, K, R, N, Q, F, W, Y, P, or C; L71 replaced with D, E, H, K, R, N, Q, F, W, Y, P, or C; Y72 replaced with D, E, H, K, R, N, Q, A, G, I, L, S, T, M, V, P, or C; H73 replaced with D, E, A, G, I, L, S, T, M, V, N, Q, F, W, Y, P, or C; S74 replaced with D, E, H, K, R, N, Q, F, W, Y, P, or C; R75 replaced with D, E, A, G, I, L, S, T, M, V, N, Q, F, W, Y, P, or C; F76 replaced with D, E, H, K, R, N, Q, A, G, I, L, S, T, M, V, P, or C; L77 replaced with D, E, H, K, R, N, Q, F, W, Y, P, or C; G78 replaced with D, E, H, K, R, N, Q, F, W, Y, P, or C; R79 replaced with D, E, A, G, I, L, S, T, M, V, N, Q, F, W, Y, P, or C; A80 replaced with D, E, H, K, R, N, Q, F, W, Y, P, or C; Q81 replaced with D, E, H, K, R, A, G, I, L, S, T, M, V, F, W, Y, P, or C; L82 replaced with D, E, H, K, R, N, Q, F, W, Y, P, or C; H83 replaced with D, E, A, G, I, L, S, T, M, V, N, Q, F, W, Y, P, or C; S84 replaced with D, E, H, K, R, N, Q, F, W, Y, P, or C; N85 replaced with D, E, H, K, R, A, G, I, L, S, T, M, V, F, W, Y, P, or C; L86 replaced with D, E, H, K, R, N, Q, F, W, Y, P, or C; S87 replaced with D, E, H, K, R, N, Q, F, W, Y, P, or C; L88 replaced with D, E, H, K, R, N, Q, F, W, Y, P, or C; E89 replaced with H, K, R, A, G, I, L, S, T, M, V, N, Q, F, W, Y, P, or C; L90 replaced with D, E, H, K, R, N, Q, F, W, Y, P, or C; G91 replaced with D, E, H, K, R, N, Q, F, W, Y, P, or C; P92 replaced with D, E, H, K, R, A, G, I, L, S, T, M, V, N, Q, F, W, Y, or C; L93 replaced with D, E, H, K, R, N, Q, F, W, Y, P, or C; E94 replaced with H, K, R, A, G, I, L, S, T, M, V, N, Q, F, W, Y, P, or C; S95 replaced with D, E, H, K, R, N, Q, F, W, Y, P, or C; G96 replaced with D, E, H, K, R, N, Q, F, W, Y, P, or C; D97 replaced with H, K, R, A, G, I, L, S, T, M, V, N, Q, F, W, Y, P, or C; S98 replaced with D, E, H, K, R, N, Q, F, W, Y, P, or C; G99 replaced with D, E, H, K, R, N, Q, F, W, Y, P, or C; N100 replaced with D, E, H, K, R, A, G, I, L, S, T, M, V, F, W, Y, P, or C; F101 replaced with D, E, H, K, R, N, Q, A, G, I, L, S, T, M, V, P, or C; S102 replaced with D, E, H, K, R, N, Q, F, W, Y, P, or C; V103 replaced with D, E, H, K, R, N, Q, F, W, Y, P, or C; L104 replaced with D, E, H, K, R, N, Q, F, W, Y, P, or C; M105 replaced with D, E, H, K, R, N, Q, F, W, Y, P, or C; V106 replaced with D, E, H, K, R, N, Q, F, W, Y, P, or C; D107 replaced with H, K, R, A, G, I, L, S, T, M, V, N, Q, F, W, Y, P, or C; T108 replaced with D, E, H, K, R, N, Q, F, W, Y, P, or C; R109 replaced with D, E, A, G, I, L, S, T, M, V, N, Q, F, W, Y, P, or C; G110 replaced with D, E, H, K, R, N, Q, F, W, Y, P, or C; Q111 replaced with D, E, H, K, R, A, G, I, L, S, T, M, V, F, W, Y, P, or C; P112 replaced with D, E, H, K, R, A, G, I, L, S, T, M, V, N, Q, F, W, Y, or C; W113 replaced with D, E, H, K, R, N, Q, A, G, I, L, S, T, M, V, P, or C; T114 replaced with D, E, H, K, R, N, Q, F, W, Y, P, or C; Q115 replaced with D, E, H, K, R, A, G, I, L, S, T, M, V, F, W, Y, P, or C; T116 replaced with D, E, H, K, R, N, Q, F, W, Y, P, or C; L117 replaced with D, E, H, K, R, N, Q, F, W, Y, P, or C; Q118 replaced with D, E, H, K, R, A, G, I, L, S, T, M, V, F, W, Y, P, or C; L119 replaced with D, E, H, K, R, N, Q, F, W, Y, P, or C; K120 replaced with D, E, A, G, I, L, S, T, M, V, N, Q, F, W, Y, P, or C; V121 replaced with D, E, H, K, R, N, Q, F, W, Y, P, or C; Y122 replaced with D, E, H, K, R, N, Q, A, G, I, L, S, T, M, V, P, or C; D123 replaced with H, K, R, A, G, I, L, S, T, M, V, N, Q, F, W, Y, P, or C; A124 replaced with D, E, H, K, R, N, Q, F, W, Y, P or C; V125 replaced with D, E, H, K, R, N, Q, F, W, Y, P or C; P126 replaced with D, E, H, K, R, A, G, I, L, S, T, M, V, N, Q, F, W, Y, or C; R127 replaced with D, E, A, G, I, L, S, T, M, V, N, Q, F, W, Y, P, or C; P128 replaced with D, E, H, K, R, A, G, I, L, S, T, M, V, N, Q, F, W, Y, or C; V129 replaced with D, E, H, K, R, N, Q, F, W, Y, P, or C; V130 replaced with D, E, H, K, R, N, Q, F, W, Y, P, or C; Q131 replaced with D, E, H, K, R, A, G, I, L, S, T, M, V, F, W, Y, P, or C; V132 replaced with D, E, H, K, R, N, Q, F, W, Y, P, or C; F133 replaced with D, E, H, K, R, N, Q, A, G, I, L, S, T, M, V, P, or C; I134 replaced with D, E, H, K, R, N, Q, F, W, Y, P, or C; A135 replaced with D, E, H, K, R, N, Q, F, W, Y, P, or C; V136 replaced with D, E, H, K, R, N, Q, F, W, Y, P, or C; E137 replaced with H, K, R, A, G, I, L, S, T, M, V, N, Q, F, W, Y, P, or C; R138 replaced with D, E, A, G, I, L, S, T, M, V, N, Q, F, W, Y, P, or C; D139 replaced with H, K, R, A, G, I, L, S, T, M, V, N, Q, F, W, Y, P, or C; A140 replaced with D, E, H, K, R, N, Q, F, W, Y, P, or C; Q141 replaced with D, E, H, K, R, A, G, I, L, S, T, M, V, F, W, Y, P, or C; P142 replaced with D, E, H, K, R, A, G, I, L, S, T, M, V, N, Q, F, W, Y, or C; S143 replaced with D, E, H, K, R, N, Q, F, W, Y, P, or C; K144 replaced with D, E, A, G, I, L, S, T, M, V, N, Q, F, W, Y, P, or C; T145 replaced with D, E, H, K, R, N, Q, F, W, Y, P, or C; C146 replaced with D, E, H, K, R, A, G, I, L, S, T, M, V, N, Q, F, W, Y, or P; Q147 replaced with D, E, H, K, R, A, G, I, L, S, T, M, V, F, W, Y, P, or C; V148 replaced with D, E, H, K, R, N, Q, F, W, Y, P, or C; F149 replaced with D, E, H, K, R, N, Q, A, G, I, L, S, T, M, V, P, or C; L150 replaced with D, E, H, K, R, N, Q, F, W, Y, P, or C; S151 replaced with D, E, H, K, R, N, Q, F, W, Y, P, or C; C152 replaced with D, E, H, K, R, A, G, I, L, S, T, M, V, N, Q, F, W, Y, or P; W153 replaced with D, E, H, K, R, N, Q, A, G, I, L, S, T, M, V, P, or C; A154 replaced with D, E, H, K, R, N, Q, F, W, Y, P, or C; P155 replaced with D, E, H, K, R, A, G, I, L, S, T, M, V, N, Q, F, W, Y, or C; N156 replaced with D, E, H, K, R, A, G, I, L, S, T, M, V, F, W, Y, P, or C; I157 replaced with D, E, H, K, R, N, Q, F, W, Y, P, or C; S158 replaced with D, E, H, K, R, N, Q, F, W, Y, P, or C; E159 replaced with H, K, R, A, G, I, L, S, T, M, V, N, Q, F, W, Y, P, or C; I160 replaced with D, E, H, K, R, N, Q, F, W, Y, P, or C; T161 replaced with D, E, H, K, R, N, Q, F, W, Y, P, or C; Y162 replaced with D, E, H, K, R, N, Q, A, G, I, L, S, T, M, V, P, or C; S163 replaced with D, E, H, K, R, N, Q, F, W, Y, P, or C; W164 replaced with D, E, H, K, R, N, Q, A, G, I, L, S, T, M, V, P, or C; R165 replaced with D, E, A, G, I, L, S, T, M, V, N, Q, F, W, Y, P, or C; R166 replaced with D, E, A, G, I, L, S, T, M, V, N, Q, F, W, Y, P, or C; E167 replaced with H, K, R, A, G, I, L, S, T, M, V, N, Q, F, W, Y, P, or C; T168 replaced with D, E, H, K, R, N, Q, F, W, Y, P, or C; T169 replaced with D, E, H, K, R, N, Q, F, W, Y, P, or C; M170 replaced with D, E, H, K, R, N, Q, F, W, Y, P, or C; D171 replaced with H, K, R, A, G, I, L, S, T, M, V, N, Q, F, W, Y, P, or C; F172 replaced with D, E, H, K, R, N, Q, A, G, I, L, S, T, M, V, P, or C; G173 replaced with D, E, H, K, R, N, Q, F, W, Y, P, or C; M174 replaced with D, E, H, K, R, N, Q, F, W, Y, P, or C; E175 replaced with H, K, R, A, G, I, L, S, T, M, V, N, Q, F, W, Y, P, or C; P176 replaced with D, E, H, K, R, A, G, I, L, S, T, M, V, N, Q, F, W, Y, or C; H177 replaced with D, E, A, G, I, L, S, T, M, V, N, Q, F, W, Y, P, or C; S178 replaced with D, E, H, K, R, N, Q, F, W, Y, P, or C; L179 replaced with D, E, H, K, R, N, Q, F, W, Y, P, or C; F180 replaced with D, E, H, K, R, N, Q, A, G, I, L, S, T, M, V, P, or C; T181 replaced with D, E, H, K, R, N, Q, F, W, Y, P, or C; D182 replaced with H, K, R, A, G, I, L, S, T, M, V, N, Q, F, W, Y, P, or C; G183 replaced with D, E, H, K, R, N, Q, F, W, Y, P, or C; Q184 replaced with D, E, H, K, R, A, G, I, L, S, T, M, V, F, W, Y, P, or C; V185 replaced with D, E, H, K, R, N, Q, F, W, Y, P, or C; L186 replaced with D, E, H, K, R, N, Q, F, W, Y, P, or C; S187 replaced with D, E, H, K, R, N, Q, F, W, Y, P, or C; I188 replaced with D, E, H, K, R, N, Q, F, W, Y, P, or C; S189 replaced with D, E, H, K, R, N, Q, F, W, Y, P, or C; L190 replaced with D, E, H, K, R, N, Q, F, W, Y, P, or C; G191 replaced with D, E, H, K, R, N, Q, F, W, Y, P, or C; P192 replaced with D, E, H, K, R, A, G, I, L, S, T, M, V, N, Q, F, W, Y, or C; G193 replaced with D, E, H, K, R, N, Q, F, W, Y, P, or C; D194 replaced with H, K, R, A, G, I, L, S, T, M, V, N, Q, F, W, Y, P, or C; R195 replaced with D, E, A, G, I, L, S, T, M, V, N, Q, F, W, Y, P, or C; D196 replaced with H, K, R, A, G, I, L, S, T, M, V, N, Q, F, W, Y, P, or C; V197 replaced with D, E, H, K, R, N, Q, F, W, Y, P, or C; A198 replaced with D, E, H, K, R, N, Q, F, W, Y, P, or C; Y199 replaced with D, E, H, K, R, N, Q, A, G, I, L, S, T, M, V, P, or C; S200 replaced with D, E, H, K, R, N, Q, F, W, Y, P, or C; C201 replaced with D, E, H, K, R, A, G, I, L, S, T, M, V, N, Q, F, W, Y, or P; I202 replaced with D, E, H, K, R, N, Q, F, W, Y, P, or C; V203 replaced with D, E, H, K, R, N, Q, F, W, Y, P, or C; S204 replaced with D, E, H, K, R, N, Q, F, W, Y, P, or C; N205 replaced with D, E, H, K, R, A, G, I, L, S, T, M, V, F, W, Y, P, or C; P206 replaced with D, E, H, K, R, A, G, I, L, S, T, M, V, N, Q, F, W, Y, or C; V207 replaced with D, E, H, K, R, N, Q, F, W, Y, P, or C; S208 replaced with D, E, H, K, R, N, Q, F, W, Y, P, or C; W209 replaced with D, E, H, K, R, N, Q, A, G, I, L, S, T, M, V, P, or C; D210 replaced with H, K, R, A, G, I, L, S, T, M, V, N, Q, F, W, Y, P, or C; L211 replaced with D, E, H, K, R, N, Q, F, W, Y, P, or C; A212 replaced with D, E, H, K, R, N, Q, F, W, Y, P, or C; T213 replaced with D, E, H, K, R, N, Q, F, W, Y, P, or C; V214 replaced with D, E, H, K, R, N, Q, F, W, Y, P, or C; T215 replaced with D, E, H, K, R, N, Q, F, W, Y, P, or C; P216 replaced with D, E, H, K, R, A, G, I, L, S, T, M, V, N, Q, F, W, Y, or C; W217 replaced with D, E, H, K, R, N, Q, A, G, I, L, S, T, M, V, P, or C; D218 replaced with H, K, R, A, G, I, L, S, T, M, V, N, Q, F, W, Y, P, or C; S219 replaced with D, E, H, K, R, N, Q, F, W, Y, P, or C; C220 replaced with D, E, H, K, R, A, G, I, L, S, T, M, V, N, Q, F, W, Y, or P; H221 replaced with D, E, A, G, I, L, S, T, M, V, N, Q, F, W, Y, P, or C; H222 replaced with D, E, A, G, I, L, S, T, M, V, N, Q, F, W, Y, P, or C; E223 replaced with H, K, R, A, G, I, L, S, T, M, V, N, Q, F, W, Y, P, or C; A224 replaced with D, E, H, K, R, N, Q, F, W, Y, P, or C; A225 replaced with D, E, H, K, R, N, Q, F, W, Y, P, or C; P226 replaced with D, E, H, K, R, A, G, I, L, S, T, M, V, N, Q, F, W, Y, or C; G227 replaced with D, E, H, K, R, N, Q, F, W, Y, P, or C; K228 replaced with D, E, A, G, I, L, S, T, M, V, N, Q, F, W, Y, P, or C; A229 replaced with D, E, H, K, R, N, Q, F, W, Y, P, or C; S230 replaced with D, E, H, K, R, N, Q, F, W, Y, P, or C; Y231 replaced with D, E, H, K, R, N, Q, A, G, I, L, S, T, M, V, P, or C; K232 replaced with D, E, A, G, I, L, S, T, M, V, N, Q, F, W, Y, P, or C; D233 replaced with H, K, R, A, G, I, L, S, T, M, V, N, Q, F, W, Y, P, or C; V234 replaced with D, E, H, K, R, N, Q, F, W, Y, P, or C; L235 replaced with D, E, H, K, R, N, Q, F, W, Y, P, or C; L236 replaced with D, E, H, K, R, N, Q, F, W, Y, P, or C; V237 replaced with D, E, H, K, R, N, Q, F, W, Y, P, or C; V238 replaced with D, E, H, K, R, N, Q, F, W, Y, P, or C; V239 replaced with D, E, H, K, R, N, Q, F, W, Y, P, or C; P240 replaced with D, E, H, K, R, A, G, I, L, S, T, M, V, N, Q, F, W, Y, or C; V241 replaced with D, E, H, K, R, N, Q, F, W, Y, P, or C; S242 replaced with D, E, H, K, R, N, Q, F, W, Y, P, or C; L243 replaced with D, E, H, K, R, N, Q, F, W, Y, P, or C; L244 replaced with D, E, H, K, R, N, Q, F, W, Y, P, or C; L245 replaced with D, E, H, K, R, N, Q, F, W, Y, P, or C; M246 replaced with D, E, H, K, R, N, Q, F, W, Y, P, or C; L247 replaced with D, E, H, K, R, N, Q, F, W, Y, P, or C; V248 replaced with D, E, H, K, R, N, Q, F, W, Y, P, or C; T249 replaced with D, E, H, K, R, N, Q, F, W, Y, P, or C; L250 replaced with D, E, H, K, R, N, Q, F, W, Y, P, or C; F251 replaced with D, E, H, K, R, N, Q, A, G, I, L, S, T, M, V, P, or C; S252 replaced with D, E, H, K, R, N, Q, F, W, Y, P, or C; A253 replaced with D, E, H, K, R, N, Q, F, W, Y, P, or C; W254 replaced with D, E, H, K, R, N, Q, A, G, I, L, S, T, M, V, P, or C; H255 replaced with D, E, A, G, I, L, S, T, M, V, N, Q, F, W, Y, P, or C; W256 replaced with D, E, H, K, R, N, Q, A, G, I, L, S, T, M, V, P, or C; C257 replaced with D, E, H, K, R, A, G, I, L, S, T, M, V, N, Q, F, W, Y, or P; P258 replaced with D, E, H, K, R, A, G, I, L, S, T, M, V, N, Q, F, W, Y, or C; C259 replaced with D, E, H, K, R, A, G, I, L, S, T, M, V, N, Q, F, W, Y, or P; S260 replaced with D, E, H, K, R, N, Q, F, W, Y, P, or C; G261 replaced with D, E, H, K, R, N, Q, F, W, Y, P, or C; K262 replaced with D, E, A, G, I, L, S, T, M, V, N, Q, F, W, Y, P, or C; K263 replaced with D, E, A, G, I, L, S, T, M, V, N, Q, F, W, Y, P, or C; K264 replaced with D, E, A, G, I, L, S, T, M, V, N, Q, F, W, Y, P, or C; K265 replaced with D, E, A, G, I, L, S, T, M, V, N, Q, F, W, Y, P, or C; D266 replaced with H, K, R, A, G, I, L, S, T, M, V, N, Q, F, W, Y, P, or C; V267 replaced with D, E, H, K, R, N, Q, F, W, Y, P, or C; H268 replaced with D, E, A, G, I, L, S, T, M, V, N, Q, F, W, Y, P, or C; A269 replaced with D, E, H, K, R, N, Q, F, W, Y, P, or C; D270 replaced with H, K, R, A, G, I, L, S, T, M, V, N, Q, F, W, Y, P, or C; R271 replaced with D, E, A, G, I, L, S, T, M, V, N, Q, F, W, Y, P, or C; V272 replaced with D, E, H, K, R, N, Q, F, W, Y, P, or C; G273 replaced with D, E, H, K, R, N, Q, F, W, Y, P, or C; P274 replaced with D, E, H, K, R, A, G, I, L, S, T, M, V, N, Q, F, W, Y, or C; E275 replaced with H, K, R, A, G, I, L, S, T, M, V, N, Q, F, W, Y, P, or C; T276 replaced with D, E, H, K, R, N, Q, F, W, Y, P, or C; E277 replaced with H, K, R, A, G, I, L, S, T, M, V, N, Q, F, W, Y, P, or C; N278 replaced with D, E, H, K, R, A, G, I, L, S, T, M, V, F, W, Y, P, or C; P279 replaced with D, E, H, K, R, A, G, I, L, S, T, M, V, N, Q, F, W, Y, or C; L280 replaced with D, E, H, K, R, N, Q, F, W, Y, P, or C; V281 replaced with D, E, H, K, R, N, Q, F, W, Y, P, or C; Q282 replaced with D, E, H, K, R, A, G, I, L, S, T, M, V, F, W, Y, P, or C; D283 replaced with H, K, R, A, G, I, L, S, T, M, V, N, Q, F, W, Y, P, or C; L284 replaced with D, E, H, K, R, N, Q, F, W, Y, P, or C; P285 replaced with D, E, H, K, R, A, G, I, L, S, T, M, V, N, Q, F, W, Y, or C.

The resulting constructs can be routinely screened for activities or functions described throughout the specification and known in the art. Preferably, the resulting constructs have loss of a D-SLAM activity or function, while the remaining D-SLAM activities or functions are maintained. More preferably, the resulting constructs have more than one loss of D-SLAM activity or function, while the remaining D-SLAM activities or functions are maintained.

Additionally, more than one amino acid (e.g., 2, 3, 4, 5, 6, 7, 8, 9 and 10) can be replaced with the substituted amino acids as described above (either conservative or nonconservative).

A further embodiment of the invention relates to a polypeptide which comprises, or alternatively consists of, the amino acid sequence of a D-SLAM polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises, or alternatively consists of, the amino acid sequence of a D-SLAM polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A–1D or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is further directed to fragments of the isolated nucleic acid molecules described herein. By a fragment of an isolated nucleic acid molecule having, for example, the nucleotide sequence of the deposited cDNA (clone HDPJO39), a nucleotide sequence encoding the polypeptide sequence encoded by the deposited cDNA, a nucleotide sequence encoding the polypeptide sequence depicted in FIG. 1 (SEQ ID NO:2), the nucleotide sequence shown in FIG. 1 (SEQ ID NO:1), or the complementary strand thereto, is intended fragments at least 15 nt, and more preferably at least about 20 nt, still more preferably at least 30 nt, and even more preferably, at least about 40, 50, 100, 150, 200, 250, 300, 325, 350, 375, 400, 450, 500, 550, or 600 nt in length. These fragments have numerous uses that include, but are not limited to, diagnostic probes and primers as discussed herein. Of course, larger fragments, such as those of 501–1500 nt in length are also useful according to the present invention as are fragments corresponding to most, if not all, of the nucleotide sequences of the deposited cDNA (clone HDPJO39) or as shown in FIG. 1 (SEQ ID NO:1). By a fragment at least 20 nt in length, for example, is intended fragments which include 20 or more contiguous bases from, for example, the nucleotide sequence of the deposited cDNA, or the nucleotide sequence as shown in FIG. 1 (SEQ ID NO:1).

Moreover, representative examples of D-SLAM polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, and/or 2001 to the end of SEQ ID NO:1 or the complementary strand thereto, or the cDNA contained in the deposited clone. In this context "about" includes the particularly recited ranges, larger or smaller by several (5, 4, 3, 2, or 1) nucleotides, at either terminus or at both termini.

Preferably, the polynucleotide fragments of the invention encode a polypeptide which demonstrates a D-SLAM functional activity. By "a polypeptide demonstrating a D-SLAM functional activity" is intended polypeptides capable of exhibiting activity similar, but not necessarily identical, to a known functional activity of the D-SLAM polypeptides of the present invention (e.g., complete (full-length) D-SLAM, mature D-SLAM and soluble D-SLAM (e.g., having sequences contained in the extracellular domain of D-SLAM) as measured, for example, in a particular immunoassay or biological assay. Such functional activities include, but are not limited to, biological activity (e.g., ability to bind monocyte derived dendritic cells, ability to upregulate cell surface markers indicative of dendritic cell maturation or activation (such as, for example, HLA-DR, CD54, CD86, CD83), ability to inhibit B-cell proliferation, ability to inhibit BLyS induced cell proliferative activity), antigenicity (ability to bind or compete with a D-SLAM polypeptide for binding to an anti-D-SLAM antibody), immunogenicity (ability to generate antibody which binds to a D-SLAM polypeptide), ability to form multimers with D-SLAM polypeptides of the invention, ability to form heteromultimers, ability to bind to a receptor or ligand).

The functional activity of D-SLAM polypeptides, and fragments, variants derivatives, and analogs thereof, can be assayed by various methods.

For example, in one embodiment where one is assaying for the ability to bind or compete with full-length D-SLAM polypeptide for binding to anti-D-SLAM antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a D-SLAM ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of D-SLAM binding to its substrates (signal transduction) can be assayed.

In addition, assays described herein (see Examples) and otherwise known in the art may routinely be applied to measure the ability of D-SLAM polypeptides and fragments, variants derivatives and analogs thereof to elicit D-SLAM related biological activity (either in vitro or in vivo). Other methods will be known to the skilled artisan and are within the scope of the invention.

The present invention is further directed to fragments of the D-SLAM polypeptide described herein. By a fragment of an isolated the D-SLAM polypeptide, for example, encoded by the deposited cDNA (clone HDPJO39), the polypeptide sequence encoded by the deposited cDNA, the polypeptide sequence depicted in FIG. 1 (SEQ ID NO:2), is intended to encompass polypeptide fragments contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, 161–180, 181–200, 201–220, 221–240, 241–260, 261–280, or 281 to the end of the coding region. Moreover, polypeptide fragments can be at least 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Even if deletion of one or more amino acids from the N-terminus of a protein results in modification of loss of one or more biological functions of the protein, other functional activities (e.g., biological activities, ability to multimerize, ability to bind D-SLAM ligand) may still be retained. For example, the ability of shortened D-SLAM muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an D-SLAM mutein with a large number of deleted N-terminal amino acid residues may retain some biological or immunogenic activities. In fact, peptides composed of as few as six D-SLAM amino acid residues may often evoke an immune response.

Accordingly, polypeptide fragments include the secreted D-SLAM protein as well as the mature form. Further preferred polypeptide fragments include the secreted D-SLAM protein or the mature form having a continuous series of deleted residues from the amino or the carboxy terminus, or both. For example, any number of amino acids, ranging from 1–60, can be deleted from the amino terminus of either the secreted D-SLAM polypeptide or the mature form. Similarly, any number of amino acids, ranging from 1–30, can be deleted from the carboxy terminus of the secreted D-SLAM protein or mature form. Furthermore, any combination of the above amino and carboxy terminus deletions are preferred. Similarly, polynucleotide fragments encoding these D-SLAM polypeptide fragments are also preferred. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the D-SLAM polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Particularly, N-terminal deletions of the D-SLAM polypeptide can be described by the general formula m-285, where m is an integer from 2 to 280, where m corresponds to the position of the amino acid residue identified in SEQ ID NO:2. More in particular, the invention provides polynucleotides encoding polypeptides comprising, or alternatively consisting of, an amino acid sequence selected from the group consisting of residues V-2 to P-285; M-3 to P-285; R-4 to P-285; P-5 to P-285; L-6 to P-285; W-7 to P-285; S-8 to P-285; L-9 to P-285; L-10 to P-285; L-11 to P-285; W-12 to P-285; E-13 to P-285; A-14 to P-285; L-15 to P-285; L-16 to P-285; P-17 to P-285; I-18 to P-285; T-19 to P-285; V-20 to P-285; T-21 to P-285; G-22 to P-285; A-23 to P-285; Q-24 to P-285; V-25 to P-285; L-26 to P-285; S-27 to P-285; K-28 to P-285; V-29 to P-285; G-30 to P-285; G-31 to P-285; S-32 to P-285; V-33 to P-285; L-34 to P-285; L-35 to P-285; V-36 to P-285; A-37 to P-285; A-38 to P-285; R-39 to P-285; P-40 to P-285; P-41 to P-285; G-42 to P-285; F-43 to P-285; Q-44 to P-285; V-45 to P-285; R-46 to P-285; E-47 to P-285; A-48 to P-285; I-49 to P-285; W-50 to P-285; R-51 to P-285; S-52 to P-285; L-53 to P-285; W-54 to P-285; P-55 to P-285; S-56 to P-285; E-57 to P-285; E-58 to P-285; L-59 to P-285; L-60 to P-285; A-61 to P-285; T-62 to P-285; F-63 to P-285; F-64 to P-285; R-65 to P-285; G-66 to P-285; S-67 to P-285; L-68 to P-285; E-69 to P-285; T-70 to P-285; L-71 to P-285; Y-72 to P-285; H-73 to P-285; S-74 to P-285; R-75 to P-285; F-76 to P-285; L-77 to P-285; G-78 to P-285; R-79 to P-285; A-80 to P-285; Q-81 to P-285; L-82 to P-285; H-83 to P-285; S-84 to P-285; N-85 to P-285; L-86 to P-285; S-87 to P-285; L-88 to P-285; E-89 to P-285; L-90 to P-285; G-91 to P-285; P-92 to P-285; L-93 to P-285; E-94 to P-285; S-95 to P-285; G-96 to P-285; D-97 to P-285; S-98 to P-285; G-99 to P-285; N-100 to P-285; F-101 to P-285; S-102 to P-285; V-103 to P-285; L-104 to P-285; M-105 to P-285; V-106 to P-285; D-107 to P-285; T-108 to P-285; R-109 to P-285; G-110 to P-285; Q-111 to P-285; P-112 to P-285; W-113 to P-285; T-114 to P-285; Q-115 to P-285; T-116 to P-285; L-117 to P-285; Q-118 to P-285; L-119 to P-285; K-120 to P-285; V-121 to P-285; Y-122 to P-285; D-123 to P-285; A-124 to P-285; V-125 to P-285; P-126 to P-285; R-127 to P-285; P-128 to P-285; V-129 to P-285; V-130 to P-285; Q-131 to P-285; V-132 to P-285; F-133 to P-285; I-134 to P-285; A-135 to P-285; V-136 to P-285; E-137 to P-285; R-138 to P-285; D-139 to P-285; A-140 to P-285; Q-141 to P-285; P-142 to P-285; S-143 to P-285; K-144 to P-285; T-145 to P-285; C-146 to P-285; Q-147 to P-285; V-148 to P-285; F-149 to P-285; L-150 to P-285; S-151 to P-285; C-152 to P-285; W-153 to P-285; A-154 to P-285; P-155 to P-285; N-156 to P-285; I-157 to P-285; S-158 to P-285; E-159 to P-285; I-160 to P-285; T-161 to P-285; Y-162 to P-285; S-163 to P-285; W-164 to P-285; R-165 to P-285; R-166 to P-285; E-167 to P-285; T-168 to P-285; T-169 to P-285; M-170 to P-285; D-171 to P-285; F-172 to P-285; G-173 to P-285; M-174 to P-285; E-175 to P-285; P-176 to P-285; H-177 to P-285; S-178 to P-285; L-179 to P-285; F-180 to P-285; T-181 to P-285; D-182 to P-285; G-183 to P-285; Q-184 to P-285; V-185 to P-285; L-186 to P-285; S-187 to P-285; I-188 to P-285; S-189 to P-285; L-190 to P-285; G-191 to P-285; P-192 to P-285; G-193 to P-285; D-194 to P-285; R-195 to P-285; D-196 to P-285; V-197 to P-285; A-198 to P-285; Y-199 to P-285; S-200 to P-285; C-201 to P-285; I-202 to P-285; V-203 to P-285; S-204 to P-285; N-205 to P-285; P-206 to P-285; V-207 to P-285; S-208 to P-285; W-209 to P-285; D-210 to P-285; L-211 to P-285; A-212 to P-285; T-213 to P-285; V-214 to P-285; T-215 to P-285; P-216 to P-285; W-217 to P-285; D-218 to P-285; S-219 to P-285; C-220 to P-285; H-221 to P-285; H-222 to P-285; E-223 to P-285; A-224 to P-285; A-225 to P-285; P-226 to P-285; G-227 to P-285; K-228 to P-285; A-229 to P-285; S-230 to P-285; Y-231 to P-285; K-232 to P-285; D-233 to P-285; V-234 to P-285; L-235 to P-285; L-236 to P-285; V-237 to P-285; V-238 to P-285; V-239 to P-285; P-240 to P-285; V-241 to P-285; S-242 to P-285; L-243 to P-285; L-244 to P-285; L-245 to P-285; M-246 to P-285; L-247 to P-285; V-248 to P-285; T-249 to P-285; L-250 to P-285; F-251 to P-285; S-252 to P-285; A-253 to P-285; W-254 to P-285; H-255 to P-285; W-256 to P-285; C-257 to P-285; P-258 to P-285; C-259 to P-285; S-260 to P-285; G-261 to P-285; K-262 to P-285; K-263 to P-285; K-264 to P-285; K-265 to P-285; D-266 to P-285; V-267 to P-285; H-268 to P-285; A-269 to P-285; D-270 to P-285; R-271 to P-285; V-272 to P-285; G-273 to P-285; P-274 to P-285; E-275 to P-285; T-276 to P-285; E-277 to P-285; N-278 to P-285; P-285; P-279 to P-285; and L-280 to P-285 of SEQ ID NO:2.

Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the D-SLAM polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Also as mentioned above, even if deletion of one or more amino acids from the C-terminus of a protein results in modification of loss of one or more biological functions of the protein, other functional activities (e.g., biological activities, ability to multimerize, ability to bind D-SLAM ligand) may still be retained. For example the ability of the shortened D-SLAM mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an D-SLAM mutein with a large number of deleted C-terminal amino acid residues may retain some biological or immunogenic activities. In fact, peptides composed of as few as six D-SLAM amino acid residues may often evoke an immune response.

Accordingly, the present invention further provides polypeptides having one or more residues deleted from the carboxy terminus of the amino acid sequence of the D-SLAM polypeptide shown in FIG. 1 (SEQ ID NO:2), as described by the general formula 1–n, where n is an integer from 7 to 284, where n corresponds to the position of amino acid residue identified in SEQ ID NO:2. More in particular, the invention provides polynucleotides encoding polypeptides comprising, or alternatively consisting of, an amino acid sequence selected from the group consisting of residues M-1 to L-284; M-1 to D-283; M-1 to Q-282; M-1 to V-281; M-1 to L-280; M-1 to P-279; M-1 to N-278; M-1 to E-277; M-1 to T-276; M-1 to E-275; M-1 to P-274; M-1 to G-273; M-1 to V-272; M-1 to R-271; M-1 to D-270; M-1 to A-269; M-1 to H-268; M-1 to V-267; M-1 to D-266; M-1 to K-265; M-1 to K-264; M-1 to K-263; M-1 to K-262; M-1 to G-261; M-1 to S-260; M-1 to C-259; M-1 to P-258; M-1 to C-257; M-1 to W-256; M-1 to H-255; M-1 to W-254; M-1 to A-253; M-1 to S-252; M-1 to F-251; M-1 to L-250; M-1 to T-249; M-1 to V-248; M-1 to L-247; M-1 to M-246; M-1 to L-245; M-1 to L-244; M-1 to L-243; M-1 to S-242; M-1 to V-241; M-1 to P-240; M-1 to V-239; M-1 to V-238; M-1 to V-237; M-1 to L-236; M-1 to L-235; M-1 to V-234; M-1 to D-233; M-1 to K-232; M-1 to Y-231; M-1 to S-230; M-1 to A-229; M-1 to K-228; M-1 to G-227; M-1 to P-226; M-1 to A-225; M-1 to A-224; M-1 to E-223; M-1 to H-222; M-1 to H-221; M-1 to C-220; M-1 to S-219; M-1 to D-218; M-1 to W-217; M-1 to P-216; M-1 T-215; M-1 to V-214; M-1 to T-213; M-1 to A-212; M-1 to L-211; M-1 to D-210; M-1 to W-209; M-1 to S-208; M-1 to V-207; M-1 to P-206; M-1 to N-205; M-1 to S-204; M-1 to V-203; M-1 to I-202; M-1 to C-201; M-1 to S-200; M-1 to Y-199; M-1 to A-198; M-1 to V-197; M-1 to D-196; M-1 to R-195; M-1 to D-194; M-1 to G-193; M-1 to P-192; M-1 to G-191; M-1 to L-190; M-1 to S-189; M-1 to I-188; M-1 to S-187; M-1 to L-186; M-1 to V-185; M-1 to Q-184; M-1 to G-183; M-1 to D-182; M-1 to T-181; M-1 to F-180; M-1 to L-179; M-1 to S-178; M-1 to H-177; M-1 to P-176; M-1 to E-175; M-1 to M-174; M-1 to G-173; M-1 to F-172; M-1 to D-171; M-1 to M-170; M-1 to T-169; M-1 to T-168; M-1 to E-167; M-1 to R-166; M-1 to R-165; M-1 to W-164; M-1 to S-163; M-1 to Y-162; M-1 to T-161; M-1 to I-160; M-1 to E-159; M-1 to S-158; M-1 to I-157; M-1 to N-156; M-1 to P-155; M-1 to A-154; M-1 to W-153; M-1 to C-152; M-1 to S-151; M-1 to L-150; M-1 to F-149; M-1 to V-148; M-1 to Q-147; M-1 to C-146; M-1 to T-145; M-1 to K-144; M-1 to S-143; M-1 to P-142; M-1 to Q-141; M-1 to A-140; M-1 to D-139; M-1 to R-138; M-1 to E-137; M-1 to V-136; M-1 to A-135; M-1 to I-134; M-1 to F-133; M-1 to V-132; M-1 to Q-131; M-1 to V-130; M-1 to V-129; M-1 to P-128; M-1 to R-127; M-1 to P-126; M-1 to V-125; M-1 to A-124; M-1 to D-123; M-1 to Y-122; M-1 to V-121; M-1 to K-120; M-1 to L-119; M-1 to Q-118; M-1 to L-117; M-1 to T-116; M-1 to Q-115; M-1 to T-114; M-1 to W-113; M-1 to P-112; M-1 to Q-111; M-1 to G-110; M-1 to R-109; M-1 to T-108; M-1 to D-107; M-1 to V-106; M-1 to M-105; M-1 to L-104; M-1 to V-103; M-1 to S-102; M-1 to F-101; M-1 to N-100; M-1 to G-99; M-1 to S-98; M-1 to D-97; M-1 to G-96; M-1 to S-95; M-1 to E-94; M-1 to L-93; M-1 to P-92; M-1 to G-91; M-1 to L-90; M-1 to E-89; M-1 to L-88; M-1 to S-87; M-1 to L-86; M-1 to N-85; M-1 to S-84; M-1 to H-83; M-1 to L-82; M-1 to Q-81; M-1 to A-80; M-1 to R-79; M-1 to G-78; M-1 to L-77; M-1 to F-76; M-1 to R-75; M-1 to S-74; M-1 to H-73; M-1 to Y-72; M-1 to L-71; M-1 to T-70; M-1 to E-69; M-1 to L-68; M-1 to S-67; M-1 to G-66; M-1 to R-65; M-1 to F-64; M-1 to F-63; M-1 to T-62; M-1 to A-61; M-1 to L-60; M-1 to L-59; M-1 to E-58; M-1 to E-57; M-1 to S-56; M-1 to P-55; M-1 to W-54; M-1 to L-53; M-1 to S-52; M-1 to R-51; M-1 to W-50; M-1 to I-49; M-1 to A-48; M-1 to E47; M-1 to R-46; M-1 to V-45; M-1 to Q-44; M-1 to F-43; M-1 to G-42; M-1 to P-41; M-1 to P-40; M-1 to R-39; M-1 to A-38; M-1 to A-37; M-1 to V-36; M-1 to L-35; M-1 to L-34; M-1 to V-33; M-1 to S-32; M-1 to G-31; M-1 to G-30; M-1 to V-29; M-1 to K-28; M-1 to S-27; M-1 to L-26; M-1 to V-25; M-1 to Q-24; M-1 to A-23; M-1 to G-22; M-1 to T-21; M-1 to V-20; M-1 to T-19; M-1 to I-18; M-1 to P-17; M-1 to L-16; M-1 to L-15; M-1 to A-14; M-1 to E-13; M-1 to W-12; M-1 to L-11; M-1 to L-10; M-1 to L-9; M-1 to S-8; and M-1 to W-7 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the D-SLAM polypeptides described above. The present invention also encompasses the above polynucleotide sequences fused to a heterologous polynucleotide sequence. Polypeplides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

In addition, any of the above listed N- or C-terminal deletions can be combined to produce a N- and C-terminal deleted D-SLAM polypeptide. The invention also provides polypeptides having one or more amino acids deleted from both the amino and the carboxyl termini, which may be described generally as having residues m-n of SEQ ID NO:2, where n and m are integers as described above. Polynucleotides encoding these polypeptides are also encompassed by the invention.

Moreover, preferred N- and C-terminal deletion mutants comprise, or in the alternative consist of, the predicted secreted form of D-SLAM. Preferred secreted forms of the D-SLAM include polypeptides comprising, or alternatively consisting of, an amino acid sequence selected from the group consisting of residues M-1 to K-232; V-2 to K-232; M-3 to K-232; R-4 to K-232; P-5 to K-232; L-6 to K-232; W-7 to K-232; S-8 to K-232; L-9 to K-232; L-10 to K-232; L-11 to K-232; W-12 to K-232; E-13 to K-232; A-14 to K-232; L-15 to K-232; L-16 to K-232; P-17 to K-232; I-18 to K-232; T-19 to K-232; V-20 to K-232; T-21 to K-232; G-22 to K-232; A-23 to K-232; Q-24 to K-232; V-25 to K-232; L-26 to K-232; S-27 to K-232; K-28 to K-232; V-29 to K-232; G-30 to K-232; G-31 to K-232; S-32 to K-232; V-33 to K-232; L-34 to K-232; L-35 to K-232; V-36 to K-232; A-37 to K-232; A-38 to K-232; R-39 to K-232; P-40 to K-232; P-41 to K-232; G-42 to K-232; F-43 to K-232; Q-44 to K-232; V-45 to K-232; R-46 to K-232; E-47 to K-232; A-48 to K-232; I-49 to K-232; W-50 to K-232; R-51 to K-232; S-52 to K-232; L-53 to K-232; W-54 to K-232; P-55 to K-232; S-56 to K-232; E-57 to K-232; E-58 to K-232; L-59 to K-232; L-60 to K-232; A-61 to K-232; T-62 to K-232; F-63 to K-232; F-64 to K-232; R-65 to K-232; G-66 to K-232; S-67 to K-232; L-68 to K-232; E-69 to K-232; T-70 to K-232; L-71 to K-232; Y-72 to K-232; H-73 to K-232; S-74 to K-232; R-75 to K-232; F-76 to K-232; L-77 to K-232; G-78 to K-232; R-79 to K-232; A-80 to K-232; Q-81 to K-232; L-82 to K-232; H-83 to K-232; S-84 to K-232; N-85 to K-232; L-86 to K-232; S-87 to K-232; L-88 to K-232; E-89 to K-232; L-90 to K-232; G-91 to K-232; P-92 to K-232; L-93 to K-232; E-94 to K-232; S-95 to K-232; G-96 to K-232; D-97 to K-232; S-98 to K-232; G-99 to K-232; N-100 to K-232; F-101 to K-232; S-102 to K-232; V-103 to K-232; L-104 to K-232; M-105 to K-232; V-106 to K-232; D-107 to K-232; T-108 to K-232; R-109 to K-232; G-110 to K-232; Q-111 to K-232; P-112 to K-232; W-113 to K-232; T-114 to K-232; Q-115 to K-232; T-116 to K-232; L-117 to K-232; Q-118 to K-232; L-119 to K-232; K-120 to K-232; V-121 to K-232; Y-122 to K-232; D-123 to K-232; A-124 to K-232; V-125 to K-232; P-126 to K-232; R-127 to K-232; P-128 to K-232; V-129 to K-232; V-130 to K-232; Q-131 to K-232; V-132 to K-232; F-133 to K-232; I-134 to K-232; A-135 to K-232; V-136 to K-232; E-137 to K-232; R-138 to K-232; D-139 to K-232; A-140 to K-232; Q-141 to K-232; P-142 to K-232; S-143 to K-232; K-144 to K-232; T-145 to K-232; C-146 to K-232; Q-147 to K-232; V-148 to K-232; F-149 to K-232; L-150 to K-232; S-151 to K-232; C-152 to K-232; W-153 to K-232; A-154 to K-232; P-155 to K-232; N-156 to K-232; I-157 to K-232; S-158 to K-232; E-159 to K-232; I-160 to K-232; T-161 to K-232; Y-162 to K-232; S-163 to K-232; W-164 to K-232; R-165 to K-232; R-166 to K-232; E-167 to K-232; T-168 to K-232; T-169 to K-232; M-170 to K-232; D-171 to K-232; F-172 to K-232; G-173 to K-232; M-174 to K-232; E-175 to K-232; P-176 to K-232; H-177 to K-232; S-178 to K-232; L-179 to K-232; F-180 to K-232; T-181 to K-232; D-182 to K-232; G-183 to K-232; Q-184 to K-232; V-185 to K-232; L-186 to K-232; S-187 to K-232; I-188 to K-232; S-189 to K-232; L-190 to K-232; G-191 to K-232; P-192 to K-232; G-193 to K-232; D-194 to K-232; R-195 to K-232; D-196 to K-232; V-197 to K-232; A-198 to K-232; Y-199 to K-232; S-200 to K-232; C-201 to K-232; I-202 to K-232; V-203 to K-232;

S-204 to K-232; N-205 to K-232; P-206 to K-232; V-207 to K-232; S-208 to K-232; W-209 to K-232, D-210 to K-232; L-211 to K-232; A-212 to K-232; T-213 to K-232; V-214 to K-232; T-215 to K-232; P-216 to K-232; W-217 to K-232; D-218 to K-232; S-219 to K-232; C-220 to K-232; H-221 to K-232; H-222 to K-232; E-223 to K-232; A-224 to K-232; A-225 to K-232; P-226 to K-232; and G-227 to K-232 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the D-SLAM polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Additionally, preferred N- and C-terminal deletion mutants comprise, or in the alternative consist of, fragments lacking the predicted signal sequence of D-SLAM. Preferred fragments of D-SLAM include polypeptides comprising, or alternatively consisting of, an amino acid sequence selected from the group consisting of residues A-23 to L-284; A-23 to D-283; A-23 to Q-282; A-23 to V-281; A-23 to L-280; A-23 to P-279; A-23 to N-278; A-23 to E-277; A-23 to T-276; A-23 to E-275; A-23 to P-274; A-23 to G-273; A-23 to V-272; A-23 to R-271; A-23 to D-270; A-23 to A-269; A-23 to H-268; A-23 to V-267; A-23 to D-266; A-23 to K-265; A-23 to K-264; A-23 to K-263; A-23 to K-262; A-23 to G-261; A-23 to S-260; A-23 to C-259; A-23 to P-258; A-23 to C-257; A-23 to W-256; A-23 to H-255; A-23 to W-254; A-23 to A-253; A-23 to S-252; A-23 to F-251; A-23 to L-250; A-23 to T-249; A-23 to V-248; A-23 to L-247; A-23 to M-246; A-23 to L-245; A-23 to L-244; A-23 to L-243; A-23 to S-242; A-23 to V-241; A-23 to P-240; A-23 to V-239; A-23 to V-238; A-23 to V-237; A-23 to L-236; A-23 to L-235; A-23 to V-234; A-23 to D-233; A-23 to K-232; A-23 to Y-231; A-23 to S-230; A-23 to A-229; A-23 to K-228; A-23 to G-227; A-23 to P-226; A-23 to A-225; A-23 to A-224; A-23 to E-223; A-23 to H-222; A-23 to H-221; A-23 to C-220; A-23 to S-219; A-23 to D-218; A-23 to W-217; A-23 to P-216; A-23 to T-215; A-23 to V-214; A-23 to T-213; A-23 to A-212; A-23 to L-211; A-23 to D-210; A-23 to W-209; A-23 to S-208; A-23 to V-207; A-23 to P-206; A-23 to N -205; A -23 to S-204; A-23 to V-203; A-23 to I-202; A-23 to C-201; A-23 to S-200; A-23 to Y-199; A-23 to A-198; A-23 to V-197; A-23 to D-196; A-23 to R-195; A-23 to D-194; A-23 to G-193; A-23 to P-192; A-23 to G-191; A-23 to L-190; A-23 to S-189; A-23 to I-188; A-23 to S-187; A-23 to L-186; A-23 to V-185; A-23 to Q-184; A-23 to G-183; A-23 to D-182; A-23 to T-181; A-23 to F-180; A-23 to L-179; A-23 to S-178; A-23 to H-177; A-23 to P-176; A-23 to E-175; A-23 to M-174; A-23 to G-173; A-23 to F-172; A-23 to D-171; A-23 to M-170; A-23 to T-169; A-23 to T-168; A-23 to E-167; A-23 to R-166; A-23 to R-165; A-23 to W-164; A-23 to S-163; A-23 to Y-162; A-23 to T-161; A-23 to I-160; A-23 to E-159; A-23 to S-158; A-23 to I-157; A-23 to N-156; A-23 to P-155; A-23 to A-154; A-23 to W-153; A-23 to C-152; A-23 to S-151; A-23 to L-150; A-23 to F-149; A-23 to V-148; A-23 to Q-147; A-23 to C-146; A-23 to T-145; A-23 to K-144; A-23 to S-143; A-23 to P-142; A-23 to Q-141; A-23 to A-140; A-23 to D-139; A-23 to R-138; A-23 to E-137; A-23 to V-136; A-23 to A-135; A-23 to I-134; A-23 to F-133; A-23 to V-132; A-23 to Q-131; A-23 to V-130; A-23 to V-129; A-23 to P-128; A-23 to R-127; A-23 to P-126; A-23 to V-125; A-23 to A-124; A-23 to D-123; A-23 to Y-122; A-23 to V-121; A-23 to K-120; A-23 to L-119; A-23 to Q-118; A-23 to L-117; A-23 to T-116; A-23 to Q-115; A-23 to T-114; A-23 to W-113; A-23 to P-112; A-23 to Q-111; A-23 to G-110; A-23 to R-109; A-23 to T-108; A-23 to D-107; A-23 to V-106; A-23 to M-105; A-23 to L-104; A-23 to V-103; A-23 to S-102; A-23 to F-101; A-23 to N-100; A-23 to G-99; A-23 to S-98; A-23 to D-97; A-23 to G-96; A-23 to S-95; A-23 to E-94; A-23 to L-93; A-23 to P-92; A-23 to G-91; A-23 to L-90; A-23 to E-89; A-23 to L-88; A-23 to S-87; A-23 to L-86; A-23 to N-85; A-23 to S-84; A-23 to H-83; A-23 to L-82; A-23 to Q-81; A-23 to A-80; A-23 to R-79; A-23 to G-78; A-23 to L-77; A-23 to F-76; A-23 to R-75; A-23 to S-74; A-23 to H-73; A-23 to Y-72; A-23 to L-71; A-23 to T-70; A-23 to E-69; A-23 to L-68; A-23 to S-67; A-23 to G-66; A-23 tp R-65; A-23 to F-64; A-23 to F-63; A-23 to T-62; A-23 to A-61; A-23 to L-60; A-23 to L-59; A-23 to E-58; A-23 to E-57; A-23 to S-56; A-23 to P-55; A-23 to W-54; A-23 to L-53; A-23 tp S-52; A-23 to R-51; A-23 to W-50; A-23 to I-49; A-23 to A-48; A-23 to E-47; A-23 to R-46; A-23 to V-45; A-23 to Q-44; A-23 to F-43; A-23 to G-42; A-23 to P-41; A-23 to P-40; A-23 to R-39; A-23 to A-38; A-23 to A-37; A-23 to V-36; A-23 to L-35; A-23 to L-34; A-23 to V-33; A-23 to S-32; A-23 to G-31; A-23 to G-30; and A-23 to V-29 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the D-SLAM polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

The present application is also directed to proteins containing polypeptides at least 80%, 85%, 90%, 92%, 95%, 96%, 97%, 98% or 99% identical to the D-SLAM polypeptide sequence set forth herein m-n. In preferred embodiments, the application is directed to proteins containing polypeptides at least 80%, 85%, 90%, 92%, 95%, 96%, 97%, 98% or 99% identical to polypeptides having the amino acid sequence of the specific D-SLAM N- and C-terminal deletions recited herein. Polynucleotides encoded by these polypeptides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequence encoding the D-SLAM polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98% or 99% identical to the amino acid sequence described above, and polynucleotides that encode such polypeptides.

Among the especially preferred fragments of the invention are fragments characterized by structural or functional attributes of D-SLAM. Such fragments include amino acid residues that comprise, or alternatively consist of, alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) D-SLAM (SEQ ID NO:2). Certain preferred regions are those set out in FIG. 3 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of D-SLAM. Preferred embodiments of the invention in this regard include fragments that comprise, or alternatively consist of, alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of D-SLAM.

The data representing the structural or functional attributes of D-SLAM set forth in FIG. 1 and/or Table I, as described above, was generated using the various modules and algorithms of the DNA*STAR set on default parameters. In a preferred embodiment, the data presented in columns VIII, IX, XIII, and XIV of Table I can be used to determine regions of D-SLAM which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIG. 1. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Among highly preferred fragments in this regard are those that comprise, or alternatively consist of, regions of D-SLAM that combine several structural features, such as several of the features set out in Table 1.

Other preferred fragments are biologically active D-SLAM fragments. Biologically active fragments are those exhibiting activity similar, but not necessarily identical, to an activity of the D-SLAM polypeptide. The biological activity of the fragments may include an improved desired activity, or a decreased undesirable activity.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. For example, the following ESTs are preferably excluded from the present invention: AA917335; AI094818, AI298413; N62522; AA627522; R11635; AA320408; AA379112; R09841; Z20320; N79421; D45800; T98959; AA217290; N30197; AA286132; and AA633983 (hereby incorporated by reference in their entirety.) However, to list every related sequence would be cumbersome. Accordingly, preferably excluded from the present invention are one or more polynucleotides comprising, or alternatively consisting of, a nucleotide sequence described by the general formula of a–b, where a is any integer between 1 to 3206 of SEQ ID NO:1, b is an integer of 15 to 3220, where both a and b correspond to the positions of nucleotide residues shown in SEQ ID NO:1, and where the b is greater than or equal to a+14.

Epitope-Bearing Portions

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in deposited clone HDPJO39 (ATCC Deposit No. 209623) or encoded by a polynucleotide that hybridizes to the complement of the sequence of SEQ ID NO:1 or contained in deposited clone HDPJO39 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). In one embodiment, a preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Epitope bearing peptides of the invention may also be synthesized as multiple antigen peptides (MAPs). MAPs consist of multiple copies of a specific peptide attached to a non-immunogenic lysine core. By way of non-limiting example, MAPs may be synthesized onto a lysine core matrix attached to a polyethylene glycol-polystyrene (PEG-PS) support. The peptide of choice is synthesized onto the lysine residues using 9-fluorenylmethoxycarbonyl (Fmoc) chemistry. For example, PerSeptive Biosystems (Foster City, Calif.) offers MAPs supports such as the ([Fmoc-Lys (Aloc)]$_4$-[Lys]$_2$-Lys-Ala-PAl-PEG-PS) support which can be used to synthesize MAPs. Cleavage of MAPs from the resin is performed with standard trifloroacetic acid (TFA)-based cocktails. Purification of MAPs, except for desalting, is not necessary.

As one of skill in the art will appreciate, and as discussed above, the polypeptides of the present invention (e.g., those comprising an immunogenic or antigenic epitope) can be fused to heterologous polypeptide sequences. For example, the polypeptides of the present invention (including fragments or variants thereof), may be fused with the constant domain of immunoglobulins (IgA, IgE, IgG, IgM), or portions thereof (CH1, CH2, CH3, or any combination thereof and portions thereof) resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1–z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins (as those described above) may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins may have both a heavy and light chain. An array of IgG, IgE, IgM, IgD, IgA, and IgY heavy chains may be paired with a light chain of the kappa or lambda forms. In a specific embodiment, the immunoglobulin molecules of the invention are IgG1. In another specific embodiment, the immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: binge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

In preferred, nonexclusive embodiments, the antibodies of the invention inhibit one or more biological activities of D-SLAM polypeptides of the invention through specific binding. In more preferred embodiments, the antibody of the invention inhibits D-SLAM-mediated inhibition of B cell proliferation. In additional preferred embodiments, the antibody of the invention stimulates B cell proliferation. In additional preferred embodiments, the antibody of the invention is used in combination with one or more additional antibodies and/or polypeptides and/or other agents to regulate B cell proliferation and/or biological phenomena related thereto.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15):3209–3214 (1998); Yoon et al., J. Immunol. 160(7):3170–3179 (1998); Prat et al., J. Cell. Sci. 111(Pt2):237–247 (1998); Pitard et al., J. Immunol. Methods 205(2):177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art and are discussed in detail in the Examples (e.g., Example 11). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5) :489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli,* and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (E.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalent and non-covalent conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), CD40 Ligand, a thrombotic agent or an anti-angiogenic agent, e.g., angiostatin, endostatin or VEGI (See, International Publication No. WO 99/23105); or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

In specific embodiments, D-SLAM binding polypetides of the invention are attached either directly or indirectly, to macrocyclic chelators useful for chelating radiometal ions, including but not limited to $^{177}$Lu, $^{90}$Y, $^{166}$Ho, and $^{153}$Sm, to polypeptides. In a preferred embodiment, the radiometal ion associated with the macrocyclic chelators attached to D-SLAM polypeptides of the invention is $^{111}$In. In another preferred embodiment, the radiometal ion associated with the macrocyclic chelator attached to D-SLAM polypeptides of the invention is $^{90}$Y. In specific embodiments, the macrocyclic chelator is 1,4,7,10-tetraazacyclododecane-N,N', N'',N'''-tetraacetic acid (DOTA). In one embodiment the side chain moiety of one or more classical or non-classical amino acids in a D-SLAM binding polypeptide comprises a DOTA molecule. In other specific embodiments, the DOTA is attached to the D-SLAM binding polypeptide of the invention via a linker molecule. Examples of linker molecules useful for conjugating DOTA to a polypeptide are commonly known in the art—see, for example, DeNardo et al., Clin. Cancer Res., 4(10):2483–90 (1998); Peterson et al., Bioconjug. Chem., 10(4):553–7 (1999); and Zimmerman et al, Nucl. Med. Biol., 26(8):943–50 (1999), which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the methods disclosed therein in order to conjugate chelating agents to other polypeptides.

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used, include but are not limited to, competitive and non-competitive assay systems using techniques such as western blots, radioimunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4 C, adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipilate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein (e.g., autoimmune diseases, disorders, or conditions associated with such diseases or disorders, including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders).

in a specific embodiment, antibodies of the invention are be used to treat, inhibit, prognoses diagnose or prevent rheumatoid arthritis.

In another specific embodiment, antibodies of the invention are used to treat, inhibit, prognose, diagnose or prevent systemic lupus erythematosus.

The treatment and/or prevention of diseases, disorders, or conditions associated with aberrant expression and/or activity of a polypeptide of the invention includes, but is not limited to, alleviating symptoms associated with those diseases, disorders or conditions. The antibodies of the invention may also be used to target and kill cells expressing D-SLAM on their surface and/or cells having D-SLAM bound to their surface. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, antibiotics, and immunoglobulin). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5): 155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred embodiment, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contain nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Clin., Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic and/or Prophylactic Administration and Composition

The invention provides methods of treatment, inhibition and prophylaxis by administration to a subject of an effective amount of a compound or pharmaceutical composition of the invention, preferably an antibody of the invention. In a preferred embodiment, the compound is substantially purified (e.g., substantially free from substances that limit its effect or produce undesired side effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum (99Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One embodiment of the invention is the detection and diagnosis of a disease or disorder associated with aberrant expression of a polypeptide of interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to the polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest.

Background level can be determined by various methods including, comparing the amount of labeled molecule detected to a standard value previously determined for a particular system. As described herein, specific embodiments of the invention are directed to the use of the antibodies of the invention to quantitate or qualitate concentrations of cells of B cell lineage or cells of monocytic lineage.

Also as described herein, antibodies of the invention may be used to treat, diagnose, or prognose an individual having an immunodeficiency. In a specific embodiment, antibodies of the invention are used to treat, diagnose, and/or prognose an individual having common variable immunodeficiency disease (CVD) or a subset of this disease. In another embodiment, antibodies of the invention are used to diagnose, prognose, treat or prevent a disorder characterized by deficient serium immunoglobulin production, recurrent infections, and/or immune system dysfunction.

Also as described herein, antibodies of the invention may be used to treat, diagnose, or prognose an individual having an autoimmune disease or disorder. In a specific embodiment, antibodies of the invention are used to treat, diagnose, and/or prognose an individual having systemic lupus erythematosus, or a subset of the disease. In another specific embodiment, antibodies of the invention are used to treat, diagnose and/or prognose an individual having rheumatoid arthritis, or a subset of this disease.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of the polypeptide of the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. Further included are antibodies that bind to D-SLAM irrespective of whether D-SLAM is bound to a D-SLAM Receptor. These antibodies act as D-SLAM agonists as reflected in an decrease in cellular proliferation in response to binding of D-SLAM to a D-SLAM receptor in the presence of these antibodies. The above antibody agonists can be made using methods known in the art. See e.g., WO 96/40281; U.S. Pat. No. 5,811,097; Deng, B. et al., Blood 92(6):1981–1988 (1998); Chen, Z. et al., Cancer Res. 58(16):3668–3678 (1998); Harrop, J. A. et al., J. Immunol. 161(4):1786–1794 (1998); Zhu, Z. et al., Cancer Res. 58(15):3209–3214 (1998); Yoon, D. Y. et al., J. Immunol. 160(7):3170–3179 (1998); Prat, M. et al., J. Cell. Sci. 111(Pt2):237–247 (1998); Pitard, V. et al., J. Immunol. Methods 205(2):177–190 (1997); Liautard, J. et al., Cytokine 9(4):233–241 (1997); Carlson, N. G. et al., J. Biol. Chem. 272(17):11295–11301 (1997); Taryman, R. E. et al., Neuron 14(4):755–762 (1995); Muller, Y. A. et al., Structure 6(9):1153–1167 (1998); Bartunek, P. et al., Cytokine 8(1): 14–20 (1996) (said references incorporated by reference in their entireties).

The invention encompasses antibodies that inhibit or reduce the ability of D-SLAM to bind D-SLAM receptor in vitro and/or in vivo. In a specific embodiment, antibodies of the invention inhibit or reduce the ability of D-SLAM to bind D-SLAM receptor in vitro. In another nonexclusive specific embodiment, antibodies of the invention inhibit or reduce the ability of D-SLAM to bind D-SLAM receptor in vivo. Such inhibition can be assayed using techniques described herein or otherwise known in the art.

The invention also encompasses, antibodies that bind specifically to D-SLAM, but do not inhibit the ability of D-SLAM to bind D-SLAM receptor in vitro and/or in vivo. In a specific embodiment, antibodies of the invention do not inhibit or reduce the ability of D-SLAM to bind D-SLAM receptor in vitro. In another nonexclusive specific embodiment, antibodies of the invention do not inhibit or reduce the ability of D-SLAM to bind D-SLAM receptor in vivo.

As described above, the invention encompasses antibodies that inhibit or reduce a D-SLAM-mediated biological activity in vitro and/or in vivo. In a specific embodiment, antibodies of the invention inhibit or reduce D-SLAM-mediated inhibition of B cell proliferation in vitro. Such inhibition can be assayed by routinely modifying B cell proliferation assays described herein or otherwise known in the art. In another nonexclusive specific embodiment, antibodies of the invention inhibit or reduce D-SLAM-mediated inhibition of B cell proliferation in vivo.

Alternatively, the invention also encompasses, antibodies that bind specifically to D-SLAM, but do not inhibit or reduce a D-SLAM-mediated biological activity in vitro and/or in vivo (e.g., inhibition of B cell proliferation). In a specific embodiment, antibodies of the invention do not inhibit or reduce a D-SLAM-mediated biological activity in vitro. In another non-exclusive embodiment, antibodies of the invention do not inhibit or reduce a D-SLAM-mediated biological activity in vivo.

As described above, the invention encompasses antibodies that specifically bind to the same epitope as at least one of the antibodies specifically referred to herein, in vitro and/or in vivo.

The antibodies of the invention also have uses as therapeutics and/or prophylactics which include, but are not limited to, in activating monocytes or blocking monocyte activation and/or killing specific cell types that express the membrane bound form of D-SLAM on their cell surfaces (e.g., to treat, prevent, and/or diagnose leukemias, lymphomas, rheumatoid arthritis, and other diseases or conditions associated with these cell types). In a specific embodiment, the antibodies of the invention fix complement. In other specific embodiments, as further described herein, the antibodies of the invention (or fragments thereof) are associated with heterologous polypeptides or nucleic acids (e.g. toxins, such as, compounds that bind and activate endogenous cytotoxic effecter systems, and radioisotopes; and cytotoxic prodrugs).

As discussed above, antibodies to the D-SLAM polypeptides of the invention can, in turn, be utilized to generate anti-idiotype antibodies that "mimic" the D-SLAM, using techniques well known to those skilled in the art. (See, e.g., Greenspan & Bona, FASFB J. 7(5):437–444 (1989), and Nissinoff, J. Immunol. 147(8):2429–2438 (1991)). Such neutralizing anti-idiotypes or Fab fragments of such anti-idiotypes can be used in therapeutic regimens to neutralize D-SLAM ligand. For example, such anti-idiotypic antibodies can be used to bind D-SLAM, or to bind D-SLAM receptors on the surface of cells of B cell lineage, and thereby block D-SLAM-mediated inhibition of B cell activation, proliferation, and/or differentiation.

Fusion Proteins

Any D-SLAM polypeptide can be used to generate fusion proteins. For example, the D-SLAM polypeptide, when fused to a second protein, can be used as an antigenic tag. Antibodies raised against the D-SLAM polypeptide can be used to indirectly detect the second protein by binding to the D-SLAM. Moreover, because secreted proteins target cellular locations based on trafficking signals, the D-SLAM polypeptides can be used as a targeting molecule once fused to other proteins.

Examples of domains that can be fused to D-SLAM polypeptides include not only heterologous signal sequences, but also other heterologous functional regions. The fusion does not necessarily need to be direct, but may occur through linker sequences.

In certain preferred embodiments, D-SLAM proteins of the invention comprise, or alternatively consist of, fusion proteins wherein the D-SLAM polypeptides are those described above as m-n. In preferred embodiments, the application is directed to nucleic acid molecules at least 80%, 85%, 90%, 92%, 95%, 96%, 97%, 98% or 99% identical to the nucleic acid sequences encoding polypeptides having the amino acid sequence of the specific N- and C-terminal deletions recited herein.

Moreover, fusion proteins may also be engineered to improve characteristics of the D-SLAM polypeptide. For instance, a region of additional amino acids, particularly charged amino acids, may be added to the N-terminus of the D-SLAM polypeptide to improve stability and persistence during purification from the host cell or subsequent handling and storage. Also, peptide moieties may be added to the D-SLAM polypeptide to facilitate purification. Such regions may be removed prior to final preparation of the D-SLAM polypeptide. The addition of peptide moieties to facilitate handling of polypeptides are familiar and routine techniques in the art.

Moreover, D-SLAM polypeptides of the present invention, including fragments thereof, and specifically epitope-bearing fragments may be fused with heterologous polypeptide sequences. For example, the polypeptides of the present invention may be fused with parts of the constant domain of immunoglobulins (IgA, IgE, IgG, IgM) or portions thereof (CH1, CH2, CH3, and any combination thereof, including both entire domains and portions thereof), or albumin (including but not limited to recombinant albumin), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).) Polynucleotides comprising or alternatively consisting of nucleic acids which encode these fusion proteins are also encompassed by the invention.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the D-SLAM polypeptides can be fused to marker sequences, such as a peptide which facilitates purification of D-SLAM. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the D-SLAM polynucleotides or the polypeptides.

Recombinant and Synthetic Production of D-SLAM

The present invention also relates to vectors containing the isolated D-SLAM DNA molecules of the present invention, host cells which are genetically engineered with the recombinant vectors, and the production of polypeptides or fragments thereof by recombinant and synthetic techniques. The vector may be, for example, a phage, plasmid, viral, or retroviral vector. Retroviral vectors may be replication competent or replication defective. In the latter case, viral propagation generally will occur only in complementing host cells.

D-SLAM polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The D-SLAM polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pHE4-5 (ATCC Accession No. 209311; and variations thereof), pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PAO815 (all available from Invitrogen, Carlsbad, Calif.). Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan. Other suitable vectors will be readily apparent to the skilled artisan.

In one embodiment, the yeast Pichia pastoris is used to express D-SLAM protein in a eukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia postoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a D-SLAM polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a D-SLAM polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a D-SLAM protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In one embodiment, high-level expression of a heterologous coding sequence, such as, for example, a D-SLAM polynucleotide of the present invention, may be achieved by cloning the heterologous polynucleotide of the invention into an expression vector such as, for example, pGAPZ or pGAPZalpha, and growing the yeast culture in the absence of methanol.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that D-SLAM polypeptides may in fact be expressed by a host cell lacking a recombinant vector.

D-SLAM polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

D-SLAM polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the D-SLAM polypeptides may be glycosylated or may be non-glycosylated. In addition, D-SLAM polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., D-SLAM coding sequence), and/or to include genetic material (e.g., heterologous polynucleotide sequences) that is operably associated with D-SLAM polynucleotides of the invention, and which activates, alters, and/or amplifies endogenous D-SLAM polynucleotides. For example, techniques known in the art may be used to operably associate heterologous control regions (e.g., promoter and/or enhancer) and endogenous D-SLAM polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller, M., et al., 1984, Nature 310:105–111). For example, a peptide corresponding to a fragment of the D-SLAM polypeptides of the invention can be synthesized by use of a peptide synthesizer. Furthermore, if desired, nonclassical amino acids or chemical amino acid analogs can be introduced as a substitution or addition into the D-SLAM polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses D-SLAM polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of D-SLAM which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The D-SLAM polypeptides of the invention may be in monomers or multimers (i.e., dimers, trimers, tetramers and higher multimers). Accordingly, the present invention relates to monomers and multimers of the D-SLAM polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only D-SLAM polypeptides of the invention (including D-SLAM fragments, variants, splice variants, and fusion proteins, as described herein). These homomers may contain D-SLAM polypeptides having identical or different amino acid sequences. In a specific embodiment, a homomer of the invention is a multimer containing only D-SLAM polypeptides having an identical amino acid sequence. In another specific embodiment, a homomer of the invention is a multimer containing D-SLAM polypeptides having different amino acid sequences. In specific embodiments, the multimer of the invention is a homodimer (e.g., containing D-SLAM polypeptides having identical or different amino acid sequences) or a homotrimer (e.g., containing D-SLAM polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the D-SLAM polypeptides of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the D-SLAM polypeptides of the invention. Such covalent associations may involve one or more amino acid residues contained in the polypeptide sequence (e.g., that recited in SEQ ID NO:2, or contained in the polypeptide encoded by the clone HDPJO39). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a D-SLAM fusion protein. In one example, covalent associations are between the heterologous sequence contained in a fusion protein of the invention (see, e.g., U.S. Pat. No. 5,478,925). In a specific example, the covalent associations are between the heterologous sequence contained in a D-SLAM-Fc fusion protein of the invention (as described herein). In another specific example, covalent associations of fusion proteins of the invention are between heterologous polypeptide sequence from another Secreted Lymphocyte Activation Molecule (SLAM) family member that is capable of forming covalently associated multimers, such as for example, oseteoprotegerin (see, e.g., International Publication No. WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple potypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the D-SLAM Polynucleotides

The D-SLAM polynucleotides identified herein can be used in numerous ways as reagents. The following description should be considered exemplary and utilizes known techniques.

There exists an ongoing need to identify new chromosome markers, since few chromosome marking reagents, based on actual sequence data (repeat polymorphisms), are presently available.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human D-SLAM gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the D-SLAM polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the D-SLAM polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the D-SLAM polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the D-SLAM polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the D-SLAM polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using D-SLAM polynucleotides. Any of these alterations (altered expression, chromosomal rearrangement, or mutation) can be used as a diagnostic or prognostic marker.

In addition to the foregoing, a D-SLAM polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat, diagnose, detect, and/or prevent disease.

D-SLAM polynucleotides are also useful in gene therapy. One goal of gene therapy is to insert a normal gene into an organism having a defective gene, in an effort to correct the genetic defect. D-SLAM offers a means of targeting such genetic defects in a highly accurate manner. Another goal is to insert a new gene that was not present in the host genome, thereby producing a new trait in the host cell.

The D-SLAM polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The D-SLAM polynucleotides can be used as additional DNA markers for RFLP.

The D-SLAM polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, D-SLAM polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, or alternatively consist of, for example, DNA probes or primers specific to particular tissue prepared from D-SLAM sequences. Panels of such reagents can identify tissue by species and/or by organ type. In a similar fashion, these reagents can be used to screen tissue cultures for contamination.

Because D-SLAM is found expressed in dendritic cells, T cell lymphoma, lymph node, spleen, thymus, small intestine, and uterus, D-SLAM polynucleotides are useful as hybridization probes for differential identification of the tissue(s) or cell type(s) present in a biological sample. Similarly, polypeptides and antibodies directed to D-SLAM polypeptides are useful to provide immunological probes for differential identification of the tissue(s) or cell type(s). In addition, for a number of disorders of the above tissues or cells, particularly of the immune system, significantly higher or lower levels of D-SLAM gene expression may be detected in certain tissues (e.g., cancerous and wounded tissues) or bodily fluids (e.g., serum, plasma, urine, synovial fluid or spinal fluid) taken from an individual having such a disorder, relative to a "standard" D-SLAM gene expression level, i.e., the D-SLAM expression level in healthy tissue from an individual not having the immune system disorder.

Thus, the invention provides a diagnostic method of a disorder, which involves: (a) assaying D-SLAM gene expression level in cells or body fluid of an individual; (b) comparing the D-SLAM gene expression level with a standard D-SLAM gene expression level, whereby an increase or decrease in the assayed D-SLAM gene expression level compared to the standard expression level is indicative of disorder in the immune system.

In the very least, the D-SLAM polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of D-SLAM Polypeptides

D-SLAM polypeptides can be used in numerous ways. The following description should be considered exemplary and utilizes known techniques.

D-SLAM polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of D-SLAM polypeptide in cells or body fluid of an individual; (b) comparing the level of gene expression with a standard gene expression level, whereby an increase or decrease in the assayed D-SLAM polypeptide gene expression level compared to the standard expression level is indicative of a disorder.

Moreover, D-SLAM polypeptides can be used to treat, diagnose, detect, and/or prevent disease. For example, patients can be administered D-SLAM polypeptides in an effort to replace absent or decreased levels of the D-SLAM polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to D-SLAM polypeptides can also be used to treat, diagnose, detect, and/or prevent disease. For example, administration of an antibody directed to a D-SLAM polypeptide can bind and reduce overproduction of the polypeptide. Similarly, administration of an antibody can activate the polypeptide, such as by binding to a polypeptide bound to a membrane (receptor).

At the very least, the D-SLAM polypeptides can be used as molecular weight markers on SDS-PAGE gels or on molecular sieve gel filtration columns using methods well known to those of skill in the art. D-SLAM polypeptides can also be used to raise antibodies, which in turn are used to measure protein expression from a recombinant cell, as a way of assessing transformation of the host cell. Moreover, D-SLAM polypeptides can be used to test the following biological activities.

Gene Therapy Methods

Another aspect of the present invention is to gene therapy methods for treating, diagnosing, detecting, and/or preventing disorders, diseases and/or conditions. The gene therapy methods relate to the introduction of nucleic acid (DNA, RNA and antisense DNA or RNA) sequences into an animal to achieve expression of the D-SLAM polypeptide of the present invention. This method requires a polynucleotide which codes for a D-SLAM polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a D-SLAM polynucleotide ex vivo, with the engineered cells then being provided to a patient to be treated (therapeutically and/or prophylactically) and/or diagnosed with the polypeptide. Such methods are well-known in the art. For example, see Belldegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the D-SLAM polynucleotide constructs can be delivered by any method that delivers injectable materials to the cells of an animal, such as, injection into the interstitial space of tissues (heart, muscle, skin, lung, liver, and the like). The D-SLAM polynucleotide constructs may be delivered in a pharmaceutically acceptable liquid or aqueous carrier.

In one embodiment, the D-SLAM polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the D-SLAM polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The D-SLAM polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of D-SLAM DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the melallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for D-SLAM.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The D-SLAM polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated (therapeutically and/or prophylactically) and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked D-SLAM DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced in the Examples, naked D-SLAM nucleic acid sequences can be administered in vivo results in the successful expression of D-SLAM polypeptide in the femoral arteries of rabbits.

The constructs may also be delivered with delivery vehicles such as viral sequences, viral particles, liposome formulations, lipofectin, precipitating agents, etc. Such methods of delivery are known in the art.

In certain embodiments, the D-SLAM polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589, 466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding D-SLAM. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding D-SLAM. Such retroviral vector particles then may be employed, to transduce eukaryotic cells, either in vitro or in vivo. The transduced eukaryotic cells will express D-SLAM.

In certain other embodiments, cells are engineered, ex vivo or in vivo, with D-SLAM polynucleotide contained in an adenovirus vector. Adenovirus can be manipulated such that it encodes and expresses D-SLAM, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis.109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The D-SLAM polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the D-SLAM polynucleotide construct. These viral particles are then used to transduce eukaryotic cells, either ex vivo or in vivo. The transduced cells will contain the D-SLAM polynucleotide construct integrated into its genome, and will express D-SLAM.

Another method of gene therapy involves operably associating heterologous control regions and endogenous polynucleotide sequences (e.g. encoding D-SLAM) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the D-SLAM desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous D-SLAM sequence is placed under the control of the promoter. The promoter then drives the expression of the endogenous D-SLAM sequence.

The polynucleotides encoding D-SLAM may be administered along with other polynucleotides encoding other angiongenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding D-SLAM contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities of D-SLAM

D-SLAM polynucleotides or polypeptides, or agonists or antagonists of D-SLAM, can be used in assays to test for one or more biological activities. If D-SLAM polynucleotides or polypeptides, or agonists or antagonists of D-SLAM, do exhibit activity in a particular assay, it is likely that D-SLAM may be involved in the diseases associated with the biological activity. Therefore, D-SLAM could be used to treat, diagnose, detect, and/or prevent the associated disease.

D-SLAM is a cell surface receptor homologous to members of the Secreted Lymphocyte Activation Molecule (SLAM) family, and thus should have activity similar to other SLAM family members. Current studies in the literature demonstrate that SLAM can associate with itself, and that this homotypic interaction can activate B- and T-cells. Therefore, D-SLAM may interact specifically with SLAM, with D-SLAM (a homotypic interaction), or other B- and T-cell receptor molecules on the surface of B- and T-cells to affect the activation, proliferation, survival, and/or differentiation of immune cells. Similarly, soluble D-SLAM may be an important costimulatory molecule for therapeutic uses or immune modulation. Ligands, such as antibodies, may mimic the action of soluble D-SLAM by binding to D-SLAM, SLAM, or other dendritic cell receptors.

D-SLAM inhibits the proliferation of B-cells. See, the experimental results shown in Examples 32–33, below.

In a preferred embodiment of the invention, D-SLAM and/or D-SLAM agonists can be used to inhibit the proliferation of B-cells. Thus, D-SLAM and/or D-SLAM agonists would be useful in treating, preventing, diagnosing, detecting, and/or ameliorating diseases and/or disorders related to an overproliferation of B-cells.

In a preferred embodiment of the invention, D-SLAM antagonists can be used to promote the proliferation of B-cells. Thus, D-SLAM antagonists would be useful in treating, preventing, diagnosing, detecting, and/or ameliorating diseases and/or disorders related to a reduced proliferation of B-cells.

Binding of D-SLAM induces the production of interferon-gamma from other cell types, particularly T- and B-cells (data not shown.) The binding may occur through homotypic association with membrane bound D-SLAM, association with SLAM, or association with other T- or B-cell receptors. Ligands, such as antibodies, may mimic the induction of interferon-gamma by soluble D-SLAM by binding to D-SLAM, SLAM, or other dendritic cell receptors.

Moreover, because of the tissue distribution of D-SLAM, this protein may also play a role in stimulating dendritic or antigen presenting cells. For example, a secreted form of D-SLAM, containing the extracellular domain or the full-length form, may bind to and stimulate D-SLAM molecules located on the surface of dendritic or antigen-presenting cells in homotypic manner. Binding may also occur to SLAM, or other dendritic cell surface receptors. This binding may regulate the survival, proliferation, differentiation, activation or maturation of dendritic cells or antigen presenting cells, effecting antigen recognition and immune response. Moreover, ligands, such as antibodies, may mimic the action of soluble D-SLAM by binding to D-SLAM, SLAM, or other dendritic cell receptors.

Thus, D-SLAM may be useful as a therapeutic molecule. It could be used to control the proliferation, activation, maturation, survival, and/or differentiation of hematopoietic cells, in particular B- and T-cells. Particularly, D-SLAM may be a useful therapeutic to mediate immune modulation, and may influence the Th0-TH1-TH2 profile of a patient's immune system. For example, D-SLAM may drive immune response to the Th0-TH1 pathway. This control of immune cells would be particularly important in the treatment, diagnosis, detection, and/or prevention of immune disorders, such as autoimmune diseases or immunosuppression (see below). Preferably, treatment, diagnosis, detection, and/or prevention of immune disorders could be carried out using a secreted form of D-SLAM, gene therapy, or ex vivo applications. Moreover, inhibitors of D-SLAM, either blocking antibodies or mutant forms, could modulate the expression of D-SLAM. These inhibitors may be useful to treat, diagnose, detect, and/or prevent diseases associated with the misregulation of D-SLAM, such as T cell lymphoma.

In one embodiment, the invention provides a method for the specific delivery of compositions of the invention to cells by administering polypeptides of the invention (e.g., D-SLAM polypeptides or anti-D-SLAM antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., D-SLAM polypeptides or anti-D-SLAM antibodies) in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, 131I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

It will be appreciated that conditions caused by a decrease in the standard or normal level of D-SLAM activity in an individual, particularly disorders of the immune system, can be treated by administration of D-SLAM polypeptide (in the form of soluble extracellular domain or cells expressing the complete protein) or agonist. Thus, the invention also provides a method of treatment of an individual in need of an increased level of D-SLAM activity comprising administering to such an individual a pharmaceutical composition comprising an amount of an isolated D-SLAM polypeptide of the invention, or agonist thereof (e.g, an agonistic D-SLAM antibody), effective to increase the D-SLAM activity level in such an individual.

It will also be appreciated that conditions caused by a increase in the standard or normal level of D-SLAM activity in an individual, particularly disorders of the immune system, can be treated by administration of D-SLAM polypeptides (in the form of soluble extracellular domain or cells expressing the complete protein) or antagonist (e.g, an antagonistic D-SLAM antibody). Thus, the invention also provides a method of treatment of an individual in need of an dereased level of D-SLAM activity comprising administering to such an individual a pharmaceutical composition comprising an amount of an isolated D-SLAM polypeptide of the invention, or antagonist thereof, effective to decrease the D-SLAM activity level in such an individual.

Viruses are one example of an infectious agent that can cause disease or symptoms that can be treated by D-SLAM polynucleotides or polypeptides, or agonists of D-SLAM. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. D-SLAM polynucleotides or polypeptides, or agonists or antagonists of D-SLAM, can be used to treat, prevent, diagnose, and/or detect any of these symptoms or diseases. In specific embodiments, D-SLAM polynucleotides, polypeptides, or agonists are used to treat, prevent, and/or diagnose: meningitis, Dengue, EBV, and/or hepatitis (e.g., hepatitis B). In an additional specific embodiment D-SLAM polynucleotides, polypeptides, or agonists are used to treat patients nonresponsive to one or more other commercially available hepatitis vaccines. In a further specific embodiment, D-SLAM polynucleotides, polypeptides, or agonists are used to treat, prevent, and/or diagnose AIDS. In an additional specific embodiment D-SLAM polynucleotides, polypeptides, agonists, and/or antagonists are used to treat, prevent, and/or diagnose patients with cryptosporidiosis.

Similarly, bacterial or fungal agents that can cause disease or symptoms and that can be treated by D-SLAM polynucleotides or polypeptides, or agonists or antagonists of D-SLAM, include, but not limited to, the following Gram-Negative and Gram-positive. bacteria and bacterial families and fungi: Actinomycetales (e.g., Corynebacterium, Mycobacterium, Norcardia), *Cryptococcus neoformans,* Aspergillosis, Bacillaceae (e.g., Anthrax, Clostridium), Bacteroidaceae, Blastomycosis, Bordetella, Borrelia (e.g., *Borrelia burgdorferi,* Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi,* and *Salmonella paratyphi*), Serratia, Yersinia), Erysipelothrix, Helicobacter, Legionellosis, Leptospirosis, Listeria (e.g, *Listeria monocytogenes*), Mycoplasmatales, *Mycobacterium leprae, Vibrio cholerae,* Neisseriaceae (e.g., Acinetobacter, Gonorrhea, Menigococcal), *Meisseria meningitidis,* Pasteurellacea Infections (e.g., Actinobacillus, Heamophilus (e.g., Heamophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. D-SLAM polynucleotides or polypeptides, or agonists or antagonists of D-SLAM, can be used to treat, prevent, diagnose, and/or detect any of these symptoms or diseases. In specific embodiments, D-SLAM polynucleotides, polypeptides, or antagonists thereof are used to treat, prevent, and/or diagnose: tetanus, Diptheria, botulism, and/or meningitis type B.

Moreover, parasitic agents causing disease or symptoms that can be treated by D-SLAM polynucleotides or polypeptides, or antagonists of D-SLAM, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. D-SLAM polynucleotides or polypeptides, or antagonists or antagonists of D-SLAM, can be used to treat, prevent, diagnose, and/or detect any of these symptoms or diseases. In specific embodiments, D-SLAM polynucleotides, polypeptides, or antagonists thereof are used to treat, prevent, and/or diagnose malaria.

In another embodiment, D-SLAM polynucleotides or polypeptides of the invention and/or agonists and/or antagonists thereof, are used to treat, prevent, and/or diagnose inner ear infection (such as, for example, otitis media), as well as other infections characterized by infection with *Streptococcus pneumoniae* and other pathogenic organisms.

In a specific embodiment, D-SLAM polynucleotides or polypeptides, or agonists or antagonists thereof (e.g., anti-D-SLAM antibodies) are used to treat or prevent a disorder characterized by deficient serum immunoglobulin production, recurrent infections, and/or immune system dysfunction. Moreover, D-SLAM polynucleotides or polypeptides, or agonists or antagonists thereof (e.g., anti-D-SLAM antibodies) may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pheumocystis carnii.

D-SLAM polynucleotides or polypeptides of the invention, or agonists or antagonists thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, D-SLAM polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g, neonatal thrombocytopenia), and immune-mediated neutropenia), transplantation (e.g, cytamegalovirus (CMV)-negative recipients of CMV-positive organs), hypogammaglobulinemia (e.g., hypogammaglobulinemic neonates with risk factor for infection or morbidity), epilepsy (e.g, intractable epilepsy), systemic vasculitic syndromes, myasthenia gravis (e.g, decompensation in myasthenia gravis), dermatomyositis, and polymyositis.

Additional preferred embodiments of the invention include, but are not limited to, the use of D-SLAM polypeptides, D-SLAM polynucleotides, and functional agonists and/or antagonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to inhibit the immune system to produce decreased quantities of one or more antibodies (e.g., IgG, IgA, IgM, and IgE), to inhibit higher affinity antibody production (e.g., IgG, IgA, IgM, and IgE), and/or to decrease an immune response. In a specific nonexclusive embodiment, D-SLAM polypeptides of the invention, and/ or agonists thereof, are administered to inhibit the immune system to produce decreased quantities of IgG. In another specific nonexclusive embodiment, D-SLAM polypeptides of the invention and/or agonists thereof, are administered to boost the immune system to produce decreased quantities of IgA. In another specific nonexclusive embodiment, D-SLAM polypeptides of the invention and/or agonists thereof, are administered to inhibit the immune system to produce decreased quantities of IgM.

As an agent that reduces the immune status of an individual prior to their receipt of immunosuppressive therapies.

As an agent to decrease serum immunoglobulin concentrations.

As an immune system inhibitor prior to, during, or after bone marrow transplant and/or other transplants (e.g., allogeneic or xenogeneic organ transplantation). With respect to transplantation, compositions of the invention may be administered prior to, concomitant with, and/or after transplantation.

As an agent to reduce immunoresponsiveness. B cell immunodeficiencies that may be ameliorated or treated by administering D-SLAM antagonists of the invention include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

D-SLAM antagonists may be used as agents to boost immunoresponsiveness among individuals having an acquired loss of B cell function. Conditions resulting in an acquired loss of B cell function that may be ameliorated or treated by administering the D-SLAM antagonists of the invention include, but are not limited to, HIV Infection, AIDS, bone marrow transplant, and B cell chronic lymphocytic leukemia (CLL).

D-SLAM antagonists may be used as agents to boost immunoresponsiveness among individuals having a temporary immune deficiency. Conditions resulting in a temporary immune deficiency that may be ameliorated or treated by administering D-SLAM antagonists include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As an agent to direct an individual's immune system towards development of a humoral response (i.e. TH2) as opposed to a TH1 cellular response.

As a means to inhibit tumor proliferation.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance D-SLAM-mediated responses.

As a means of inhibiting monocytes/macrophages to defend against parasitic diseases that effect monocytes such as Leshmania.

As pretreatment of bone marrow samples prior to transplant. Such treatment would decrease B cell representation and thus modulate recovery.

As a means of regulating secreted cytokines that are elicited by D-SLAM.

D-SLAM polypeptides or polynucleotides of the invention, or antagonists may be used to modulate IgE concentrations in vitro or in vivo.

Additionally, D-SLAM polypeptides or polynucleotides of the invention, or antagonists thereof, may be used to treat, prevent, and/or diagnose IgE-mediated allergic reactions. Such allergic reactions include, but are not limited to, asthma, rhinitis, and eczema.

In a specific embodiment, D-SLAM polypeptides or polynucleotides of the invention, or antagonists thereof, is administered to treat, prevent, diagnose, and/or ameliorate selective IgA deficiency.

In another specific embodiment, D-SLAM polypeptides or polynucleotides of the invention, or antagonists thereof, is administered to treat, prevent, diagnose, and/or ameliorate ataxia-telangiectasia.

In another specific embodiment, D-SLAM polypeptides or polynucleotides of the invention, or antagonists thereof, is administered to treat, prevent, diagnose, and/or ameliorate common variable immunodeficiency.

In another specific embodiment, D-SLAM polypeptides or polynucleotides of the invention, or antagonists thereof, is administered to treat, prevent, diagnose, and/or ameliorate X-linked agammaglobulinemia.

In another specific embodiment, D-SLAM polypeptides or polynucleotides of the invention, or antagonists thereof, is administered to treat, prevent, diagnose, and/or ameliorate severe combined immunodeficiency (SCID).

In another specific embodiment, D-SLAM polypeptides or polynucleotides of the invention, or antagonists thereof, is administered to treat, prevent, diagnose, and/or ameliorate Wiskott-Aldrich syndrome.

In another specific embodiment, D-SLAM polypeptides or polynucleotides of the invention, or antagonists thereof, is administered to treat, prevent, diagnose, and/or ameliorate X-linked Ig deficiency with hyper IgM.

In another specific embodiment, D-SLAM polypeptides or polynucleotides of the invention, or antagonists or antagonists (e.g., anti-D-SLAM antibodies) thereof, is administered to treat, prevent, and/or diagnose chronic myelogenous leukemia, acute myelogenous leukemia, leukemia, hysticocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, D-SLAM polypeptides or polynucleotides of the invention, or antagonists thereof, is administered to treat, prevent, diagnose, and/or ameliorate monocytic leukemoid reaction, as seen, for example, with tuberculosis.

In another specific embodiment, D-SLAM polypeptides or polynucleotides of the invention, or antagonists thereof, is administered to treat, prevent, diagnose, and/or ameliorate monocytic leukocytosis, monocytic leukopenia, monocytopenia, and/or monocytosis.

In a specific embodiment, D-SLAM polynucleotides or polypeptides of the invention, and/or anti-D-SLAM antibodies and/or agonists or antagonists thereof, are used to treat, prevent, detect, and/or diagnose primary B lymphocyte disorders and/or diseases, and/or conditions associated therewith.

In a preferred embodiment, D-SLAM polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e, mucopolysaccbaridosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, D-SLAM polynucleotides, polypeptides, and/or agonists and/or antagonists thereof are used to treat, prevent, and/or diagnose mucositis, especially as associated with chemotherapy.

In a preferred embodiment, D-SLAM polynucleotides, polypeptides, and/or agonists and/or antagonists thereof are used to treat, prevent, and/or diagnose diseases or disorders affecting or conditions associated with sinusitis.

An additional condition, disease or symptom that can be treated, prevented, and/or diagnosed by D-SLAM polynucleotides or polypeptides, or antagonists of D-SLAM, is osteomyelitis.

An additional condition, disease or symptom that can be treated, prevented, and/or diagnosed by D-SLAM polynucleotides or polypeptides, or antagonists of D-SLAM, is endocarditis.

All of the above described applications as they may apply to veterinary medicine.

D-SLAM antagonists may be used as a therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases, as well as a therapy for chronic hypergammaglobulinemeia evident in such diseases as monoclonalgammopathy of undetermined significance (MGUS), Waldenstrom's disease, related idiopathic monoclonalgammopathies, and plasmacytomas.

An immunosuppressive agent(s).

D-SLAM polypeptides or polynucleotides of the invention, or antagonists may be used to modulate IgE concentrations in vitro or in vivo.

In another embodiment, administration of D-SLAM polypeptides or polynucleotides of the invention, or antagonists thereof, may be used to treat, prevent, and/or diagnose IgE-mediated allergic reactions including, but not limited to, asthma, rhinitis, and eczema.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described herein.

All of the above described applications as they may apply to veterinary medicine. Moreover, all applications described herein may also apply to veterinary medicine.

D-SLAM polynucleotides or polypeptides of the invention and/or agonists and/or antagonists thereof, may be used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of D-SLAM polynucleotides or polypeptides of the invention and/or agonists and/or agonists thereof that can inhibit an immune response, particularly the proliferation of B cells and/or the production of immunoglobulins, may be an effective therapy in treating and/or preventing autoimmune disorders. Thus, in preferred embodiments, D-SLAM agonists of the invention are used to treat, prevent, and/or diagnose an autoimmune disorder.

Autoimmune disorders and conditions associated with these disorders that may be treated, prevented, and/or diagnosed with the D-SLAM polynucleotides, polypeptides, and/or agonists of the invention, include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye disease.

Additional autoimmune disorders (that are highly probable) that may be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), Goodpasture's syndrome (often characterized, e.g. by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by anti-spermatozoal antibodies), glomerulonephritis (often characterized, e.g., by glomerular basement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-D-SLAM antibodies.

In a specific preferred embodiment, rheumatoid arthritis is treated, prevented, and/or diagnosed using D-SLAM and/or other agonists of the invention.

In a specific preferred embodiment, lupus is treated, prevented, and/or diagnosed using D-SLAM and/or other agonists of the invention.

In a specific preferred embodiment, nephritis associated with lupus is treated, prevented, and/or diagnosed using D-SLAM and/or other agonists of the invention.

Similarly, allergic reactions and conditions, such as asthma (particularly allergic asthma) or other respiratory problems, may also be treated by D-SLAM polynucleotides or polypeptides of the invention and/or agonists and/or antagonists thereof. Moreover, these molecules can be used to treat, prevent, and/or diagnose anaphylaxis, hypersensitivity to an antigenic molecule, or blood group incompatibility.

D-SLAM polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of D-SLAM polynucleotides or polypeptides of the invention and/or agonists and/or antagonists thereof, that inhibits an immune response, particularly the proliferation, differentiation, or chemotaxis of T-cells, may be an effective therapy in preventing organ rejection or GVHD.

Similarly, D-SLAM polynucleotides or polypeptides of the invention and/or agonists and/or antagonists thereof, may also be used to modulate inflammation. For example, D-SLAM polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from overproduction of cytokines (e.g., TNF or IL-1.)

In a specific embodiment, anti-D-SLAM antibodies of the invention are used to treat, prevent, modulate, detect, and/or diagnose inflammation.

In a specific embodiment, anti-D-SLAM antibodies of the invention are used to treat, prevent, modulate, detect, and/or diagnose inflamatory disorders.

In another specific embodiment, anti-D-SLAM antibodies of the invention are used to treat, prevent, modulate, detect, and/or diagnose allergy and/or hypersensitivity.

In a specific embodiment, D-SLAM polynucleotides or polypeptides of the invention and/or agonists and/or antagonists thereof, are used to treat, prevent, and/or diagnose chronic obstructive pulmonary disease (COPD).

In another embodiment, D-SLAM polynucleotides or polypeptides of the invention and/or agonists and/or antagonists thereof, are used to treat, prevent, and/or diagnose fibroses and conditions associated with fibroses, such as, for example, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmer's clay pipestem fibrosis.

Diseases associated with increased cell survival, or the inhibition of apoptosis that may be diagnosed, treated, or prevented with the D-SLAM polynucleotides or polypeptides of the invention, and agonists and antagonists thereof, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Thus, in preferred embodiments D-SLAM polynucleotides or polypeptides of the invention and/or agonists or antagonists thereof, are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment D-SLAM polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in other embodiments, D-SLAM polynucleotides or polypeptides of the invention or agonists or antagonists thereof, are used to inhibit the growth, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis apoptosis that may be diagnosed, treated, or prevented with the D-SLAM polynucleotides or polypeptides of the invention, and agonists and antagonists thereof, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments D-SLAM polynucleotides or polypeptides of the invention and/or agonists or antagonists thereof, are used to treat, prevent, and/or diagnose the diseases and disorders listed above.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures). Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Preferably, treatment using D-SLAM polynucleotides or polypeptides, and/or agonists or antagonists of D-SLAM (e.g., anti-D-SLAM antibody), could either be by administering an effective amount of D-SLAM polypeptide of the invention, or agonist or antagonist thereof, to the patient, or by removing cells from the patient, supplying the cells with D-SLAM polynucleotide, and returning the engineered cells to the patient (ex vivo therapy). Moreover, as further discussed herein, the D-SLAM polypeptide or polynucleotide can be used as an adjuvant in a vaccine to raise an immune response against infectious disease.

Immune Activity

In one embodiment, D-SLAM polynucleotides or polypeptides or D-SLAM agonists or antagonists (e.g., anti-D-SLAM antibodies) of the invention are used to treat, prevent, diagnose, or prognose an individual having an immunodeficiency.

Immunodeficiencies that may be treated, prevented, diagnosed, and/or prognosed with the D-SLAM polynucleotides or polypeptides or D-SLAM agonists or antagonists (e.g., anti-D-SLAM antibodies) of the invention, include, but are not limited to one or more immunodeficiencies selected from: severe combined immunodeficiency (SCID)-X linked, SCID-autosornal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

D-SLAM polynucleotides or polypeptides, or agonists or antagonists of D-SLAM, may be useful in treating, diagnosing, detecting, and/or preventing deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, D-SLAM polynucleotides or polypeptides, or agonists or antagonists of D-SLAM, can be used as a marker or detector of a particular immune system disease or disorder.

D-SLAM polynucleotides or polypeptides, or agonists or antagonists of D-SLAM, may be useful in treating, diagnosing, detecting, and/or preventing deficiencies or disorders of hematopoietic cells. D-SLAM polynucleotides or polypeptides, or agonists or antagonists of D-SLAM, could be used to increase differentiation and proliferation of hematopoietic cells, including the pluripotent stem cells, in an effort to treat, diagnose, detect, and/or prevent those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, D-SLAM polynucleotides or polypeptides, or agonists or antagonists of D-SLAM, can also be used to modulate hemostatic (the stopping of bleeding) or thrombolytic activity (clot formation). For example, by increasing hemostatic or thrombolytic activity, D-SLAM polynucleotides or polypeptides, or agonists or antagonists of D-SLAM, could be used to treat, diagnose, detect, and/or prevent blood coagulation disorders (e.g., afibrinogenemia, factor deficiencies), blood platelet disorders (e.g. thrombocytopenia), or wounds resulting from trauma, surgery, or other causes. Alternatively, D-SLAM polynucleotides or polypeptides, or agonists or antagonists of D-SLAM, that can decrease hemostatic or thrombolytic activity could be used to inhibit or dissolve clotting, important in the treatment, diagnosis, detection, and/or prevention of heart attacks (infarction), strokes, or scarring.

D-SLAM polynucleotides or polypeptides, or agonists or antagonists of D-SLAM, may also be useful in treating, diagnosing, detecting, and/or preventing autoimmune disorders. Many autoimmune disorders result from inappropriate recognition of self as foreign material by immune cells. This inappropriate recognition results in an immune response leading to the destruction of the host tissue. Therefore, the administration of D-SLAM polynucleotides or polypeptides, or agonists or antagonists of D-SLAM, that can inhibit an immune response, particularly the proliferation, differentiation, or chemotaxis of T-cells, may be an effective therapy in preventing autoimmune disorders.

Examples of autoimmune disorders that can be treated, diagnosed, detected, and/or prevented include, but are not limited to: Addison's Disease, hemolytic anemia, antiphospholipid syndrome, rheumatoid arthritis, dermatitis, allergic encephalomyclitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, diagnosed, detected, and/or prevented by D-SLAM polynucleotides or polypeptides, or agonists or antagonists of D-SLAM. Moreover, these molecules can be used to treat, diagnose, detect, and/or prevent anaphylaxis, hypersensitivity to an antigenic molecule, or blood group incompatibility.

D-SLAM polynucleotides or polypeptides, or agonists or antagonists of D-SLAM, may also be used to treat, diagnose, detect, and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of D-SLAM polynucleotides or polypeptides, or agonists or antagonists of D-SLAM, that inhibits an immune response, particularly the proliferation, differentiation, or chemotaxis of T-cells, may be an effective therapy in preventing organ rejection or GVHD.

Similarly, D-SLAM polynucleotides or polypeptides, or agonists or antagonists of D-SLAM, may also be used to modulate inflammation. For example, D-SLAM polynucleotides or polypeptides, or agonists or antagonists of D-SLAM, may inhibit the proliferation and differentiation of cells involved in an inflammatory response. These molecules can be used to treat, diagnose, detect, and/or prevent inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

D-SLAM polynucleotides or polypeptides, or agonists or antagonists of D-SLAM, can be used to treat, diagnose, detect, and/or prevent hyperproliferative disorders, including neoplasms. D-SLAM polynucleotides or polypeptides, or agonists or antagonists of D-SLAM, may inhibit the proliferation of the disorder through direct or indirect interactions. Alternatively, D-SLAM polynucleotides or polypeptides, or agonists or antagonists of D-SLAM, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated, diagnosed, detected, and/or prevented. This immune response may be increased by either enhancing an existing immune response, or by initiating a new immune response. Alternatively, decreasing an immune response may also be a method of treating, diagnosing, detecting, and/or preventing hyperproliferative disorders, such as a chemotherapeutic agent.

Examples of hyperproliferative disorders that can be treated, diagnosed, detected, and/or prevented by D-SLAM polynucleotides or polypeptides, or agonists or antagonists of D-SLAM, include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated, diagnosed, detected, and/or prevented by D-SLAM polynucleotides or polypeptides, or agonists or antagonists of D-SLAM. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Cardiovascular Disorders

D-SLAM polynucleotides or polypeptides, or agonists or antagonists of D-SLAM, encoding D-SLAM may be used to treat, diagnose, detect, and/or prevent cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

D-SLAM polynucleotides or polypeptides, or agonists or antagonists of D-SLAM, are especially effective for the treatment, diagnosis, detection, and/or prevention of critical limb ischemia and coronary disease. As shown in the Examples, administration of D-SLAM polynucleotides and polypeptides to an experimentally induced ischemia rabbit hindlimb may restore blood pressure ratio, blood flow, angiographic score, and capillary density.

D-SLAM polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. D-SLAM polypeptides may be administered as part of a pharmaceutical composition, described in more detail below. Methods of delivering D-SLAM polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment, diagnosis, detection, and/or prevention of diseases or disorders associated with neovascularization by administration of the D-SLAM polynucleotides and/or polypeptides of the invention, as well as agonists or antagonists of D-SLAM. Malignant and metastatic conditions which can be treated, diagnosed, detected, and/or prevented with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)):

Ocular disorders associated with neovascularization which can be treated, diagnosed, detected, and/or prevented with the D-SLAM polynucleotides and polypeptides of the present invention (including D-SLAM agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Additionally, disorders which can be treated, diagnosed, detected, and/or prevented with the D-SLAM polynucleotides and polypeptides of the present invention (including D-SLAM agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated, diagnosed, detected, and/or prevented with the D-SLAM polynucleotides and polypeptides of the present invention (including D-SLAM agonist and/or antagonists) include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scieroderna, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

Diseases at the Cellular Level

Diseases associated with increased cell survival or the inhibition of apoptosis that could be treated, diagnosed, detected, and/or prevented by D-SLAM polynucleotides or polypeptides, as well as antagonists or agonists of D-SLAM, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, netiroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, D-SLAM polynucleotides, polypeptides, and/or antagonists of the invention are used to inhibit growth, progression, and/or metasis of cancers, in particular those listed above.

Additional diseases or conditions associated with increased cell survival that could be treated, diagnosed, detected, and/or prevented by D-SLAM polynucleotides or polypeptides, or agonists or antagonists of D-SLAM, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastonia, acoustic neuroma, oligodendroglioma, menangioma, melanoma, neuroblastoma, and retinoblastoma.

Diseases associated with increased apoptosis that could be treated, diagnosed, detected, and/or prevented by D-SLAM polynucleotides or polypeptides, as well as agonists or antagonists of D-SLAM, include AIDS; neurodegenerative disorders (such as Alzheimer's disease, Parkinson's disease, Amyotrophic lateral sclerosis, Retinitis pigmenlosa, Cerebellar degeneration and brain tumor or prior associated disease); autoimmune disorders (such as, multiple sclerosis, Sjogren's syndrome, Hasbimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing D-SLAM polynucleotides or polypeptides, as well as agonists or antagonists of D-SLAM, for therapeutic purposes, for example, to stimulate epithelial cell proliferation and basal keratinocytes for the purpose of wound healing, and to stimulate hair follicle production and healing of dermal wounds. D-SLAM polynucleotides or polypeptides, as well as agonists or antagonists of D-SLAM, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. D-SLAM polynucleotides or polypeptides, as well as agonists or antagonists of D-SLAM, could be used to promote dermal reestablishment subsequent to dermal loss D-SLAM polynucleotides or polypeptides, as well as agonists or antagonists of D-SLAM, could be used to increase the adherence of skin grafts to a wound bed and to stimulate re-epithelialization from the wound bed. The following are types of grafts that D-SLAM polynucleotides or polypeptides, agonists or antagonists of D-SLAM, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. D-SLAM polynucleotides or polypeptides, as well as agonists or antagonists of D-SLAM, can be used to promote skin strength and to improve the appearance of aged skin.

It is believed that D-SLAM polynucleotides or polypeptides, as well as agonists or antagonists of D-SLAM, will also produce changes in hepatocyte proliferation, and epithelial cell proliferation in the lung, breast, pancreas, stomach, small intesting, and large intestine. D-SLAM polynucleotides or polypeptides, as well as agonists or antagonists of D-SLAM, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. D-SLAM polynucleotides or polypeptides, agonists or antagonists of D-SLAM, may promote proliferation of endothelial cells, keratinocytes, and basal keratinocytes.

D-SLAM polynucleotides or polypeptides, as well as agonists or antagonists of D-SLAM, could also be used to reduce the side effects of gut toxicity that result from radiation, chemotherapy treatments or viral infections. D-SLAM polynucleotides or polypeptides, as well as agonists or antagonists of D-SLAM, may have a cytoprotective effect on the small intestine mucosa. D-SLAM polynucleotides or polypeptides, as well as agonists or antagonists of D-SLAM, may also stimulate healing of mucositis (mouth ulcers) that result from chemotherapy and viral infections.

D-SLAM polynucleotides or polypeptides, as well as agonists or antagonists of D-SLAM, could further be used in full regeneration of skin in full and partial thickness skin defects, including burns, (i.e., repopulation of hair follicles, sweat glands, and sebaceous glands), treatment, diagnosis, detection, and/or prevention of other skin defects such as psoriasis. D-SLAM polynucleotides or polypeptides, as well as agonists or antagonists of D-SLAM, could be used to treat, diagnose, detect, and/or prevent epidernolysis bullosa, a defect in adherence of the epidermis to the underlying dermis which results in frequent, open and painful blisters by accelerating recpithelialization of these lesions. D-SLAM polynucleotides or polypeptides, as well as agonists or antagonists of D-SLAM, could also be used to treat, diagnose, detect, and/or prevent gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, D-SLAM polynucleotides or polypeptides, as well as agonists or antagonists of D-SLAM, could be used to promote the resurfacing of the mucosal surface to aid more rapid healing and to prevent progression of inflammatory bowel disease. Treatment, diagnosis, detection, and/or prevention with D-SLAM polynucleotides or polypeptides, agonists or antagonists of D-SLAM, is expected to have a significant effect on the production of mucus throughout the gastrointestinal tract and could be used to protect the intestinal mucosa from injurious substances that are ingested or following surgery. D-SLAM polynucleotides or polypeptides, as well as agonists or antagonists of D-SLAM, could be used to treat, diagnose, detect, and/or prevent diseases associate with the under expression of D-SLAM.

Moreover, D-SLAM polynucleotides or polypeptides, as well as agonists or antagonists of D-SLAM, could be used to prevent and heal damage to the lungs due to various pathological states. A growth factor such as D-SLAM polynucleotides or polypeptides, as well as agonists or antagonists of D-SLAM, which could stimulate proliferation and differentiation and promote the repair of alveoli and brochiolar epithelium to prevent or treat, diagnose, detect, and/or prevent acute or chronic lung damage. For example, emphysema, which results in the progressive loss of aveolis, and inhalation injuries, i.e., resulting from smoke inhalation and burns, that cause necrosis of the bronchiolar epithelium and alveoli could be effectively treated, diagnosed, detected, and/or prevented using D-SLAM polynucleotides or polypeptides, agonists or antagonists of D-SLAM. Also, D-SLAM polynucleotides or polypeptides, as well as agonists or antagonists of D-SLAM, could be used to stimulate the proliferation of and differentiation of type H pneumocytes, which may help treat, diagnose, detect, and/or prevent disease such as hyaline membrane diseases, such as infant respiratory distress syndrome and bronchopulmonary displasia, in premature infants.

D-SLAM polynucleotides or polypeptides, as well as agonists or antagonists of D-SLAM, could stimulate the proliferation and differentiation of hepatocytes and, thus, could be used to alleviate, treat, diagnose, detect, and/or prevent liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, D-SLAM polynucleotides or polypeptides, as well as agonists or antagonists of D-SLAM, could be used treat, diagnose, detect, and/or prevent the onset of diabetes mellitus. In patients with newly diagnosed Types I and II diabetes, where some islet cell function remains, D-SLAM polynucleotides or polypeptides, as well as agonists or antagonists of D-SLAM, could be used to maintain the islet function so as to alleviate, delay or prevent permanent manifestation of the disease. Also, D-SLAM polynucleotides or polypeptides, as well as agonists or antagonists of D-SLAM, could be used as an auxiliary in islet cell transplantation to improve or promote islet cell function.

Infectious Disease

D-SLAM polynucleotides or polypeptides, or agonists or antagonists of D-SLAM, can be used to treat, diagnose, detect, and/or prevent infectious agents. For example, by increasing the immune response, particularly increasing the proliferation and differentiation of B and/or T cells, infectious diseases may be treated, diagnosed, detected, and/or prevented. The immune response may be increased by either enhancing an existing immune response, or by initiating a new immune response. Alternatively, D-SLAM polynucleotides or polypeptides, or agonists or antagonists of D-SLAM, may also directly inhibit the infectious agent, without necessarily eliciting an immune response.

Viruses are one example of an infectious agent that can cause disease or symptoms that can be treated, diagnosed, detected, and/or prevented by D-SLAM polynucleotides or polypeptides, or agonists or antagonists of D-SLAM. Examples of viruses, include, but are not limited to the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridac (Hepatitis), Herpesviridac (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. D-SLAM polynucleotides or polypeptides, or agonists or antagonists of D-SLAM, can be used to treat, diagnose, detect, and/or prevent any of these symptoms or diseases.

Similarly, bacterial or fungal agents that can cause disease or symptoms and that can be treated, diagnosed, detected, and/or prevented by D-SLAM polynucleotides or polypeptides, or agonists or antagonists of D-SLAM, include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, derrnatocycoses), toxemia, urinary tract infections, wound infections. D-SLAM polynucleotides or polypeptides, or agonists or antagonists of D-SLAM, can be used to treat, diagnose, detect, and/or prevent any of these symptoms or diseases.

Moreover, parasitic agents causing disease or symptoms that can be treated, diagnosed, detected, and/or prevented by D-SLAM polynucleotides or polypeptides, or agonists or antagonists of D-SLAM, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. D-SLAM polynucleotides or polypeptides, or agonists or antagonists of D-SLAM, can be used to treat, diagnose, detect, and/or prevent any of these symptoms or diseases.

Preferably, treatment, diagnosis, detection, and/or prevention using D-SLAM polynucleotides or polypeptides, or agonists or antagonists of D-SLAM, could either be by administering an effective amount of D-SLAM polypeptide to the patient, or by removing cells from the patient, supplying the cells with D-SLAM polynucleotide, and returning the engineered cells to the patient (ex vivo therapy). Moreover, the D-SLAM polypeptide or polynucleotide can be used as an antigen in a vaccine to raise an immune response against infectious disease.

Regeneration

D-SLAM polynucleotides or polypeptides, or agonists or antagonists of D-SLAM, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, D-SLAM polynucleotides or polypeptides, or agonists or antagonists of D-SLAM, may increase regeneration of tissues difficult to heal. For example, increased tendon/ligament regeneration would quicken recovery time after damage. D-SLAM polynucleotides or polypeptides, or agonists or antagonists of D-SLAM, of the present invention could also be used prophylactically in an effort to avoid damage. Specific diseases that could be treated, diagnosed, detected, and/or prevented include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using D-SLAM polynucleotides or polypeptides, or agonists or antagonists of D-SLAM, to proliferate and differentiate nerve cells. Diseases that could be treated, diagnosed, detected, and/or prevented using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, diagnosed, detected, and/or prevented using the D-SLAM polynucleotides or polypeptides, or agonists or antagonists of D-SLAM.

Chemotaxis

D-SLAM polynucleotides or polypeptides, or agonists or antagonists of D-SLAM, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

D-SLAM polynucleotides or polypeptides, or agonists or antagonists of D-SLAM, may increase chemotaxic activity of particular cells. These chemotactic molecules can then be used to treat, diagnose, detect, and/or prevent inflammation, infection, hyperproliferative disorders, or any immune system disorder by increasing the number of cells targeted to a particular location in the body. For example, chemotaxic molecules can be used to treat, diagnose, detect, and/or prevent wounds and other trauma to tissues by attracting immune cells to the injured location. As a chemotactic molecule, D-SLAM could also attract fibroblasts, which can be used to treat, diagnose, detect, and/or prevent wounds.

It is also contemplated that D-SLAM polynucleotides or polypeptides, or agonists or antagonists of D-SLAM, may inhibit chemotactic activity. These molecules could also be used to treat, diagnose, detect, and/or prevent disorders. Thus, D-SLAM polynucleotides or polypeptides, or agonists or antagonists of D-SLAM, could be used as an inhibitor of chemotaxis.

Binding Activity

D-SLAM polypeptides may be used to screen for molecules that bind to D-SLAM or for molecules to which D-SLAM binds. The binding of D-SLAM and the molecule may activate (agonist), increase, inhibit (antagonist), or decrease activity of the D-SLAM or the molecule bound. Examples of such molecules include antibodies, oligonucleotides, proteins (e.g., receptors),or small molecules.

Preferably, the molecule is closely related to the natural ligand of D-SLAM, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which D-SLAM binds, or at least, a fragment of the receptor capable of being bound by D-SLAM (e.g., active site). In either case, the molecule can be rationally designed using known techniques.

Preferably, the screening for these molecules involves producing appropriate cells which express D-SLAM, either as a secreted protein or on the cell membrane. Preferred cells include cells from mammals, yeast, Drosophila, or E. coli. Cells expressing D-SLAM (or cell membrane containing the expressed polypeptide) are then preferably contacted with a test compound potentially containing the molecule to observe binding, stimulation, or inhibition of activity of either D-SLAM or the molecule.

The assay may simply test binding of a candidate compound to D-SLAM, wherein binding is detected by a label, or in an assay involving competition with a labeled competitor. Further, the assay may test whether the candidate compound results in a signal generated by binding to D-SLAM.

Alternatively, the assay can be carried out using cell-free preparations, polypeptide/molecule affixed to a solid support, chemical libraries, or natural product mixtures. The assay may also simply comprise the steps of mixing a candidate compound with a solution containing D-SLAM, measuring D-SLAM/molecule activity or binding, and comparing the D-SLAM/molecule activity or binding to a standard.

Preferably, an ELISA assay can measure D-SLAM level or activity in a sample (e.g., biological sample) using a monoclonal or polyclonal antibody. The antibody can measure D-SLAM level or activity by either binding, directly or indirectly, to D-SLAM or by competing with D-SLAM for a substrate.

Additionally, the receptor to which D-SLAM binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of D-SLAM thereby effectively generating agonists and antagonists of D-SLAM. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of D-SLAM polynucleotides and corresponding polypeptides may be achieved by DNA shuffling. DNA shuffling involves the assembly of two or more DNA segments into a desired D-SLAM molecule by homologous, or site-specific, recombination. In another embodiment, D-SLAM polynucleotides and corresponding polypeptides may be alterred by being subjected to random mutagenesis by error-prone PCR, random nucleotide insertion or other methods prior to recombination. In another embodiment, one or more components, motifs, sections, parts, domains, fragments, etc., of D-SLAM may be recombined with one or more components, motifs, sections, parts, domains, fragments, etc. of one or more heterologous molecules. In preferred embodiments, the heterologous molecules are Secreted Lymphocyte Activation Molecule (SLAM) family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active D-SLAM fragments. Biologically active fragments are those exhibiting activity similar, but not necessarily identical, to an activity of the D-SLAM polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and [$^3$H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of [$^3$H] thymidine in each case. The amount of fibroblast cell proliferation is measured by liquid scintillation chromatography which measures the incorporation of[$^3$H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the D-SLAM receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, diagnose, detect, and/or prevent disease or to bring about a particular result in a patient (e.g., blood vessel growth) by activating or inhibiting the D-SLAM/molecule. Moreover, the assays can discover agents which may inhibit or enhance the production of D-SLAM from suitably manipulated cells or tissues. Therefore, the invention includes a method of identifying compounds which bind to D-SLAM comprising the steps of: (a) incubating a candidate binding compound with D-SLAM; and (b) determining if binding has occurred. Moreover, the invention includes a method of identifying agonists/antagonists comprising the steps of: (a) incubating a candidate compound with D-SLAM, (b) assaying a biological activity, and (b) determining if a biological activity of D-SLAM has been altered.

Also, one could identify molecules bind D-SLAM experimentally by using the beta-pleated sheet regions disclosed in FIG. 3 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1. Additional embodiments of the invention are directed to polynucleotides encoding D-SLAM polypeptides which comprise, or alternatively consist of, any combination or all of the beta pleated sheet regions disclosed in FIG. 3/Table 1. Additional preferred embodiments of the invention are directed to polypeptides which comprise, or alternatively consist of, the D-SLAM amino acid sequence of each of the beta pleated sheet regions disclosed in FIG. 3/Table 1. Additional embodiments of the invention are directed to D-SLAM polypeptides which comprise, or alternatively consist of, any combination or all of the beta pleated sheet regions disclosed in FIG. 3/Table 1.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone 209623. In one embodiment, antisense sequence is generated internally by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the D-SLAM antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the D-SLAM antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding D-SLAM, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:3942 (1982)), etc.

The antisense nucleic acids of the invention comprise, or alternatively consist of, a sequence complementary to at least a portion of an RNA transcript of a D-SLAM gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded D-SLAM antisense nucleic acids, a single strand of the duplex DNA may thus be tested, or triplex formation may be assayed. The ability to hybridize will depend on both the of complementarity and the length of the antisense nucleic acid Generally, the larger the hybridizing nucleic acid, the more base mismatches with a D-SLAM RNA it may contain and still form a stable duplex (or triplex as the case may be). One skilled in the art can ascertain a tolerable of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of D-SLAM shown in FIGS. 1A–B could be used in an antisense approach to inhibit translation of endogenous D-SLAM mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of D-SLAM mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, liybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcylosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the D-SLAM coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy D-SLAM mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of D-SLAM (FIGS. 1A–B). Preferably, the ribozyme is engineered so that the cleavage recognition site is located near the 5' end of the D-SLAM mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express D-SLAM in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous D-SLAM messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, diagnose, detect, and/or prevent the diseases described herein.

Binding Peptides and Other Molecules

The invention also encompasses screening methods for identifying polypeptides and nonpolypeptides that bind D-SLAM polypeptides, and the D-SLAM binding molecules identified thereby. These binding molecules are useful, for example, as agonists and antagonists of D-SLAM polypeptides. Such agonists and antagonists can be used, in accordance with the invention, in the therapeutic embodiments described in detail, below.

This method comprises the steps of:
  contacting D-SLAM polypeptides or D-SLAM-like polypeptides with a plurality of molecules; and
  identifying a molecule that binds the D-SLAM polypeptides or D-SLAM-like polypeptides.

The step of contacting D-SLAM polypeptides or D-SLAM-like polypeptides with the plurality of molecules may be effected in a number of ways. For example, one may contemplate immobilizing D-SLAM polypeptides or D-SLAM-like polypeptides on a solid support and bringing a solution of the plurality of molecules in contact with the immobilized D-SLAM polypeptides or D-SLAM-like polypeptides. Such a procedure would be akin to an affinity chromatographic process, with the affinity matrix being comprised of the immobilized D-SLAM polypeptides or D-SLAM-like polypeptides. The molecules having a selective affinity for the D-SLAM polypeptides or D-SLAM-like polypeptides can then be purified by affinity selection. The nature of the solid support, process for attachment of the D-SLAM polypeptides or D-SLAM-like polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the D-SLAM polypeptides or D-SLAM-like polypeptides, optionally in the presence of an inducer should one be required for expression, to determine if any selective affinity interaction takes place between the D-SLAM polypeptides or D-SLAM-like polypeptides and the individual clone. Prior to contacting the D-SLAM polypeptides or D-SLAM-like polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for D-SLAM polypeptides or D-SLAM-like polypeptides. Furthermore, the amino acid sequence of the polypeptide having a selective affinity for the D-SLAM polypeptides or D-SLAM-like polypeptides can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound D-SLAM polypeptides or D-SLAM-like polypeptides, or alterntatively, unbound polypeptides, from a mixture of the D-SLAM polypeptides or D-SLAM-like polypeptides and the plurality of polypeptides prior to attempting to determine or to detect the presence of a selective affinity interaction. Such a wash step may be particularly desirable when the D-SLAM polypeptides or D-SLAM-like polypeptides or the plurality of polypeptides is bound to a solid support.

The plurality of molecules provided according to this method may be provided by way of diversity libraries, such as random or combinatorial peptide or nonpeptide libraries which can be screened for molecules that specifically bind D-SLAM polypeptides. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. Nos. 5,096,815, 5,223,409, and 5,198,346, all to Ladner et al.; Rebar and Pabo, 1993, Science 263:671–673; and CT Publication No. WO 94/18318.

In a specific embodiment, screening to identify a molecule that binds D-SLAM polypeptides can be carried out by contacting the library members with a D-SLAM polypeptides or D-SLAM-like polypeptides immobilized on a solid phase and harvesting those library members that bind to the D-SLAM polypeptides or D-SLAM-like polypeptides. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited herein.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to D-SLAM polypeptides or D-SLAM-like polypeptides.

Where the D-SLAM binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a D-SLAM binding molecule that is a polypeptide, the polypeptide may have about 6 to less than about 60 amino acid residues, preferably about 6 to about 10 amino acid residues, and most preferably, about 6 to about 22 amino acids. In another embodiment, a D-SLAM binding polypeptide has in the range of 15–100 amino acids, or 20–50 amino acids.

The selected D-SLAM binding polypeptide can be obtained by chemical synthesis or recombinant expression.

Other Activities

The polypeptide of the present invention, as a result of the ability to stimulate vascular endothelial cell growth, may be employed in treatment, diagnosis, detection, and/or prevention for stimulating re-vascularization of ischemic tissues due to various disease conditions such as thrombosis, arteriosclerosis, and other cardiovascular conditions. These polypeptides may also be employed to stimulate angiogenesis and limb regeneration, as discussed above.

The polypeptide may also be employed for treating, diagnosing, detecting, and/or preventing wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, diagnose, detect, and/or prevent neuronal damage which occurs in certain neuronal disorders or neuro-degenerative conditions such as Alzheimer's disease, Parkinson's disease, and AIDS-related complex. D-SLAM may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The D-SLAM polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The D-SLAM polypeptide may also be employed to maintain organs before transplantation or for supporting cell culture of primary tissues.

The polypeptide of the present invention may also be employed for inducing tissue of mesodermal origin to differentiate in early embryos.

D-SLAM polynucleotides or polypeptides, or agonists or antagonists of D-SLAM, may also increase or decrease the differentiation or proliferation of embryonic stem cells, besides, as discussed above, hematopoietic lineage.

D-SLAM polynucleotides or polypeptides, or agonists or antagonists of D-SLAM, may also be used to modulate mammalian characteristics, such as body height, weight, hair color, eye color, skin, percentage of adipose tissue, pigmentation, size, and shape (e.g., cosmetic surgery). Similarly, D-SLAM polynucleotides or polypeptides, or agonists or antagonists of D-SLAM, may be used to modulate mammalian metabolism affecting catabolism, anabolism, processing, utilization, and storage of energy.

D-SLAM polynucleotides or polypeptides, or agonists or antagonists of D-SLAM, may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

D-SLAM polynucleotides or polypeptides, or agonists or antagonists of D-SLAM, may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

EXAMPLES

Example 1

Isolation of the D-SLAM cDNA Clone from the Deposited Sample

The cDNA for D-SLAM is inserted into the SalI/NotI multiple cloning site of pCMVSport 3.0. (Life Technologies, Inc., P. O. Box 6009, Gaithersburg, Md. 20897.) pCM-VSport 3.0 contains an ampicillin resistance gene and may be transformed into *E. coli* strain DH10B, also available from Life Technologies. (See, for instance, Gruber, C. E., et al., *Focus* 15:59-(1993).)

Two approaches can be used to isolate D-SLAM from the deposited sample. First, a specific polynucleotide of SEQ ID NO:1 with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1 (i.e., within the region of SEQ ID NO:1 bounded by the 5' NT and the 3' NT of the clone) are synthesized and used to amplify the D-SLAM cDNA using the deposited cDNA plasmid as a template. The polymerase chain reaction is carried out under routine conditions, for instance, in 25 µl of reaction mixture with 0.5 ug of the above cDNA template. A convenient reaction mixture is 1.5–5 mM $MgCl_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the D-SLAM gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7): 1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the D-SLAM gene of interest is used to PCR amplify the 5' portion of the D-SLAM full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the D-SLAM gene.

Example 2

Isolation of D-SLAM Genomic Clones

A human genomic P1 library (Genomic Systems, Inc.) is screened by PCR using primers selected for the cDNA sequence corresponding to SEQ ID NO:1., according to the method described in Example 1. (See also, Sambrook.)

Example 3

Tissue Distribution of D-SLAM Polypeptides

Tissue distribution of mRNA expression of D-SLAM is determined using protocols for Northern blot analysis, described by, among others, Sambrook et al. For example, a D-SLAM probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of D-SLAM

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of D-SLAM

D-SLAM polynucleotide encoding a D-SLAM polypeptide invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Alternatively, a construct containing DNA encoding amino acid Q24-D233 of SEQ ID NO:2 can be inserted into pQE70. This construct places a HIS tag (6 histidines) at the C-terminus of the predicted extracellular domain of D-SLAM. Primers that can be used include a 5' primer containing a Sph restriction site, shown in bold: GCAG-CAGCATGCAAGTGCTGAG-CAAAGTCGGGGGCTCGGTGCTG (SEQ ID NO: 14) and a 3' primer, containing a BglII restriction site, shown in bold: GCAGCAAGATCTATCTTTGTAGGAGGC-CTTCCCTGGTGCTGCCTC (SEQ ID NO: 15). This construct uses an ATG as a start codon contained within the SphI site, then reading into Q24 of SEQ ID NO:2, and continues until D233 of SEQ ID NO:2. The amino acid sequence encoded by this construct is as follows:

MQVLSKVGGSVLLVAARPPGFQVREAIWRSLWPSEELLATF
FRGSLETLYHSRFLGRAQLHSNLSLELGPLESGDSGNFSVL
MVDTRGQPWTQTLQLKVYDAVPRPVVQVFIAVERDAQP
SKTCQVFLSCWAPNISEITYSWRRETTMDFGMEPHSL
FTDGQVLSISLGPGDRDVAYSCIVSNPVSWDLATVTPWDS
CHHEAAPGKASYKDQVLSKVGGSVLLVAARPPGFQVRE
AIWRSLWPSEELLATFFRGSLETLYHSRFLGRAQLHSNLS
LELGPLESGDSGNFSVLMVDTRGQPWTQTLQLKVYDA
VPRPVVQVFIAVERDAQPSKTCQVFLSCWAPNISEITYSW
RRETTMDFGMEPHSLFTDGQVLSISLGPGDRDVAYSCIV
SNPVSWDLATVTPWDSCHHEAAPGKASYKDHHH
HHH (SEQ ID NO: 16).

Alternatively, a His tag can be placed on the N-terminus of the predicted mature form containing only the extracellular domain of D-SLAM (e.g., corresponding to A23-D233 of SEQ ID NO:2). In this example, the 5' primer, containing a BamHI restriction site, indicated in bold, can be used:

GCAGCAGGATCCGCCCAAGTGCTGAG-
CAAAGTCGGGGGCTCGGTG (SEQ ID NO: 17) and a 3'
primer, containing a HindIII restriction site, indicated in
bold, can be used:
GCAGCAAAGCTTTTAATCTTTGTAGGAG-
GCCTTCCCTGGTGCTGCC (SEQ ID NO: 18). These
primer can be used to amplify DNA encoding A23-D233,
and then the generated product can be inserted into pQE9.
This construct puts a His tag on the N-terminus of the
predicted mature extracellular domain of D-SLAM. The His
tag will be followed by the Gly-Ser of the BamHI site, and
this will then be followed by A23 of SEQ ID NO:2. This
construct will continue through D233 of SEQ ID NO:2, and
will be followed by a TAA stop codon. The amino acid
sequence encoded by this construct is as follows:

MRGSHHHHHHGSAQVLSKVGGSVLLVAARPPGFQVREAIWRSLWPSEELL

ATFFRGSLETLYHSRFLGRAQLHSNLSLELGPLESGDSGNFSVLMVDTRG

QPWTQTLQLKVYDAVPRPVVQVFIAVERDAQPSKTCQVFLSCWAPNISEI

TYSWRRETTMDFGMEPHSLFTDGQVLSISLGPGDRDVAYSCIVSNPVSWD

LATVTPWDSCHHEAAPGKASYKD (SEQ ID NO:19).

GCAGCACATATGGCCCAAGTGCTGAGCAAAG
TCG                                (SEQ ID NO: 20)

and a 3' primer containing an Asp718 restriction site, shown
in bold, can be used:

GCAGCAGGTACCTTACTAATCTTTGTAG-
GAGGCCTTCCCTGGTGCTGCCTC    (SEQ ID NO: 21).

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 600xg). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6xHis tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified D-SLAM protein is then renatured by dialyzing it against phosphate-buffered saline (PBS) or 50 mM Na-acetate, pH 6 buffer plus 200 mM NaCl. Alternatively, the D-SLAM protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified D-SLAM protein is stored at 4° C. or frozen at −80° C.

In addition to the above expression vector, the present invention further includes an expression vector comprising phage operator and promoter elements operatively linked to a D-SLAM polynucleotide, called pHE4a. (ATCC Accession Number 209645, deposited Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of D-SLAM Polypeptidefrom an Inclusion Body

The following alternative method can be used to purify D-SLAM polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000xg for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000xg centrifugation for 15 min., the pellet is discarded and the polypeptide containing supernatant is incubated at 4° C. overnight to allow further GuHCl extraction.

Following high speed centrifugation (30,000xg) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the D-SLAM polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant D-SLAM polypeptide should exhibit greater than 95% purity after the above refolding and purification steps. No major contaminant bands should be observed from Commassie blue stained 16% SDS-PAGE gel when 5 ug of purified protein is loaded. The purified D-SLAM protein can also be tested for endotoxin/LPS contamination, and typically the LPS content is less than 0.1 ng/ml according to LAL assays.

Example 7

Cloning and Expression of D-SLAM in a Baculovirus Expression System

In this example, the plasmid shuttle vector pA2 is used to insert D-SLAM polynucleotide into a baculovirus to express D-SLAM. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned D-SLAM polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the D-SLAM cDNA sequence contained in the deposited clone, including the AUG initiation codon and any naturally associated leader sequence, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

Fragments of D-SLAM can be expressed from the baculovirus system. For example, the predicted extracellular domain (M1-K232 of SEQ ID NO:2) can be inserted into pA2 using the primers described throughout the Example section.

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced D-SLAM protein.

Example 8

Expression of D-SLAM in Mammalian Cells

D-SLAM polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, D-SLAM polypeptide can be expressed in stable cell lines containing the D-SLAM polynucleotide integrated into a chromosome. The co-transfection with a selectable marker such as DHFR, gpt, neomycin, hygromycin allows the identification and isolation of the transfected cells.

The transfected D-SLAM gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NS0) which are glutamine synthase negative. It is also possible to amplify vectors that utilize glutarnine synthase selection in glutamine synthase expressing cells (e.g., Chinese Hamster Ovary (CHO) cells), however, by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., Bio/technology 10:169(1992) and in Biblia and Robinson Biotechnol. Prog. 11:1 (1995) which are herein incorporated by reference.

Derivatives of the plasmid pSV2-DHFR (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of D-SLAM. The vectors also contain the 3' intron, the polyadenylation and termination signal of the rat preproinsulin gene, and the mouse DHFR gene under control of the SV40 early promoter.

Specifically, the plasmid pC6 or pC4 is digested appropriate restriction enzymes and then dephosphorylated using calf intestinal phosphates by procedures known in the art. The vector is then isolated from a 1% agarose gel.

D-SLAM polynucleotide is amplified according to the protocol outlined in Example 1. If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.)

Specifically, the full length D-SLAM protein can be expressed from a mammalian vector, such as pC4, using the following primers: The 5' primer, containing a BamHI in bold, is as follows:

G C A G C A G G A T C C G C C A T C A T G G T C A T-GAGGCCCCTGTGGAGTCTGCTTCTC (SEQ ID NO:22) while the 3' primer contains a Xba site shown in bold:

G C A G C A T C T A G A T T A T G G C A G A T C C T G-CACAAGGGGGTTCTCTGTC (SEQ ID NO: 23). This construct should produce a transmembrane protein that will be expressed on the external cell surface.

Alternatively, a construct containing only the soluble portion of D-SLAM can be made by inserting the predicted extracellular domain of D-SLAM in pC4. For example, DNA encoding M1-K232 of SEQ ID NO:2 can be in inserted into pC4, using a 5' primer, containing a BamHI restriction site shown in bold:

G C A G C A G G A T C C G C C A T C A T G G T C A T-GAGGCCCCTGTGGAGTCTGCTTCTC (SEQ ID NO: 22) and a 3' primer, containing a Xba restriction site shown in bold:

GCAGCATCTAGATTATTTGTAGGAGGC-
CTTCCCTGGTGCTGCCTC (SEQ ID NO: 24).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel. The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 or pC4 using, for instance, restriction enzyme analysis.

Chinese hamster ovary cells lacking an active DHFR gene is used for transfection. Five µg of the expression plasmid pC6 or pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of D-SLAM is analyzed, for instance, by SDS-PAGE and Western blot or by reversed phase HPLC analysis.

Example 9

Construction of N-Terminal and/or C-Terminal Deletion Mutants

The following general approach may be used to clone a N-terminal or C-terminal deletion D-SLAM deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired D-SLAM polynucleotide fragment. An initiation and stop codon are added to the 5' and 3' primers respectively, if necessary, to express the D-SLAM polypeptide fragment encoded by the polynucleotide fragment. Preferred D-SLAM polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the D-SLAM polynucleotide fragment in a desired vector may also be added to the 5' and 3' primer sequences. The D-SLAM polynucleotide fragment is amplified from genomic DNA or from the deposited cDNA clone using the appropriate PCR oligonucleotide primers and conditions discussed herein or known in the art. The D-SLAM polypeptide fragments encoded by the D-SLAM polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the D-SLAM polypeptide fragment Leu-35 to Thr-276 is amplified and cloned as follows: A 5' primer is generated comprising a restriction enzyme site followed by an initiation codon in frame with the polynucleotide sequence encoding the N-terminal portion of the polypeptide fragment beginning with Leu-35. A complementary 3' primer is generated comprising a restriction enzyme site followed by a stop codon in frame with the polynucleotide sequence encoding C-terminal portion of the D-SLAM polypeptide fragment ending with Thr-276.

The amplified polynucleotide fragment and the expression vector are digested with restriction enzymes which recognize the sites in the primers. The digested polynucleotides are then ligated together. The D-SLAM polynucleotide fragment is inserted into the restricted expression vector, preferably in a manner which places the D-SLAM polypeptide fragment coding region downstream from the promoter. The ligation mixture is transformed into competent E. coli cells using standard procedures and as described in the Examples herein. Plasmid DNA is isolated from resistant colonies and the identity of the cloned DNA confirmed by restriction analysis, PCR and DNA sequencing.

Example 10

Protein Fusions of D-SLAM

D-SLAM polypeptides are preferably fused to other proteins. These fusion proteins can be used for a variety of applications. For example, fusion of D-SLAM polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to D-SLAM polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and D-SLAM polynucleotide, isolated by the PCR protocol described in Example 1, is ligated into this BamHI site. Note that the polynucleotide is cloned without a stop codon, otherwise a fusion protein will not be produced.

Examples of primers that can be used to amplify D-SLAM polypeptides, such as the predicted extracellular domain of D-SLAM include: a 5' primer containing a BamHI restriction site shown in bold: GCAGCAGGATCCGCCATCATGGTCAT- GAGGCCCCTGTGGAGTCTGCTTCTC (SEQ ID NO: 22) and a 3' primer, containing a Xba restriction site shown in bold: GCAGCATCTAGAATCTTTGTAGGAGGC- CTTCCCTGGTGCTGCCTC (SEQ ID NO: 25). Using these primers, the construct will express the predicted extracellular domain of D-SLAM fused to Fe in pC4.

If the naturally occurring signal sequence is used to produce the secreted protein, pC4 does not need a second signal peptide. Alterntatively, if the naturally occurring signal sequence is not used, the vector can be modified to include a heterologous signal sequence. (See, e.g., WO 96/34891.)

Human IgG region:

GGGATCCGGAGCCCAAATCTTCTGACAAAACTCACAC (SEQ ID NO:4)
ATGCCCACCGTGCCCAGCACCTGAATTCGAGGGTGCA
CCGTCAGTCTTCCTCTTCCCCCCAAAACCCAAGGACA
CCCTCATGATCTCCCGGACTCCTGAGGTCACATGCGT
GGTGGTGGACGTAAGCCACGAAGACCCTGAGGTCAAG
TTCAACTGGTACGTGGACGGCGTGGAGGTGCATAATG
CCAAGACAAAGCCGCGGGAGGAGCAGTACAACAGCAC
GTACCGTGTGGTCAGCGTCCTCACCGTCCTGCACCAG
GACTGGCTGAATGGCAAGGAGTACAAGTGCAAGGTCT
CCAACAAAGCCCTCCCAACCCCCATCGAGAAAACCAT
CTCCAAAGCCAAAGGGCAGCCCCGAGAACCACAGGTG
TACACCCTGCCCCCATCCCGGGATGAGCTGACCAAGA
ACCAGGTCAGCCTGACCTGCCTGGTCAAAGGCTTCTA
TCCAAGCGACATCGCCGTGGAGTGGGAGAGCAATGGG
CAGCCGGAGAACAACTACAAGACCACGCCTCCCGTGC
TGGACTCCGACGGCTCCTTCTTCCTCTACAGCAAGCT
CACCGTGGACAAGAGCAGGTGGCAGCAGGGGAACGTC
TTCTCATGCTCCGTGATGCATGAGGCTCTGCACAACC
ACTACACGCAGAAGAGCCTCTCCCTGTCTCCGGGTAA
ATGAGTGCGACGGCCGCGACTCTAGAGGAT

Alternatively, this same region can be inserted in pA2, creating a fusion of Fe with the predicted extracellular domain of D-SLAM. Examples of primer that can be used to amplify the predicted extracellular domain of D-SLAM include: a 5' primer containing a BamHI restriction site shown in bold: GCAGCAGGATCCGCCATCATGGTCAT- GAGGCCCCTGTGGAGTCTGCTTCTC (SEQ ID NO: 22) and a 3' primer, containing a Xba restriction site shown in bold: GCAGCATCTAGAATCTTTGTAGGAGGC- CTTCCCTGGTGCTGCCTC (SEQ ID NO: 25). This construct will express the predicted extracellular domain of D-SLAM fused to Fc in pA2.

These two above constructs were expressed in their appropriate host cells (e.g., pC4 in a mammalian system, while pA2 in a baculovirus system), both systems produced a truncated protein, lacking the predicted signal sequence and beginning with A23 of SEQ ID NO:2. Thus, as was predicted, both baculovirus and mammalian systems process D-SLAM to amino acid A23 of SEQ ID NO:2. However, due to differences in glycosylation, the baculovirus system produces a protein, under reducing conditions, migrating at around 60 kD, while the mammalian system generates a protein migrating at around 55 kD.

Additionally, fusion proteins of D-SLAM polypeptides, including the predicted extracellular domain or the mature form of D-SLAM, can be fused to FLAG for mammalian cell expression. For example, the extracellular domain can be amplifed using the following primers: a 5' primer containing a BamHI restriction site shown in bold: GCAGCAG- GATCCGCCATCATGGTCATGAGGCCCCT- GTGGAGTCTGCTTCTC (SEQ ID NO: 22) and a 3' primer, containing a Xba restriction site shown in bold:

GCAGCATCTAGATTACTTGTCATCGTCGTCCTTGTAGTCATCTTTGTAGG
AGGCCFTCCCTGGTGCTG (SEQ ID NO:26).

Example 11

Production of an Antibody a) Hybridoma Technology

The antibodies of the present invention can be prepared by a variety of methods. (See, Current Protocols, Chapter 2.) As one example of such methods, cells expressing D-SLAM is administered to an animal to induce the production of sera containing polyclonal antibodies. In a preferred method, a preparation of D-SLAM protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with D-SLAM polypeptide or, more preferably, with a secreted D-SLAM polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the D-SLAM polypeptide.

Alternatively, additional antibodies capable of binding to D-SLAM polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the D-SLAM protein-specific antibody can be blocked byD-SLAM. Such antibodies comprise anti-idiotypic antibodies to the D-SLAM protein-specific antibody and can be used to immunize an animal to induce formation of further D-SLAM protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted D-SLAM protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643(1984); Neuberger et al., Nature 314:268(1985).)

b) Isolation of Antibody Fragments Directed Against D-SLAM from a Library of scFvs Naturally occuring V-genes isolated from human PBLs are constructed into a large library of antibody fragments which contain reactivities against D-SLAM to which the donor may or may not have been exposed (see e.g., U.S. Pat. No. 5,885,793 incorporated herein in its entirety by reference).

Rescue of the Library.

A library of scFvs is constructed from the RNA of human PBLs as described in WO92/01047. To rescue phage displaying antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2\times10^8$ TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library.

Immunotubes (Nunc) are coated overnight in PBS with 4 ml of either 100 ug/ml or 10 ug/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders.

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 12

Production Of D-SLAM Protein For High-Throughput Screening Assays

The following protocol produces a supernatant containing D-SLAM polypeptide to be tested. This supernatant can then be used in the Screening Assays described in Examples 14–21.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Opti-mem I (31985070 Gibco/BRL)/96-well plate. With a small volume multi-channel pipetter, aliquot approximately 2 ug of an expression vector containing a polynucleotide insert, produced by the methods described in Examples 8–10, into an appropriately labeled 96-well round bottom plate. With a multi-channel pipetter, add 50ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1%BSA in DMEM with 1×penstrep, or HGS CHO-5 media (116.6 mg/L of $CaCl2$ (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of ween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2$H_2O$; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1×penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfoction media, while person B adds 1.5 ml appropriate media to each well. Incubate at 37° C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 14–21.

It is specifically understood that when activity is obtained in any of the assays described below using a supernatant, the activity originates from either the D-SLAM polypeptide directly (e.g., as a secreted protein) or by D-SLAM inducing expression of other proteins, which are then secreted into the supernatant. Thus, the invention further provides a method of identifying the protein in the supernatant characterized by an activity in a particular assay.

Example 13

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-D-SLAM-Trp-Ser (SEQ ID NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

early promoter sequence and is flanked with an XhoI site. The sequence of the 5' primer is:

5':GCGCCTCGAGATTTCCCCGAAATCTAGATTTCCCCG
AAATGATTTCCCCGAAATGATTTCCCCGAAATATCTGC
CATCTCAATTAG:3' (SEQ ID NO:6).

The downstream primer is complementary to the SV40 promoter and is flanked with a Hind III site:

5':GCGGCAAGCTTTTTGCAAAGCCTAGGC:3' (SEQ ID NO:7).

PCR amplification is performed using the SV40 promoter template present in the B-gal:promoter plasmid obtained

| Ligand | JAKs | | | | STATS | GAS(elements) or ISRE |
|---|---|---|---|---|---|---|
| | tyk2 | Jak1 | Jak2 | Jak3 | | |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotrohic) | + | + | + | ? | 1, 3 | GAS (IRF1 > Lys6 > IFP) |
| Il-11(Pleiotrohic) | ? | + | ? | ? | 1, 3 | |
| OnM(Pleiotrohic) | ? | + | + | ? | 1, 3 | |
| LIF(Pleiotrohic) | ? | + | + | ? | 1, 3 | |
| CNTF(Pleiotrohic) | −/+ | + | + | ? | 1, 3 | |
| G-CSF(Pleiotrohic) | ? | + | ? | ? | 1, 3 | |
| IL-12(Pleiotrohic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(1gH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF(myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS (B − CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 14–15, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 from Clontech. The resulting PCR fragment is digested with XhoI/Hind III and subcloned into BLSK2-. (Stratagene.) Sequencing with forward and reverse primers confirms that the insert contains the following sequence:

5':<u>CTCGAG</u>ATTTCCCCGAAATCTAGATTTCCCCGAAATGATTTCCCCGA

AATGATTTCCCCGAAATATCTGCCATCTCAATTAGTCAGCAACCATAGTC

CCGCCCCTAACTCCGCCCATCCCGCCCCTAACTCCGCCCAGTTCCGCCCA

-continued

TTCTCCGCCCCATGGCTGACTAATTTTTTTTATTTATGCAGAGGCCGAGG

CCGCCTCGGCCTCTGAGCTATTCCAGAAGTAGTGAGGAGGCTTTTTTGGA

GGCCTAGGCTTTTGCAAAAAGCTT:3'(SEQ ID NO:8).

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 14–15.

Other constructs can be made using the above description and replacing GAS with a different promoter sequence. For example, construction of reporter molecules containing NFK-B and EGR promoter sequences are described in Examples 16 and 17. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 14

High-Throughput Screening Assay for T-cell Activity

The following protocol is used to assess T-cell activity of D-SLAM by determining whether D-SLAM supernatant proliferates and/or differentiates T-cells. T-cell activity is assessed using the GAS/SEAP/Neo construct produced in Example 13. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing D-SLAM polypeptides or D-SLAM induced polypeptides as produced by the protocol described in Example 12.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 18. The plates containing the remaining treated cells are placed at 4 C and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 15

High-Throughput Screening Assay: Identifying Myeloid Activity

The following protocol is used to assess myeloid activity of D-SLAM by determining whether D-SLAM proliferates and/or differentiates myeloid cells. Myeloid cell activity is assessed using the GAS/SEAPNeo construct produced in Example 13. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAPINeo construct produced in Example 13, a DEAE-Dextran method (Kharbanda et. al., 1994, Cell Growth & Differentiation, 5:259–265) is used. First, harvest 2×10e7 U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 C for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1×10^8$ cells (this is enough for ten 96-well plates assay) and wash with PBS. Suspend the cells in 200 ml above described growth medium, with a final density of $5×10^5$ cells/ml. Plate 200 ul cells per well in the 96-well plate (or $1×10^5$ cells/well).

Add 50 ul of the supernatant prepared by the protocol described in Example 12. Incubate at 37 degee C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 18.

Example 16

High-Throughput Screening Assay: Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by D-SLAM.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by D-SLAM can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

5' GCGCTCGAGGGATGACAGCGATAGAACCCCGG-3' (SEQ ID NO: 9) and

5'GCGAAGCTTCGCGACTCCCCGGATCCGCCTC-3' (SEQ ID NO: 10).

Using the GAS:SEAP/Neo vector produced in Example 13, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 12. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as 5×105 cells/ml.

Add 200 ul of the cell suspension to each well of 96-well plate (equivalent to 1×105 cells/well). Add 50 ul supernatant produced by Example 12, 37 C for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 18.

Example 17

High-Throughput Screening Assayfor T-cell Activity

NF-KB (Nuclear Factor-kappaB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-kappaB regulates the expression of genes involved in immune cell activation, control of apoptosis (NF-kappaB appears to shield cells from apoptosis), B and T-cell development, anti-viral and antimicrobial responses, and multiple stress responses.

In non-stimulated conditions, NF-kappaB is retained in the cytoplasm with I-kappaB (Inhibitor kappaB). However, upon stimulation, I-kappaB is phosphorylated and degraded, causing NF-kappaB to shuttle to the nucleus, thereby activating transcription of target genes. Target genes activated by NF-kappaB include IL-2, IL-6, GM-CSF, ICAM-1 and class 1 MHC.

Due to its central role and ability to respond to a range of stimuli, reporter constructs utilizing the NF-kappaB promoter element are used to screen the supernatants produced in Example 12. Activators or inhibitors of NF-kappaB would be useful in treating, diagnosing, detecting, and/or preventing diseases. For example, inhibitors of NF-kappaB could be used to treat, diagnose, detect, and/or prevent those diseases related to the acute or chronic activation of NF-kappaB, such as rheumatoid arthritis.

To construct a vector containing the NF-kappaB promoter element, a PCR based strategy is employed. The upstream primer contains four tandem copies of the NF-kappaB binding site (GGGGACTTTCCC) (SEQ ID NO:11), 18 bp of sequence complementary to the 5' end of the SV40 early promoter sequence, and is flanked with an XhoI site:

5'GCGGCCTCGAGGGGACTTTCCCGGGGACTTTCCGGGGACTTTCCGGGA
CTTTCCATCCTGCCATCTCAATTAG3' (SEQ ID NO:12).

The downstream primer is complementary to the 3' end of the SV40 promoter and is flanked with a Hind III site:
5'-GCG GCA AGC TTT TTG CAA AGC CTA GGC-3' (SEQ ID NO:7).

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5'CTCGAGGGGACTTTCCCGGGGACTTTCCGGGGACTTTCCGGGACTTTC

CATCTGCCATCTCAATTAGTCAGCAACCATAGTCCCGCCCCTAACTCGCC

CATCCCGCCCCTAACTCCGCCCAGTTCCGCCCATTCTCCGCCCCATGGCT

GACTAATTTTTTTTATTTATGCAGAGGCCGAGGCCGCCTCGGCCTCTGAG

CTATTCCAGAAGTAGTGAGGAGGCTTTTTTGGAGGCCTAGGCTTTTGCAA

AAAGCTT3' (SEQ ID NO:13).

Next, replace the SV40 minimal promoter element present in the pSEAP2-promoter plasmid (Clontech) with this NF-kappaB/SV40 fragment using XhoI and HindIII. However, this vector does not contain a neomycin resistance gene, and therefore, is not preferred for mammalian expression systems.

In order to generate stable mammalian cell lines, the NF-kappaB/SV40/SEAP cassette is removed from the above NF-kappaB/SEAP vector using restriction enzymes SalI and NotI, and inserted into a vector containing neomycin resistance. Particularly, the NF-kappaB/SV40/SEAP cassette was inserted into pGFP-1 (Clontech), replacing the GFP gene, after restricting pGFP-1 with SalI and NotI.

Once NF-kappaB/SV40/SEAP/Neo vector is created, stable Jurkat T-cells are created and maintained according to the protocol described in Example 14. Similarly, the method for assaying supernatants with these stable Jurkat T-cells is also described in Example 14. As a positive control, exogenous TNF alpha (0.1,1, 10 ng) is added to wells H9, H10, and H11, with a 5–10 fold activation typically observed.

Example 18

Assay for SEAP Activity

As a reporter molecule for the assays described in Examples 14–17, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 ul of 2.5×dilution buffer into Optiplates containing 35 ul of a supernatant. Seal the plates with a plastic sealer and incubate at 65 C for 30 min. Separate the Optiplates to avoid uneven heating.

Cool the samples to room temperature for 15 minutes. Empty the dispenser and prime with the Assay Buffer. Add 50 microliters Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| | Reaction Buffer Formulation: | |
| --- | --- | --- |
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |

-continued

Reaction Buffer Formulation:

| # of plates | Rxn buffer diluent (ml) | CSPD (ml) |
|---|---|---|
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 19

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37 C in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37 C water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either D-SLAM or a molecule induced by D-SLAM, which has resulted in an increase in the intracellular $Ca^{++}$ concentration.

Example 20

High-Throughput Screening Assay: Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether D-SLAM or a molecule induced by D-SLAM is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 C Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 12, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeberinger Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 C at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSKI (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5×Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30 C for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 C for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37 C for one hour. Wash the well as above.

Next add 100 ul of peroxidase substrate solution (Boehringer Marnheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 21

High-Throughput Screening Assay Identifying Phosphorylation Activity

As a potential alternative and/or compliment to the assay of protein tyrosine kinase activity described in Example 20, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, INK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 C until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 12 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallace DELFIA instrument (time-resolved fluorescence). An increased fluorescent signal over background indicates a phosphorylation by D-SLAM or a molecule induced by D-SLAM.

Example 22

Method of Determining Alterations in the D-SLAM Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 C for 30 seconds; 60–120 seconds at 52–58 C; and 60–120 seconds at 70 C, using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of D-SLAM is also determined and genomic PCR products analyzed to confirm the results. PCR products harboring suspected mutations in D-SLAM is then cloned and sequenced to validate the results of the direct sequencing.

PCR products of D-SLAM are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in D-SLAM not present in unaffected individuals.

Genomic rearrangements are also observed as a method of determining alterations in the D-SLAM gene. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the D-SLAM genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cg. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of D-SLAM (hybridized by the probe) are identified as insertions, deletions, and translocations. These D-SLAM alterations are used as a diagnostic marker for an associated disease.

Example 23

Method of Detecting Abnormal Levels of D-SLAM in a Biological Sample

D-SLAM polypeptides can be detected in a biological sample, and if an increased or decreased level of D-SLAM is detected, this polypeptide is a marker for a particular phenotype. Methods of detection are numerous, and thus, it is understood that one skilled in the art can modify the following assay to fit their particular needs.

For example, antibody-sandwich ELISAs are used to detect D-SLAM in a sample, preferably a biological sample. Wells of a microtiter plate are coated with specific antibodies to D-SLAM, at a final concentration of 0.2 to 10 ug/ml. The antibodies are either monoclonal or polyclonal and are produced by the method described in Example 11. The wells are blocked so that non-specific binding of D-SLAM to the well is reduced.

The coated wells are then incubated for >2 hours at RT with a sample containing D-SLAM. Preferably, serial dilutions of the sample should be used to validate results. The plates are then washed three times with deionized or distilled water to remove unbounded D-SLAM.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot D-SLAM polypeptide concentration on the X-axis (log scale) and fluorescence or absorbance of the Y-axis (linear scale). Interpolate the concentration of the D-SLAM in the sample using the standard curve.

Example 24

Formulating a Polypeptide

The D-SLAM composition will be formulated and dosed in a fashion consistent with good medical practice, taking into account the clinical condition of the individual patient (especially the side effects of treatment with the D-SLAM polypeptide alone), the site of delivery, the method of administration, the scheduling of administration, and other factors known to practitioners. The "effective amount" for purposes herein is thus determined by such considerations.

As a general proposition, the total pharmaceutically effective amount of D-SLAM administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, D-SLAM is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to D-SLAM polypeptide during therapy may also play an important role in determining a therapeutically and/or pharmacologically effective dosing regime. Variations of dosing such as repeated administrations of a relatively low dose of D-SLAM polypeptide for a relatively long period of time may have an effect which is therapeutically and/or pharmacologically distinguishable from that achieved with repeated administrations of a relatively high dose of D-SLAM for a relatively short period of time.

Using the equivalent surface area dosage conversion factors supplied by Freireich, E. J., et al. (*Cancer Chemotherapy Reports* 50(4):219–44 (1966)), one of ordinary skill in the art is able to conveniently convert data obtained from the use of D-SLAM in a given experimental system into an accurate estimation of a pharmaceutically effective amount of D-SLAM polypeptide to be administered per dose in another experimental system. Experimental data obtained through the administration of D-SLAM may converted through the conversion factors supplied by Freireich, et al., to accurate estimates of pharmaceutically effective doses of D-SLAM in rat, monkey, dog, and human. The following conversion table (Table III) is a summary of the data provided by Freireich, et al. Table III gives approximate factors for converting doses expressed in terms of mg/kg from one species to an equivalent surface area dose expressed as mg/kg in another species tabulated.

TABLE III

Equivalent Surface Area Dosage Conversion Factors.

| --FROM-- | --TO-- | | | | |
| --- | --- | --- | --- | --- | --- |
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Human | 12 | 7 | 3 | 2 | 1 |

Thus, for example, using the conversion factors provided in Table III, a dose of 50 mg/kg in the mouse converts to an appropriate dose of 12.5 mg/kg in the monkey because (50 mg/kg)×(1/4)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

Pharmaceutical compositions containing D-SLAM are administered orally, rectally, parenterally, intracisternally, intravaginally, intraperitoneally, topically (as by powders, ointments, gels, drops or transdermal patch), bucally, or as an oral or nasal spray. In one embodiment, "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The term "parenteral" as used herein refers to modes of administration which include intravenous, intramuscular, intraperitoneal, intrasternal, subcutaneous and intraarticular injection and infusion.

In a preferred embodiment, D-SLAM compositions of the invention (including polypeptides, polynucleotides, and antibodies, and agonists and/or antagonists thereof) are administered subcutaneously.

In another preferred embodiment, D-SLAM compositions of the invention (including polypeptides, polynucleotides, and antibodies, and agonists and/or antagonists thereof) are administered intravenously.

D-SLAM compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988).

In a preferred embodiment, D-SLAM compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO01/24374, and WO00/06117 which are hereby incorporated by reference in their entirety. In specific preferred embodiments the D-SLAM compositions of the invention are formulated using the ATRIGEL® Biodegradable System of Atrix Laboratories, Inc. (Fort Collins, Colo.).

Examples of biodegradable polymers which can be used in the formulation of D-SLAM compositions, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of D-SLAM compositions are poly(lactide-co-glycolides). Polymer properties such as molecular weight, hydrophobicity, and lactide/glycolide ratio may be modified to obtain the desired drug D-SLAM release profile (See, e.g., Ravivarapu et al., Journal of Pharmaceutical Sciences 89:732–741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alchohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alchohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising D-SLAM compositions and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$-$C_{12}$ alkanols, 2-ethoxyethanol. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the D-SLAM compositions of the invention are formulated using the BEMA™ BioErodible Mucoadhesive System, MCA™ MucoCutaneous Absorption System, SMP™ Solvent MicroParticle System, or BCP™ BioCompatible Polymer System of Atrix Laboratories, Inc. (Fort Collins, Colo.).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing D-SLAM polypeptide my be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal D-SLAM polypeptide therapy.

In another embodiment systained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, D-SLAM is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting D-SLAM uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

D-SLAM is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

D-SLAM used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

D-SLAM polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous D-SLAM polypeptide solution, and the resulting mixture is lyophilized. The infusion solution is prepared by reconstituting the lyophilized D-SLAM polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, D-SLAM may be employed in conjunction with other therapeutic compounds.

The compositions of the invention may be administered alone or in combination with other therapeutic agents. Therapeutic agents that may be administered in combination with the compositions of the invention, include but not limited to, members of the TNF family (e.g., Neutrokine-Alpha and/or Neutrokine-AlphaSV (International Application No. PCT/US96/7957) or antagonists thereof), chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus Enterococcus and/or the genus Streptococcus. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/or condition associated with *Streptococcus pneumoniae*.

The compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In a specific embodiment, the compositions of the invention are administered in combination with antagonists of co-activators of B cells (e.g., Neutrokine-Alpha and/or Neutrokine-AlphaSV (International Application No. PCT/US96/17957), BLyS, BAFF, TALL-1, THANK, and/or zTNF4). In a further embodiment, antagonists may include, but are not limited to, antibodies directed to and/or the soluble extracellular portion of the Neutokine-Alpha and/or Neutrokine-AlphaSV receptor, the BLyS receptor, the BAFF receptor, the TALL-1 receptor, the THANK receptor, TACI, and/or BCMA.

In one embodiment, the compositions of the invention are administered in combination with other members of the TNF family. TNF, TNF-related or TNF-like molecules that may be administered with the compositions of the invention include, but are not limited to, soluble forns of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), AIM-I (International Publication No. WO 97/33899), endokine-alpha (International Publication No. WO 98/07880), Neutrokine-Alpha and/or Neutrokine-AlphaSV (International Application No. PCT/US96/17957), TR6 (International Publication No. WO 98/30694), OPG, OX40, nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In a preferred embodiment, the compositions of the invention are administered in combination with CD40 ligand (CD40L), a soluble form of CD40L (e.g., AVRENDT™), biologically active fragments, variants, or derivatives of CD40L, anti-CD40L antibodies (e.g,. agonistic or antagonistic antibodies), and/or anti-CD40 antibodies (e.g, agonistic or antagonistic antibodies).

In another embodiment, compositions of the invention are administered in combination with an anticoagulant. Anticoagulants that may be administered with the compositions of the invention include, but are not limited to, heparin, warfarin, and aspirin. In a specific embodiment, compositions of the invention are administered in combination with heparin and/or warfarin. In another specific embodiment, compositions of the invention are administered in combination with warfarin. In another specific embodiment, compositions of the invention are administered in combination with warfarin and aspirin. In another specific embodiemtn, compositions of the invention are administered in combination with heparin. In another specific embodiemtn, compositions of the invention are administered in combination with heparin and aspirin.

In another embodiment, compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RFTROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVANT™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostirn/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonarnide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs cyclophospharnide, cyclophosphamide IV, methylprednisolone, prednisolone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/ NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs:

NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.), and prednisolone.

In a more preferred embodiment, the compositions of the invention are administered in combination with an antimalarial, methotrexate, anti-TNF antibody, ENBRELT™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBRELT™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specfic embodiment, the compositions of the invention are administered in combination with an antimalarial (e.g., hydroxychloroquine), ENBRELT™, methotrexate and suflasalazine. In another specfic embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutanic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, compositions of the invention may be administered with any interleukin, including, but not limited to, IL-1alpha, IL-1beta, IL-2, IL-3, IL-4, IL-5, IL-6, IL-7, IL-8, L-9, IL-10, IL-11, IL-12, IL-13, IL-14, IL-15, IL-16, IL-17, IL-18, IL-19, L-20, IL-21, and L-22. In preferred embodiments, the compositions of the invention are administered in combination with IL4 and L10. Both IL4 and L10 have been observed by the inventors to enhance D-SLAM-mediated B cell proliferation.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble L-4 receptor polypeptides, multimeric forms of soluble IL4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIMT™) and NEUPOGEN™ (FILGRASTIM™).

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered alone or in combination with other therapeutic or prophylactic regimens, including but not limited to, radiation therapy. Such combinatorial therapy may be administered sequentially and/or concomitantly.

Example 25

Method of Treating Decreased Levels of D-SLAM

The present invention relates to a method for treating an individual in need of a decreased level of D-SLAM activity in the body comprising, administering to such an individual a composition comprising a therapeutically effective amount of D-SLAM antagonist. Preferred antagonists for use in the present invention are D-SLAM-specific antibodies.

Moreover, it will be appreciated that conditions caused by a decrease in the standard or normal expression level of D-SLAM in an individual can be treated by administering D-SLAM, preferably in the secreted form. Thus, the invention also provides a method of treatment of an individual in need of an increased level of D-SLAM polypeptide comprising administering to such an individual a pharmaceutical composition comprising an amount of D-SLAM to increase the activity level of D-SLAM in such an individual.

For example, a patient with decreased levels of D-SLAM polypeptide receives a daily dose 0.1–100 ug/kg of the polypeptide for six consecutive days. Preferably, the polypeptide is in the secreted form. The exact details of the dosing scheme, based on administration and formulation, are provided in Example 24.

Example 26

Method of Treating Increased Levels of D-SLAM

The present invention also relates to a method for treating an individual in need of an increased level of D-SLAM activity in the body comprising administering to such an individual a composition comprising a therapeutically effective amount of D-SLAM or an agonist thereof.

Antisense technology is used to inhibit production of D-SLAM. This technology is one example of a method of decreasing levels of D-SLAM polypeptide, preferably a secreted form, due to a variety of etiologies, such as cancer.

For example, a patient diagnosed with abnormally increased levels of D-SLAM is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 24.

Example 27

Method of Treatment Using Gene Therapy—Ex Vivo

One method of gene therapy transplants fibroblasts, which are capable of expressing D-SLAM polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 C for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding D-SLAM can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted D-SLAM.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the D-SLAM gene is then added to the media and the packaging cells transduced with the vector. The packaging cells now produce infectious viral particles containing the D-SLAM gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether D-SLAM protein is produced.

The engineered fibroblasts are then transplanted onto the host, either alone or after having been grown to confluence on cytodex 3 microcarrier beads.

Example 28

Gene Therapy Using Endogenous D-SLAM Gene

Another method of gene therapy according to the present invention involves operably associating the endogenous D-SLAM sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous D-SLAM, flanking the promoter. The targeting sequence will be sufficiently near the 5' end of D-SLAM so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous D-SLAM sequence. This results in the expression of D-SLAM in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the D-SLAM locus, plasmid pUC18 (MBI Fermentas, Amherst, N.Y.) is digested with HindIII. The CMV promoter is amplified by PCR with an XbaI site on the 5' end and a BamHI site on the 3'end. Two D-SLAM non-coding sequences are amplified via PCR: one D-SLAM non-coding sequence (D-SLAM fragment 1) is amplified with a HindIiI site at the 5' end and an Xba site at the 3'end; the other D-SLAM non-coding sequence (D-SLAM fragment 2) is amplified with a BamHI site at the end and a HindIII site at the 3'end. The CMV promoter and D-SLAM fragments are digested with the appropriate enzymes (CMV promoter—XbaI and BamHI; D-SLAM fragment 1—XbaI; D-SLAM fragment 2—BamHI) and ligated together. The resulting ligation product is digested with HindIll, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5. \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 29

Method of Treatment Using Gene Therapy—In Vivo

Another aspect of the present invention is using in vivo gene therapy methods to treat, diagnose, detect, and/or prevent disorders, diseases and conditions. The gene therapy method relates to the introduction of naked nucleic acid (DNA, RNA, and antisense DNA or RNA) D-SLAM sequences into an animal to increase or decrease the expression of the D-SLAM polypeptide. The D-SLAM polynucleotide may be operatively linked to a promoter or any other genetic elements necessary for the expression of the D-SLAM polypeptide by the target tissue. Such gene therapy and delivery techniques and methods are known in the art, see, for example, WO 90/11092, WO 98/11779; U.S. Pat. No. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The D-SLAM polynucleotide constructs may be delivered by any method that delivers injectable materials to the cells of an animal, such as, injection into the interstitial space of tissues (heart, muscle, skin, lung, liver, intestine and the like). The D-SLAM polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the D-SLAM polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The D-SLAM polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The D-SLAM polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked D-SLAM polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked D-SLAM polynucleotide constructs can be delivered to arteries during angioplasty by the catheter used in the procedure.

The dose response effects of injected D-SLAM polynucleotide in muscle in vivo is determined as follows. Suitable D-SLAM template DNA for production of mRNA coding for D-SLAM polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The D-SLAM template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fiflh 15 um cross-section of the individual quadriceps muscles is histochemically stained for D-SLAM protein expression. A time course for D-SLAM protein expression may be done in a similar fashion except that quadriceps from different mice are harvested at different times. Persistence of D-SLAM DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using D-SLAM naked DNA.

Example 30

D-SLAM Transgenic Animals

The D-SLAM polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Any of the D-SLAM polypeptides disclose throughout this application can be used to generate transgenic animals. For example, DNA encoding amino acids M1-K232 of SEQ ID NO:2 can be inserted into a vector containing a promoter, such as the actin promoter, which will ubiquitously express the inserted fragment. Primers that can be used to generate such fragments include a 5' primer containing a BamHI restriction site shown in bold:

G C AG C AG G AT C C G C C AT C AT G G T C AT-GAGGCCCCTGTGGAGTCTGCTTCTC (SEQ ID NO: 22) and a 3' primer, containing a Xba restriction site shown in bold:

G C A G C ATC TAG ATTAT T T G TAG G AG G C-CTTCCCTGGTGCTGCCTC (SEQ ID NO: 24). This construct will express the predicted extracellular domain of D-SLAM under the control of the actin promoter for ubiquitous expression. The region of D-SLAM included in this construct extends from M1-K232 of SEQ ID NO:2.

Similarly, the DNA encoding the full length D-SLAM protein can also be inserted into a vector using the following primers: A 5' primer containing a BamHI restriction site shown in bold:

G C AG C AG G AT C C G C C AT C AT G G T C AT-GAGGCCCCTGTGGAGTCTGCTTCTC (SEQ ID NO: 22) and a 3' primer, containing a Xba restriction site shown in bold:

G C A G C ATC TAG AT TAT G G C AG AT C C T G - CACAAGGGGGTTCTCTGTC (SEQ ID NO: 23). Besides these two examples, other fragments of D-SLAM can also be inserted into a vector to create transgenics having ubiquitous expression.

Alternatively, polynucleotides of the invention can be inserted in a vector which controls tissue specific expression through a tissue specific promoter. For example, a construct having a transferrin promoter would express the D-SLAM polypeptide in the liver of transgenic animals. Therefore, DNA encoding amino acids M1-K232 of SEQ ID NO:2 can be amplified using a 5' primer, having a BamHI restriction site shown in bold:

GCAGCAGGATCCGCCATCATGGTCAT-GAGGCCCCTGTGGAGTCTGCTTCTC (SEQ ID NO: 22), and a 3' primer, containing a Xba restriction site shown in bold:

GCAGCATCTAGATTATTTGTAGGAGGC-CTTCCCTGGTGCTGCCTC (SEQ ID NO: 24).

Similarly, the DNA encoding the full length D-SLAM protein can also be inserted into a vector for tissue specific expression using the following primers: A 5' primer containing a BamHI restriction site shown in bold:

GCAGCAGGATCCGCCATCATGGTCAT-GAGGCCCCTGTGGAGTCTGCTTCTC (SEQ ID NO: 22) and a 3' primer, containing a Xba restriction site shown in bold:

GCAGCATCTAGATTATGGCAGATCCTG-CACAAGGGGGTTCTCTGTC (SEQ ID NO: 23).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of D-SLAM polypeptides, studying conditions and/or disorders associated with aberrant D-SLAM expression, and in screening for compounds effective in ameliorating such conditions and/or disorders.

Example 31

D-SLAM Knock-Out Animals

Endogenous D-SLAM gene expression can also be reduced by inactivating or "knocking out" the D-SLAM gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

For example, a targeting vector can be created which incorporates fragments of the murine D-SLAM locus flanking a Neomyocin cassette. The two flanking regions are generated using the following primers. For the 5' ARM flanking region:

5' ARM primer F: 5'AGCC GGTACCTCCGATGTGCATAATCAGGCT 3'(SEQ ID NO:27), with an Asp718 restriction site underlined; and 5' ARM primer R: 5' GCTTG GCGCGCCCCTGGTTAGTCTGCCTATGTA 3'(SEQ ID NO:28) with a BssH II restriction site underlined. For the 3' ARM flanking region:

3' ARM primer F: 5'ATCC ATCGATCCACCAAGATTCACAGGCTTG 3' (SEQ ID NO:29) with a Cla I restriction site underlined; and 3' ARM primer R: 5'ATAAGAAT GCGGCCGCAAGGGCTATGCAAGCTTGGCT 3' (SEQ ID NO:30) with a Not I restriction site underlined.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the D-SLAM polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of D-SLAM polypeptides, studying conditions and/or disorders associated with aberrant D-SLAM expression, and in screening for compounds effective in ameliorating such conditions and/or disorders.

Example 32

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell Co.-stimulatory proteins is the TNF-superfamily. Within this family CD40, CD27, and CD30 along with their respective ligands CD154, CD70, and CD153 have been found to regulate a variety of immune responses. Dendritic cells are known to directly interact with B cells and regulate mature B cell responses at various stages of their differentiation. Thus, D-SLAM polypeptides of the invention were tested for their ability to affect B cell proliferation. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay

Purified D-SLAM protein, or truncated forms thereof, is assessed for its ability to induce activation, proliferation, differentiation or inhibition and/or death in B-cell populations and their precursors. Specifically, purified recombinant D-SLAM was assessed for its ability to inhibit proliferation of B cells in a standard Co.-stimulatory assay in which purified tonsillar B cells are cultured in the presence of anti-human IgM or pansorbin as priming agents (Sieckmann, D. G., et al., J.Exp.Med. 147:814–29 (1978); Ringden, O., et al., Scand.J.Immunol. 6:1159–69 (1977)). The activity of D-SLAM protein on purified human tonsillar B cells, measured qualitatively over the dose range from 0.1 to 10,000 ng/mL, is assessed in a standard B-lymphocyte Co.-stimulation assay in which purified tonsillar B cells are cultured in the presence of either formalin-fixed $Staphylococcus$ $aureus$ Cowan I (SAC) or immobilized anti-human IgM antibody as the priming agent. Second signals such as IL-2 and IL-15 synergize with SAC (Pansorbin) and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5 \times 10^{-5}$ M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

B lymphocyte proliferation assay of D-SLAM.

Human tonsillar B cells were purified by magnetic bead (MACS) depletion of CD3-positive cells. The resulting cell population was routinely greater than 95% B cells as assessed by expression of CD19 and CD20. Various dilutions of human recombinant D-SLAM or D-SLAM.Fc (M1-D233 of SEQ ID NO:2 fused to the Fc portion) were placed into individual wells of a 96-well plate to which was added $10^5$ B cells suspended in culture medium (RPMI 1640 containing 10% FBS, $5 \times 10^{-5}$ M 2ME, 100 U/ml penicillin, 100 microgram/ml streptomycin, and $10^{-5}$ dilution of Pansorbin (SAC) or anti-IgM) in a total volume of 150 microliters. Proliferation was quantitated by a 20 h pulse (1 microCi/well) of $^3$H-thymidine (6.7 Ci/mM) beginning 72 h post factor addition.

Results:

Treatment of B cell cultures stimulated to proliferate with either anti-human IgM or with pansorbin with recombinant D-SLAM or D-SLAM.Fc resulted in a dose-dependent inhibition of tonsillar B cell proliferation. A dose-dependent response is readily observed as the amount of crosslinking agent increases in the presence of a fixed concentration of recombinant D-SLAM. Under the same assay conditions, TR9.Fc, an unrelated Fc fusion protein, demonstrated no inhibition.

D-SLAM agonists of the invention may also be examined in this B lymphocyte proliferation assay. In addition, one skilled in the art could easily modify the exemplified studies to test the activity of D-SLAM polynucleotides (e.g., gene therapy) and/or antagonists of D-SLAM.

Antagonists (e.g., including, but not limited to, D-SLAM polypeptide fragments, antibodies directed to D-SLAM or fragments thereof) according to the invention exhibit a increased B cell proliferation when compared to controls containing the same number of B cells and the same concentration of priming agent, and the same concentration of a soluble form of an agent that elicits an increase in B cell proliferative activity in the absence of the antagonist. Agonists (e.g., including but not limited to antibodies directed to D-SLAM, or fragments thereof) demonstrate an decreased B cell proliferation when compared to that observed when the same number of B cells is contacted with the same concentration of priming agent.

In Vivo Assay

BALB/c mice are injected (i.p.) twice per day with buffer only, or 2 mg/Kg of D-SLAM protein, or truncated forms thereof. Mice receive this treatment for 4 consecutive days, at which time they are sacrificed and various tissues and serum collected for analyses. Comparison of H&E sections from normal and D-SLAM protein-treated spleens identify the results of the activity of D-SLAM protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from D-SLAM protein-treated mice is used to indicate whether D-SLAM protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and D-SLAM protein-treated mice.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 33

D-SLAM Functions As an Inhibitor of B Cell Proliferation in the Presence of BLyS To further examine the inhibitory activity of D-SLAM on B cells, the effect of D-SLAM on BLyS activated B cells was examined.

Human tonsillar B cells were purified by magnetic bead (MACS) depletion of CD3-positive cells. The resulting cell population was routinely greater than 95% B cells as assessed by expression of CD19 and CD20. Various dilutions of human recombinant D-SLAM or D-SLAM.Fc (M1-D233 of SEQ ID NO:2 fused to the Fe portion) were placed into individual wells of a 96-well plate to which was added $10^5$ B cells suspended in culture medium (RPMI 1640 containing 10% FBS, $5\times10^{-5}$ M 2ME, 100 U/ml penicillin, 100 microgram/ml streptomycin, and $10^{-5}$ dilution of Pansorbin (SAC) or $10^{-5}$ dilution of Pansorbin (SAC) and BLyS (100 ng/ml) in a total volume of 150 microliters. SAC and SAC+BLyS stimulated B cells are incubated with or without increasing concentrations of D-SLAM.Fc or OX40.Fc. Proliferation was quantitated by a 20 h pulse (1 microCi/well) of $^3$H-thymidine (6.7 Ci/mM) beginning 72 h post factor addition.

Results:

Addition of D-SLAM.Fc to the cell culture induced a strong dose-dependent inhibition of BLyS induced cell proliferative activity. Treatment with OX40.Fc showed no inhibitory effect.

Example 34

T Cell Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4 C (1 µg/ml in 0.05 M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of D-SLAM protein (total volume 200 µl). Relevant protein buffer and medium alone are controls. After 48 hr. culture at 37 C, plates are spun for 2 min. at 1000 rpm and 100 µl of supernatant is removed and stored –20 C for measurement of IL-2 (or other cytokines) if effect on proliferation is observed. Wells are supplemented with 100 µl of medium containing 0.5 µCi of $^3$H-thymidine and cultured at 37 C for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of D-SLAM proteins.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 35

Effect of D-SLAM on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of D-SLAM or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines.

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of D-SLAM for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules.

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of D-SLAM or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival.

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. D-SLAM, agonists, or antagonists of D-SLAM can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay.

Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 µg/ml, and then incubaed at room temperature for 5 minutes before FACScan analysis. PI uptake has been demonstrated to correlate with DNA fragmentation in this experimental paradigm.

Effect on cytokine release.

An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/ml with increasing concentrations of D-SLAM and under the same conditions, but in the absence of D-SLAM. For IL-12 production, the cells are primed overnight with IFN (100 U/ml) in presence of D-SLAM. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst.

Purified monocytes are plated in 96-w plate at $2-1 \times 10^5$ cell/well. Increasing concentrations of D-SLAM are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Results

As shown below, D-SLAM appears to specifically bind monocyte-derived dendritic cells, while in this experiment, D-SLAM did not bind to monocytes, T cells, or a variety of cell lines.

Mean Fluorescence

|  | Control | D-SLAM |
| --- | --- | --- |
| Dendritic cells | 3.94 | 10.95 |
| Monocytes | 3.18 | 3.18 |
| T cells | 10.84 | 10.85 |
| CD3 activ. T cells | 5.94 | 5.93 |
| IM-9 | 4.1 | 4.51 |
| K562 | 2.65 | 2.89 |
| SupT13 | 2.63 | 3.76 |
| Jurkat | 3.37 | 3.62 |
| THP-1 | 3.92 | 4.71 |

Moreover, following incubation of dendritic cells with D-SLAM, an upregulation of a number of cell surface markers that are indicative of dendritic cell maturation or activation are observed (see below). Thus, D-SLAM may be involved in dendritic cell activation and maturation.

Mean Fluorescence

|  | Controls | HLA-DR | CD54 | CD86 | CD83 |
|---|---|---|---|---|---|
| Untreated | 6/5 | 1597 | 325 | 23 | 4 |
| D-SLAM 10 | 6/4 | 2432 | 488 | 43 | 5 |
| D-SLAM 100 | 5/3 | 3545 | 309 | 154 | 10 |
| D-SLAM 1000 | 8/3 | 2952 | 657 | 258 | 18 |

Additional data suggests that D-SLAM may induce TNF-alpha production by monocytes, and that D-SLAM may bind to itself in a homotypic association. Therefore, D-SLAM would likely activate any cell, including non-hematopoietic cells, such as stromal cells, having D-SLAM expressed on the cell surface.

Thus, activating/maturing dendritic cells by increasing the amount of D-SLAM in a patient could be useful in the treatment, diagnosis, detection, and/or prevention of cancer and modulation the immune response. For example, if increasing the amount of D-SLAM elevates cell surface expression of dendritic cell markers, such as CD83, immune responses against tumors may be activated. In such an instance, treatment of patients having tumors with a soluble version of D-SLAM could lead to upregulation of CD83 on dendritic cells and result in enhanced recognition of tumors leading to an enhanced rejection/killing of the tumor.

Example 36

D-SLAM Biological Effects

Astrocyte and Neuronal Assays

Recombinant D-SLAM, expressed and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate D-SLAM's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." Proc. Natl. Acad. Sci. USA 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of D-SLAM to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or D-SLAM with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or D-SLAM with or without IL-1α for 24 hours. The supernatants are collected and assayed for IL-6 by ELISA kit (Endogen, Cambridge, Mass.).

Human lung fibroblasts are cultured with FGF-2 or D-SLAM for 3 days in basal medium before the addition of Alamar Blue to assess effects on growth of the fibroblasts. FGF-2 should show a stimulation at 10–2500 ng/ml which can be used to compare stimulation with D-SLAM.

Parkinson Models

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl. 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, D-SLAM can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of D-SLAM is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if D-SLAM acts to prolong the survival of dopaminergic neurons, it would suggest that D-SLAM may be involved in Parkinson's Disease.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 37

The Effect of D-SLAM on the Growth of Vascular Endothelial Cells

On day 1, human umbilical vein endothelial cells (HUVEC) are seeded at $2-5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. D-SLAM protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that D-SLAM may proliferate vascular endothelial cells.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 38

Stimulatory Effect of D-SLAM on the Proliferation of Vascular Endothelial Cells

For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF$_{165}$ or D-SLAM in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 39

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6:271(36):21985–21992 (1996).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 40

Stimulation of Endothelial Migration

This example will be used to explore the possibility that D-SLAM may stimulate lymphatic endothelial cell migration.

Endothelial cell migration assays are performed using a 48 well microchemotaxis chamber (Neuroprobe Inc., Cabin John, MD; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 41

Stimulation of Nitric Oxide Production by Endothelial Cells

Nitric oxide released by the vascular endothelium is believed to be a mediator of vascular endothelium relaxation. Thus, D-SLAM activity can be assayed by determining nitric oxide production by endothelial cells in response to D-SLAM.

Nitric oxide is measured in 96-well plates of confluent microvascular endothelial cells after 24 hours starvation and a subsequent 4 hr exposure to various levels of a positive control (such as VEGF-1) and D-SLAM. Nitric oxide in the medium is determined by use of the Griess reagent to measure total nitrite after reduction of nitric oxide-derived nitrate by nitrate reductase. The effect of D-SLAM on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

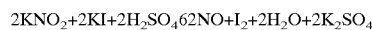

$$2KNO_2 + 2KI + 2H_2SO_4 \to 2NO + I_2 + 2H_2O + 2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217:96–105 (1995).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 42

Effect of D-SLAM on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5 For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or D-SLAM (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 43

Angiogenic Effect on Chick Chorioallantoic Membrane

Chick chorioallantoic membrane (CAM) is a well-established system to examine angiogenesis. Blood vessel formation on CAM is easily visible and quantifiable. The ability of D-SLAM to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 44

Angiogenesis Assay Using a Matrigel Implant in Mouse

In vivo angiogenesis assay of D-SLAM measures the ability of an existing capillary network to form new vessels in an implanted capsule of murine extracellular matrix material (Matrigel). The protein is mixed with the liquid Matrigel at 4 C and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 C the Matrigel material is a liquid. The Matrigel is mixed with D-SLAM at 150 ng/ml at 4 C and drawn into cold 3 ml syringes. Female C57Bl/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 45

Rescue of Ischemia in Rabbit Lower Limb Model

To study the in vivo effects of D-SLAM on ischemia, a rabbit hindlimb ischemia model is created by surgical removal of one femoral arteries as described previously (Takeshita, S. et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked D-SLAM expression plasmid by arterial gene transfer technology using a hydrogel-coated balloon catheter as described (Riessen, R. et al. *Hum Gene Ther.* 4:749–758 (1993); Leclerc, G. et al. *J. Clin. Invest.* 90: 936–944 (1992)). When D-SLAM is used in the treatment, a single bolus of 500 mg D-SLAM protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 46

Effect of D-SLAM on Vasodilation

Since dilation of vascular endothelium is important in reducing blood pressure, the ability of D-SLAM to affect the blood pressure in spontaneously hypertensive rats (SHR) is examined. Increasing doses (0, 10, 30, 100, 300, and 900 mg/kg) of the D-SLAM are administered to 13–14 week old spontaneously hypertensive rats (SHR). Data are expressed as the mean +/−SEM. Statistical analysis are performed with a paired t-test and statistical significance is defined as $p<0.05$ vs. the response to buffer alone.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 47

Rat Ischemic Skin Flap Model

The evaluation parameters include skin blood flow, skin temperature, and factor VIII immunohistochemistry or endothelial alkaline phosphatase reaction. D-SLAM expression, during the skin ischemia, is studied using in situ hybridization.

The study in this model is divided into three parts as follows:

Ischemic skin

Ischemic skin wounds

Normal wounds

The experimental protocol includes:

Raising a 3×4 cm, single pedicle full-thickness random skin flap (myocutaneous flap over the lower back of the animal).

An excisional wounding (4–6 mm in diameter) in the ischemic skin (skin-flap).

Topical treatment with D-SLAM of the excisional wounds (day 0, 1, 2, 3, 4 post-wounding) at the following various dosage ranges: 1 mg to 100 mg.

Harvesting the wound tissues at day 3, 5, 7, 10, 14 and 21 post-wounding for histological, immunohistochemical, and in situ studies.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 48

Peripheral Arterial Disease Model

Angiogenic therapy using D-SLAM is a novel therapeutic strategy to obtain restoration of blood flow around the ischemia in case of peripheral arterial diseases. The experimental protocol includes:

One side of the femoral artery is ligated to create ischemic muscle of the hindlimb, the other side of hindlimb serves as a control.

D-SLAM protein, in a dosage range of 20 mg–500 mg, is delivered intravenously and/or intramuscularly 3 times (perhaps more) per week for 2–3 weeks.

The ischemic muscle tissue is collected after ligation of the femoral artery at 1, 2, and 3 weeks for the analysis of D-SLAM expression and histology. Biopsy is also performed on the other side of normal muscle of the contralateral hindlimb.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 49

Ischemic Myocardial Disease Model

D-SLAM is evaluated as a potent mitogen capable of stimulating the development of collateral vessels, and restructuring new vessels after coronary artery occlusion. Alteration of D-SLAM expression is investigated in situ. The experimental protocol includes:

The heart is exposed through a left-side thoracotomy in the rat. Immediately, the left coronary artery is occluded with a thin suture (6-0) and the thorax is closed.

D-SLAM protein, in a dosage range of 20 mg–500 mg, is delivered intravenously and/or intramuscularly 3 times (perhaps more) per week for 2–4 weeks.

Thirty days after the surgery, the heart is removed and cross-sectioned for morphometric and in situ analyzes.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 50

Rat Corneal Wound Healing Model

This animal model shows the effect of D-SLAM on neovascularization. The experimental protocol includes:

Making a 1–1.5 mm long incision from the center of cornea into the stromal layer.

Inserting a spatula below the lip of the incision facing the outer corner of the eye.

Making a pocket (its base is 1–1.5 mm form the edge of the eye).

Positioning a pellet, containing 50 ng–5 ug of D-SLAM, within the pocket.

D-SLAM treatment can also be applied topically to the corneal wounds in a dosage range of 20 mg–500mg (daily treatment for five days).

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 51

Diabetic Mouse and Glucocorticoid-Impaired Wound Healing Models Diabetic db+/db+ Mouse Model To demonstrate that D-SLAM accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (Suppl):1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhaigh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods. (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

D-SLAM is administered using at a range different doses of D-SLAM, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) D-SLAM.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with D-SLAM. This assessment included verification of the presence of cell accumulation, inflammatory cells, capillaries, fibroblasts, re-epithelialization and epidermal maturity (Greenhalgh, D. G. et al., *Am. J. Patho.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that D-SLAM can accelerate the healing process, the effects of multiple topical applications of D-SLAM on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

D-SLAM is administered using at a range different doses of D-SLAM, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) D-SLAM treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm², the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with D-SLAM. A calibrated lens micrometer is used by a blinded observer to determine the distance of the wound gap.

Experimental data are analyzed using an unpaired t test. A p value of <0.05 is considered significant.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 52

Lymphadema Animal Model

The purpose of this experimental approach is to create an appropriate and consistent lymphedema model for testing the therapeutic effects of D-SLAM in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements:

Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements:

On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements:

Blood is drawn, spun, and serum separated prior to surgery and then at conclusion for total protein and Ca2+ comparison.

Limb Weight Comparison:

After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations:

The transverse muscle located behind the knee (popliteal) area is dissected and arranged in a metal mold, filled with freezeGel, dipped into cold methylbutane, placed into labeled sample bags at −80EC until sectioning. Upon sectioning, the muscle is observed under fluorescent microscopy for lymphatics.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 53

Suppression of TNF Alpha-induced Adhesion Molecule Expression by D-SLAM

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of D-SLAM to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 C humidified incubator containing 5% $CO_2$. HUVECs are seeded in 96-well plates at concentrations of $1\times10^4$ cells/well in EGM medium at 37 C for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 C Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 C for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 µl of diluted ExtrAvidin-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity in D-SLAM protein. However, one skilled in the art could easily modify the exemplified studies to test the activity of D-SLAM polynucleotides (e.g., gene therapy), agonists, and/or antagonists of D-SLAM.

Example 54

Effect of D-SLAM and Its Antagonists and Agonists in Treating Graft-versus-host Disease Associated Lymphoid Atrophy and Hypoplasia in Mice An analysis of the use of antagonists of D-SLAM (e.g., anti-D-SLAM antibody) to treat, prevent, detect, and/or diagnose graft-versus-host disease (GVHD)-associated lymphoid hypoplasia/atrophy is performed through the use of a C57BL/6 parent into (BALB/c×C57BL/6) F1 (CBF1) mouse model. This parent into F1 mouse model is a well-characterized and reproducible animal model of GVHD in bone marrow transplant patients, which is well know to one of ordinary skill in the art (see, Gleichemann, et al., *Immunol. Today* 5:324, 1984). A soluble D-SLAM antagonist is expected to induce the proliferation and differentiation of B lymphocytes, and correct the lymphoid hypoplasia and atrophy observed in this animal model of GVHD (Piguet, et al., *J. Exp. Med.* 166:1280 (1987); Hattori, et al., Blood 90:542 (1997)).

Initiation of the GVHD condition is induced by the intravenous injection of approximately $1-5\times10^8$ spleen cells from C57BL/6 mice into (BALB/c×C57BL/6) F1 mice (both are available from Jackson Lab, Bar Harbor, Me.). Groups of 6 to 8 mice receive daily either 0.1 to 5.0 mg/kg of D-SLAM antagonist or buffer control intraperitoneally, intramascullarly or intradermally starting from the days when lymphoid hypoplasia and atrophy are mild (~day 5), moderate (~day 12) or severe (~day 20) following the parental cell injection. The effect of D-SLAM antagonist on lymphoid hypoplasia and atrophy of spleen is analyzed by FACS and histopathology at multiple time points (3–4) between day 10–30. Briefly, splenocytes are prepared from normal CBF1, GVHD or D-SLAM antagonist-treated mice, and stained with fluorescein phycoerythrin-conjugated anti-H-2Kb, biotin-conjugated anti-H-2Kd, and FITC-conjugated anti-CD4, anti-CD8, or anti-B220, followed by a CyChrome-conjugated avidin. All of these conjugated antibodies can be purchased from PharMingen (San Diego, Calif.). Cells are then analysis on a FACScan (Becton Dickinson, San Jose, Calif.). Recipient and donor lymphocytes are identified as H-2Kb+Kd+ and H-2Kb+Kd-cells, respectively. Cell numbers of CD4+T, CD8+T and B220+B cells of recipient or donor origin are calculated from the total numbers of splenocytes recovered and the percentages of each subpopulation are determined by the three color analysis. Histological evaluation of the relative degree of tissue damage in other GVHD-associated organs (liver, skin and intestine) may be conducted after sacrificing the animals.

Finally, D-SLAM antagonist and buffer-treated animals undergo a clinical evaluation every other day to assess cachexia, body weight and lethality.

D-SLAM polypeptides and/or D-SLAM agonists of the invention may also be examined in this acute GVHD murine model.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Moreover, the sequence listing is herein incorporated by reference.

Further, the Sequence Listing submitted herewith, and the Sequence Listings submitted in U.S. Application Serial No. 60/267,523, filed Feb. 6, 2001, 60/190,062 filed Mar. 17, 2000, Ser. No. 09/369,248, filed Aug. 5, 1999, Ser. No. 09/244,110, filed Feb. 4, 1999, 60/073,962, filed Feb. 6, 1998, 60/078,572, filed Mar. 19, 1998, PCT/US00/21130, filed Aug. 3, 2000, and PCT/US99/02415, filed Feb. 4, 1999, in both computer and paper forms in each case, are hereby incorporated by reference in their entireties.

SEQUENCE LISTING

```
<160> NUMBER OF SEQ ID NOS: 30

<210> SEQ ID NO 1
<211> LENGTH: 3220
<212> TYPE: DNA
<213> ORGANISM: Homo sapiens
<220> FEATURE:
<221> NAME/KEY: CDS
<222> LOCATION: (92)..(949)

<400> SEQUENCE: 1
gaaggaccac agctcctccc gtgcatccac tcggcctggg aggttctgga ttttggctgt      60
cgagggagtt tgcctgcctc tccagagaaa g atg gtc atg agg ccc ctg tgg       112
                                  Met Val Met Arg Pro Leu Trp
                                    1               5 agt ctg ctt ctc tgg gaa gcc cta ctt ccc att aca gtt act ggt gcc      160
Ser Leu Leu Leu Trp Glu Ala Leu Leu Pro Ile Thr Val Thr Gly Ala
         10                  15                  20 caa gtg ctg agc aaa gtc ggg ggc tcg gtg ctg ctg gtg gca gcg cgt      208
Gln Val Leu Ser Lys Val Gly Gly Ser Val Leu Leu Val Ala Ala Arg
 25                  30                  35 ccc cct ggc ttc caa gtc cgt gag gct atc tgg cga tct ctc tgg cct      256
Pro Pro Gly Phe Gln Val Arg Glu Ala Ile Trp Arg Ser Leu Trp Pro
 40                  45                  50                  55 tca gaa gag ctc ctg gcc acg ttt ttc cga ggc tcc ctg gag act ctg      304
Ser Glu Glu Leu Leu Ala Thr Phe Phe Arg Gly Ser Leu Glu Thr Leu
                 60                  65                  70 tac cat tcc cgc ttc ctg ggc cga gcc cag cta cac agc aac ctc agc      352
Tyr His Ser Arg Phe Leu Gly Arg Ala Gln Leu His Ser Asn Leu Ser
             75                  80                  85 ctg gag ctc ggg ccg ctg gag tct gga gac agc ggc aac ttc tcc gtg      400
Leu Glu Leu Gly Pro Leu Glu Ser Gly Asp Ser Gly Asn Phe Ser Val
         90                  95                 100 ttg atg gtg gac aca agg ggc cag ccc tgg acc cag acc ctc cag ctc      448
Leu Met Val Asp Thr Arg Gly Gln Pro Trp Thr Gln Thr Leu Gln Leu
105                 110                 115 aag gtg tac gat gca gtg ccc agg ccc gtg gta caa gtg ttc att gct      496
Lys Val Tyr Asp Ala Val Pro Arg Pro Val Val Gln Val Phe Ile Ala
120                 125                 130                 135 gta gaa agg gat gct cag ccc tcc aag acc tgc cag gtt ttc ttg tcc      544
Val Glu Arg Asp Ala Gln Pro Ser Lys Thr Cys Gln Val Phe Leu Ser
                140                 145                 150 tgt tgg gcc ccc aac atc agc gaa ata acc tat agc tgg cga cgg gag      592
Cys Trp Ala Pro Asn Ile Ser Glu Ile Thr Tyr Ser Trp Arg Arg Glu
            155                 160                 165
```

-continued

| | | |
|---|---|---|
| aca acc atg gac ttt ggt atg gaa cca cac agc ctc ttc aca gac gga<br>Thr Thr Met Asp Phe Gly Met Glu Pro His Ser Leu Phe Thr Asp Gly<br>170 175 180 | | 640 |
| cag gtg ctg agc att tcc ctg gga cca gga gac aga gat gtg gcc tat<br>Gln Val Leu Ser Ile Ser Leu Gly Pro Gly Asp Arg Asp Val Ala Tyr<br>185 190 195 | | 688 |
| tcc tgc att gtc tcc aac cct gtc agc tgg gac ttg gcc aca gtc acg<br>Ser Cys Ile Val Ser Asn Pro Val Ser Trp Asp Leu Ala Thr Val Thr<br>200 205 210 215 | | 736 |
| ccc tgg gat agc tgt cat cat gag gca gca cca ggg aag gcc tcc tac<br>Pro Trp Asp Ser Cys His His Glu Ala Ala Pro Gly Lys Ala Ser Tyr<br>220 225 230 | | 784 |
| aaa gat gtg ctg ctg gtg gtg gtg cct gtc tcg ctg ctc ctg atg ctg<br>Lys Asp Val Leu Leu Val Val Val Pro Val Ser Leu Leu Leu Met Leu<br>235 240 245 | | 832 |
| gtt act ctc ttc tct gcc tgg cac tgg tgc ccc tgc tca ggg aaa aag<br>Val Thr Leu Phe Ser Ala Trp His Trp Cys Pro Cys Ser Gly Lys Lys<br>250 255 260 | | 880 |
| aaa aag gat gtc cat gct gac aga gtg ggt cca gag aca gag aac ccc<br>Lys Lys Asp Val His Ala Asp Arg Val Gly Pro Glu Thr Glu Asn Pro<br>265 270 275 | | 928 |
| ctt gtg cag gat ctg cca taa aggacaatat gaactgatgc ctggactatc<br>Leu Val Gln Asp Leu Pro<br>280 285 | | 979 |
| agtaacccca ctgcacaggc acacgatgct ctgggacata actggtgcct ggaaatcacc | | 1039 |
| atggtcctca tatctcccat gggaatcctg tcctgcctcg aaggagcagc ctgggcagcc | | 1099 |
| atcacaccac gaggacagga agcaccagca cgtttcacac ctcccccttc cctctcccat | | 1159 |
| cttctcatat cctggctctt ctctgggcaa gatgagccaa gcagaacatt ccatccagga | | 1219 |
| cactggaagt tctccaggat ccagatccat ggggacatta atagtccaag gcattccctc | | 1279 |
| ccccaccact attcataaag tattaaccaa ctggcaccaa ggaattgcct ccagcctgag | | 1339 |
| tcctaggctc taaaagatat tacatatttg aactaataga ggaactctga gtcacccatg | | 1399 |
| ccagcatcag cttcagcccc agaccctgca gtttgagatc tgatgcttcc tgagggccaa | | 1459 |
| ggcattgctg taagaaaagg tctagaaata ggtgaaagtg agaggtgggg acagggggtt | | 1519 |
| tctctttctg gcctaaggac tttcaggtaa tcagagttca tgggccctca aggtaaatt | | 1579 |
| gcagttgtag acaccgagga tggttgacaa cccatggttg agatgggcac cgttttgcag | | 1639 |
| gaaacaccat attaatagac atcctcacca tctccatccg ctctcacgcc tcctgcagga | | 1699 |
| tctgggagtg agggtggaga gtctttcctc acgctccagc acagtggcca ggaaaagaaa | | 1759 |
| tactgaattt gccccagcca acaggacgtt cttgcacaac ttcaagaaaa gcagctcagc | | 1819 |
| tcaggatgag tcttcctgcc tgaaactgag agagtgaaga accataaaac gctatgcaga | | 1879 |
| aggaacatta tggagagaaa gggtactgag gcactctaga atctgccaca ttcattttca | | 1939 |
| aatgcaaatg cagaagactt accttagttc aggggaggg dacaaagacc ccacagccca | | 1999 |
| acagcaggac tgtagaggtc actctgactc catcaaactt tttattgtgg ccatcttagg | | 2059 |
| aaaatacatt ctgcccctga atgattctgt ctagaaaagc tctggagtat tgatcactac | | 2119 |
| tggaaaaaca cttaaggagc taaacttacc ttcggggatt attagctgat aaggttcaca | | 2179 |
| gtttctctca cccaggtgta actggatttt ttctggggcc tcaatccagt cttgataaca | | 2239 |
| gcgaggaaag aggtattgaa gaaacagggg tgggtttgaa gtactattt ccccagggtg | | 2299 |
| gcttcaatct ccccacctag gatgtcagcc ctgtccaagg accttccctc ttctccccca | | 2359 |
| gttccctggg caatcacttc accttggaca aaggatcagc acagctggcc tccagatcca | | 2419 |

-continued

```
catcaccact cttccactcg attgttccca gatcctccct gcctggcctg ctcagaggtt      2479
ccctgttggt aacctggctt tatcaaattc tcatcccttt cccacaccca cttctctcct      2539
atcaccttcc cccaagatta cctgaacagg gtccatggcc actcaacctg tcagcttgca      2599
ccatccccac ctgccaccta cagtcaggcc acatgcctgg tcactgaatc atgcaaaact      2659
ggcctcagtc cctaaaaatg atgtggaaag gaaagcccag gatctgacaa tgagccctgg      2719
tggatttgtg gggaaaaaat acacagcact ccccaccttt ctttcgttca tctccagggc      2779
cccacctcag atcaaagcag ctctggatga gatgggacct gcagctctcc ctccacaagg      2839
tgactcttag caacctcatt tcgacagtgg tttgtagcgt ggtgcaccag ggccttgttg      2899
aacagatcca cactgctcta ataaagttcc catccttaat gactcacttg tcaactagtg      2959
gactaattaa ccctccacca aaaaacaca aagtgcttct gtgagaccaa ttttgtgcta      3019
atgagcattg agactgatgc tttgtaagtc acaccacaac aaatattgat tgagggcgct      3079
gcatgtgctg ggtacatttc ttggcacttg ggaatcagta gtcaagcgaa acccttgcct      3139
ttgagagttt atggtctgga taatataaat aaacaagtaa gcataaaaaa aaaaaaaaa      3199 aaaaaaaaaa aaaaaaaaaa a                                                3220
```

<210> SEQ ID NO 2
<211> LENGTH: 285
<212> TYPE: PRT
<213> ORGANISM: Homo sapiens

<400> SEQUENCE: 2

```
Met Val Met Arg Pro Leu Trp Ser Leu Leu Trp Glu Ala Leu Leu
 1               5                  10                  15

Pro Ile Thr Val Thr Gly Ala Gln Val Leu Ser Lys Val Gly Gly Ser
                20                  25                  30

Val Leu Leu Val Ala Ala Arg Pro Gly Phe Gln Val Arg Glu Ala
            35                  40                  45

Ile Trp Arg Ser Leu Trp Pro Ser Glu Glu Leu Leu Ala Thr Phe Phe
     50                  55                  60

Arg Gly Ser Leu Glu Thr Leu Tyr His Ser Arg Phe Leu Gly Arg Ala
 65                  70                  75                  80

Gln Leu His Ser Asn Leu Ser Leu Glu Leu Gly Pro Leu Glu Ser Gly
                85                  90                  95

Asp Ser Gly Asn Phe Ser Val Leu Met Val Asp Thr Arg Gly Gln Pro
            100                 105                 110

Trp Thr Gln Thr Leu Gln Leu Lys Val Tyr Asp Ala Val Pro Arg Pro
        115                 120                 125

Val Val Gln Val Phe Ile Ala Val Glu Arg Asp Ala Gln Pro Ser Lys
    130                 135                 140

Thr Cys Gln Val Phe Leu Ser Cys Trp Ala Pro Asn Ile Ser Glu Ile
145                 150                 155                 160

Thr Tyr Ser Trp Arg Arg Glu Thr Thr Met Asp Phe Gly Met Glu Pro
                165                 170                 175

His Ser Leu Phe Thr Asp Gly Gln Val Leu Ser Ile Ser Leu Gly Pro
            180                 185                 190

Gly Asp Arg Asp Val Ala Tyr Ser Cys Ile Val Ser Asn Pro Val Ser
        195                 200                 205

Trp Asp Leu Ala Thr Val Thr Pro Trp Asp Ser Cys His His Glu Ala
    210                 215                 220
```

```
Ala Pro Gly Lys Ala Ser Tyr Lys Asp Val Leu Leu Val Val Pro
225                 230                 235                 240

Val Ser Leu Leu Leu Met Leu Val Thr Leu Phe Ser Ala Trp His Trp
            245                 250                 255

Cys Pro Cys Ser Gly Lys Lys Lys Asp Val His Ala Asp Arg Val
        260                 265                 270

Gly Pro Glu Thr Glu Asn Pro Leu Val Gln Asp Leu Pro
        275                 280                 285

<210> SEQ ID NO 3
<211> LENGTH: 335
<212> TYPE: PRT
<213> ORGANISM: Homo sapiens

<400> SEQUENCE: 3

Met Asp Pro Lys Gly Leu Leu Ser Leu Thr Phe Val Leu Phe Leu Ser
1               5                   10                  15

Leu Ala Phe Gly Ala Ser Tyr Gly Thr Gly Arg Met Met Asn Cys
            20                  25                  30

Pro Lys Ile Leu Arg Gln Leu Gly Ser Lys Val Leu Leu Pro Leu Thr
        35                  40                  45

Tyr Glu Arg Ile Asn Lys Ser Met Asn Lys Ser Ile His Ile Val Val
    50                  55                  60

Thr Met Ala Lys Ser Leu Glu Asn Ser Val Glu Asn Lys Ile Val Ser
65                  70                  75                  80

Leu Asp Pro Ser Glu Ala Gly Pro Pro Arg Tyr Leu Gly Asp Arg Tyr
                85                  90                  95

Lys Phe Tyr Leu Glu Asn Leu Thr Leu Gly Ile Arg Glu Ser Arg Lys
            100                 105                 110

Glu Asp Glu Gly Trp Tyr Leu Met Thr Leu Glu Lys Asn Val Ser Val
        115                 120                 125

Gln Arg Phe Cys Leu Gln Leu Arg Leu Tyr Glu Gln Val Ser Thr Pro
130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                165                 170                 175

Ser Glu Lys Ala Gly Thr His Pro Leu Asn Pro Ala Asn Ser Ser His
            180                 185                 190

Leu Leu Ser Leu Thr Leu Gly Pro Gln His Ala Asp Asn Ile Tyr Ile
        195                 200                 205

Cys Thr Val Ser Asn Pro Ile Ser Asn Asn Ser Gln Thr Phe Ser Pro
210                 215                 220

Trp Pro Gly Cys Arg Thr Asp Pro Ser Glu Thr Lys Pro Trp Ala Val
225                 230                 235                 240

Tyr Ala Gly Leu Leu Gly Gly Val Ile Met Ile Leu Ile Met Val Val
                245                 250                 255

Ile Leu Gln Leu Arg Arg Arg Gly Lys Thr Asn His Tyr Gln Thr Thr
            260                 265                 270

Val Glu Lys Lys Ser Leu Thr Ile Tyr Ala Gln Val Gln Lys Pro Gly
        275                 280                 285

Pro Leu Gln Lys Lys Leu Asp Ser Phe Pro Ala Gln Asp Pro Cys Thr
290                 295                 300

Thr Ile Tyr Val Ala Ala Thr Glu Pro Val Pro Glu Ser Val Gln Glu
305                 310                 315                 320
```

```
Thr Asn Ser Ile Thr Val Tyr Ala Ser Val Thr Leu Pro Glu Ser
            325                 330                 335
```

<210> SEQ ID NO 4
<211> LENGTH: 733
<212> TYPE: DNA
<213> ORGANISM: Homo sapiens

<400> SEQUENCE: 4

| | | | | | |
|---|---|---|---|---|---|
| gggatccgga | gcccaaatct | tctgacaaaa | ctcacacatg | cccaccgtgc | ccagcacctg | 60 |
| aattcgaggg | tgcaccgtca | gtcttcctct | tcccccaaa | acccaaggac | accctcatga | 120 |
| tctcccggac | tcctgaggtc | acatgcgtgg | tggtggacgt | aagccacgaa | gaccctgagg | 180 |
| tcaagttcaa | ctggtacgtg | gacggcgtgg | aggtgcataa | tgccaagaca | aagccgcggg | 240 |
| aggagcagta | caacagcacg | taccgtgtgg | tcagcgtcct | caccgtcctg | caccaggact | 300 |
| ggctgaatgg | caaggagtac | aagtgcaagg | tctccaacaa | agccctccca | acccccatcg | 360 |
| agaaaaccat | ctccaaagcc | aaagggcagc | cccgagaacc | acaggtgtac | accctgcccc | 420 |
| catcccggga | tgagctgacc | aagaaccagg | tcagcctgac | ctgcctggtc | aaaggcttct | 480 |
| atccaagcga | catcgccgtg | gagtgggaga | gcaatgggca | gccggagaac | aactacaaga | 540 |
| ccacgcctcc | cgtgctggac | tccgacggct | ccttcttcct | ctacagcaag | ctcaccgtgg | 600 |
| acaagagcag | gtggcagcag | gggaacgtct | tctcatgctc | cgtgatgcat | gaggctctgc | 660 |
| acaaccacta | cacgcagaag | agcctctccc | tgtctccggg | taaatgagtg | cgacggccgc | 720 |
| gactctagag | gat | | | | | 733 |

<210> SEQ ID NO 5
<211> LENGTH: 5
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any amino acid

<400> SEQUENCE: 5

```
Trp Ser Xaa Trp Ser
 1           5
```

<210> SEQ ID NO 6
<211> LENGTH: 86
<212> TYPE: DNA
<213> ORGANISM: Artificial Sequence
<220> FEATURE:
<221> NAME/KEY: Primer_Bind
<223> OTHER INFORMATION: Synthetic sequence with 4 tandem copies of the
   GAS binding site found in the IRF1 promoter (Rothman et al.,
   Immunity 1:457-468 (1994)), 18 nucleotides complementary to the
   SV40 early promoter, and a Xho I restriction site.

<400> SEQUENCE: 6

| | | | | | |
|---|---|---|---|---|---|
| gcgcctcgag | atttccccga | aatctagatt | tccccgaaat | gatttccccg | aaatgatttc | 60 |
| cccgaaatat | ctgccatctc | aattag | | | | 86 |

<210> SEQ ID NO 7
<211> LENGTH: 27
<212> TYPE: DNA
<213> ORGANISM: Artificial Sequence
<220> FEATURE:
<221> NAME/KEY: Primer_Bind
<223> OTHER INFORMATION: Synthetic sequence complementary to the SV40 promter; includes a Hind III restriction site.

<400> SEQUENCE: 7
gcggcaagct ttttgcaaag cctaggc                                          27

<210> SEQ ID NO 8
<211> LENGTH: 271
<212> TYPE: DNA
<213> ORGANISM: Artificial Sequence
<220> FEATURE:
<221> NAME/KEY: Protein_Bind
<223> OTHER INFORMATION: Synthetic promoter for use in biological
      assays; includes GAS binding sites found in the IRF1 promoter
      (Rothman et al., Immunity 1:457-468 (1994)).

<400> SEQUENCE: 8
ctcgagattt ccccgaaatc tagatttccc cgaaatgatt tccccgaaat gatttccccg      60
aaatatctgc catctcaatt agtcagcaac catagtcccg ccctaactc cgcccatccc     120 gcccctaact ccgcccagtt ccgcccattc tccgccccat ggctgactaa tttttttat    180 ttatgcagag gccgaggccg cctcggcctc tgagctattc cagaagtagt gaggaggctt    240
ttttggaggc ctaggctttt gcaaaaagct t                                   271

<210> SEQ ID NO 9
<211> LENGTH: 32
<212> TYPE: DNA
<213> ORGANISM: Artificial Sequence
<220> FEATURE:
<221> NAME/KEY: Primer_Bind
<223> OTHER INFORMATION: Synthetic primer complementary to human genomic
      EGR-1 promoter sequence (Sakamoto et al., Oncogene 6:867-871
      (1991)); including an Xho I restriction site.

<400> SEQUENCE: 9
gcgctcgagg gatgacagcg atagaacccc gg                                   32

<210> SEQ ID NO 10
<211> LENGTH: 31
<212> TYPE: DNA
<213> ORGANISM: Artificial Sequence
<220> FEATURE:
<221> NAME/KEY: Primer_Bind
<223> OTHER INFORMATION: Synthetic primer complementary to human genomic
      EGR-1 promoter sequence (Sakamoto et al., Oncogene 6:867-871
      (1991)); including an Hind III restriction site.

<400> SEQUENCE: 10
gcgaagcttc gcgactcccc ggatccgcct c                                    31

<210> SEQ ID NO 11
<211> LENGTH: 12
<212> TYPE: DNA
<213> ORGANISM: Homo sapiens

<400> SEQUENCE: 11
ggggactttc cc                                                         12

<210> SEQ ID NO 12
<211> LENGTH: 73
<212> TYPE: DNA
<213> ORGANISM: Artificial Sequence
<220> FEATURE:
<221> NAME/KEY: Primer_Bind
<223> OTHER INFORMATION: Synthetic primer with 4 tandem copies of the
      NF-KB binding site (GGGGACTTTCCC), 18 nucleotides complementary
      to the 5' end of the SV40 early promoter sequence, and a XhoI

```
                                                restriction site.

<400> SEQUENCE: 12
gcggcctcga ggggactttc ccggggactt tccggggact ttccgggact ttccatcctg    60
ccatctcaat tag                                                      73

<210> SEQ ID NO 13
<211> LENGTH: 256
<212> TYPE: DNA
<213> ORGANISM: Artificial Sequence
<220> FEATURE:
<221> NAME/KEY: Protein_Bind
<223> OTHER INFORMATION: Synthetic promoter for use in biological
      assays; including NF-KB binding sites.

<400> SEQUENCE: 13
ctcgagggga ctttcccggg gactttccgg ggactttccg ggactttcca tctgccatct    60
caattagtca gcaaccatag tcccgcccct aactccgccc atcccgcccc taactccgcc   120
cagttccgcc cattctccgc cccatggctg actaattttt tttatttatg cagaggccga   180
ggccgcctcg gcctctgagc tattccagaa gtagtgagga ggcttttttg gaggcctagg   240
cttttgcaaa aagctt                                                  256

<210> SEQ ID NO 14
<211> LENGTH: 44
<212> TYPE: DNA
<213> ORGANISM: Artificial Sequence
<220> FEATURE:
<221> NAME/KEY: Primer_Bind
<223> OTHER INFORMATION: Synthetic primer complementary to extracellular
      domain of D-SLAM starting at Q24; includes a Sph restriction site.

<400> SEQUENCE: 14
gcagcagcat gcaagtgctg agcaaagtcg ggggctcggt gctg                     44

<210> SEQ ID NO 15
<211> LENGTH: 45
<212> TYPE: DNA
<213> ORGANISM: Artificial Sequence
<220> FEATURE:
<221> NAME/KEY: Primer_Bind
<223> OTHER INFORMATION: Synthetic primer complementary to extracellular
      domain of D-SLAM ending at D233; includes a BglII restriction site

<400> SEQUENCE: 15
gcagcaagat ctatctttgt aggaggcctt ccctggtgct gcctc                    45

<210> SEQ ID NO 16
<211> LENGTH: 427
<212> TYPE: PRT
<213> ORGANISM: Artificial Sequence
<220> FEATURE:
<221> NAME/KEY: DOMAIN
<222> LOCATION: (1-211)
<223> OTHER INFORMATION: Recombinant extracellular domain of D-SLAM from
      Q24-D233
<221> NAME/KEY: DOMAIN
<222> LOCATION: (212-427)
<223> OTHER INFORMATION: C-terminal Histidine tag

<400> SEQUENCE: 16

Met Gln Val Leu Ser Lys Val Gly Gly Ser Val Leu Leu Val Ala Ala
 1               5                  10                  15

Arg Pro Pro Gly Phe Gln Val Arg Glu Ala Ile Trp Arg Ser Leu Trp
             20                  25                  30
```

```
Pro Ser Glu Glu Leu Leu Ala Thr Phe Phe Arg Gly Ser Leu Glu Thr
         35                  40                  45

Leu Tyr His Ser Arg Phe Leu Gly Arg Ala Gln Leu His Ser Asn Leu
     50                  55                  60

Ser Leu Glu Leu Gly Pro Leu Glu Ser Gly Asp Ser Gly Asn Phe Ser
 65                  70                  75                  80

Val Leu Met Val Asp Thr Arg Gly Gln Pro Trp Thr Gln Thr Leu Gln
                 85                  90                  95

Leu Lys Val Tyr Asp Ala Val Pro Arg Pro Val Gln Val Phe Ile
             100                 105                 110

Ala Val Glu Arg Asp Ala Gln Pro Ser Lys Thr Cys Gln Val Phe Leu
         115                 120                 125

Ser Cys Trp Ala Pro Asn Ile Ser Glu Ile Thr Tyr Ser Trp Arg Arg
 130                 135                 140

Glu Thr Thr Met Asp Phe Gly Met Glu Pro His Ser Leu Phe Thr Asp
145                 150                 155                 160

Gly Gln Val Leu Ser Ile Ser Leu Gly Pro Gly Asp Arg Asp Val Ala
                 165                 170                 175

Tyr Ser Cys Ile Val Ser Asn Pro Val Ser Trp Asp Leu Ala Thr Val
             180                 185                 190

Thr Pro Trp Asp Ser Cys His His Glu Ala Ala Pro Gly Lys Ala Ser
         195                 200                 205

Tyr Lys Asp Gln Val Leu Ser Lys Val Gly Ser Val Leu Leu Val
     210                 215                 220

Ala Ala Arg Pro Pro Gly Phe Gln Val Arg Glu Ala Ile Trp Arg Ser
225                 230                 235                 240

Leu Trp Pro Ser Glu Glu Leu Leu Ala Thr Phe Phe Arg Gly Ser Leu
                 245                 250                 255

Glu Thr Leu Tyr His Ser Arg Phe Leu Gly Arg Ala Gln Leu His Ser
             260                 265                 270

Asn Leu Ser Leu Glu Leu Gly Pro Leu Glu Ser Gly Asp Ser Gly Asn
         275                 280                 285

Phe Ser Val Leu Met Val Asp Thr Arg Gly Gln Pro Trp Thr Gln Thr
290                 295                 300

Leu Gln Leu Lys Val Tyr Asp Ala Val Pro Arg Pro Val Gln Val
305                 310                 315                 320

Phe Ile Ala Val Glu Arg Asp Ala Gln Pro Ser Lys Thr Cys Gln Val
                 325                 330                 335

Phe Leu Ser Cys Trp Ala Pro Asn Ile Ser Glu Ile Thr Tyr Ser Trp
             340                 345                 350

Arg Arg Glu Thr Thr Met Asp Phe Gly Met Glu Pro His Ser Leu Phe
         355                 360                 365

Thr Asp Gly Gln Val Leu Ser Ile Ser Leu Gly Pro Gly Asp Arg Asp
     370                 375                 380

Val Ala Tyr Ser Cys Ile Val Ser Asn Pro Val Ser Trp Asp Leu Ala
385                 390                 395                 400

Thr Val Thr Pro Trp Asp Ser Cys His His Glu Ala Ala Pro Gly Lys
                 405                 410                 415

Ala Ser Tyr Lys Asp His His His His His
             420                 425

<210> SEQ ID NO 17
<211> LENGTH: 45
```

-continued

```
<212> TYPE: DNA
<213> ORGANISM: Artificial sequence
<220> FEATURE:
<221> NAME/KEY: Primer_Bind
<223> OTHER INFORMATION: Synthetic primer complementary to
      extracellular domain of D-SLAM starting at A23; includes a
      BamHI restriction site

<400> SEQUENCE: 17
gcagcaggat ccgcccaagt gctgagcaaa gtcgggggct cggtg            45

<210> SEQ ID NO 18
<211> LENGTH: 48
<212> TYPE: DNA
<213> ORGANISM: Artificial sequence
<220> FEATURE:
<221> NAME/KEY: Primer_Bind
<223> OTHER INFORMATION: Synthetic primer complementary to the
      extracellular domain of D-SLAM ending at D233; includes a HindIII
      restriction site

<400> SEQUENCE: 18
gcagcaaagc ttttaatctt tgtaggaggc cttccctggt gctgcctc           48

<210> SEQ ID NO 19
<211> LENGTH: 223
<212> TYPE: PRT
<213> ORGANISM: Artificial Sequence
<220> FEATURE:
<221> NAME/KEY: Domain
<222> LOCATION: (1-12)
<223> OTHER INFORMATION: N-terminal Histidine tag
<221> NAME/KEY: Domain
<222> LOCATION: (13-223)
<223> OTHER INFORMATION: Recombinant extracellular domain of D-SLAM
      A23-D233.

<400> SEQUENCE: 19

Met Arg Gly Ser His His His His His His Gly Ser Ala Gln Val Leu
 1               5                  10                  15

Ser Lys Val Gly Gly Ser Val Leu Leu Val Ala Ala Arg Pro Pro Gly
            20                  25                  30

Phe Gln Val Arg Glu Ala Ile Trp Arg Ser Leu Trp Pro Ser Glu Glu
        35                  40                  45

Leu Leu Ala Thr Phe Phe Arg Gly Ser Leu Glu Thr Leu Tyr His Ser
    50                  55                  60

Arg Phe Leu Gly Arg Ala Gln Leu His Ser Asn Leu Ser Leu Glu Leu
65                  70                  75                  80

Gly Pro Leu Glu Ser Gly Asp Ser Gly Asn Phe Ser Val Leu Met Val
                85                  90                  95

Asp Thr Arg Gly Gln Pro Trp Thr Gln Thr Leu Gln Leu Lys Val Tyr
            100                 105                 110

Asp Ala Val Pro Arg Pro Val Val Gln Val Phe Ile Ala Val Glu Arg
        115                 120                 125

Asp Ala Gln Pro Ser Lys Thr Cys Gln Val Phe Leu Ser Cys Trp Ala
    130                 135                 140

Pro Asn Ile Ser Glu Ile Thr Tyr Ser Trp Arg Arg Glu Thr Thr Met
145                 150                 155                 160

Asp Phe Gly Met Glu Pro His Ser Leu Phe Thr Asp Gly Gln Val Leu
                165                 170                 175

Ser Ile Ser Leu Gly Pro Gly Asp Arg Asp Val Ala Tyr Ser Cys Ile
            180                 185                 190
```

```
Val Ser Asn Pro Val Ser Trp Asp Leu Ala Thr Val Thr Pro Trp Asp
        195                 200                 205

Ser Cys His His Glu Ala Ala Pro Gly Lys Ala Ser Tyr Lys Asp
        210                 215                 220

<210> SEQ ID NO 20
<211> LENGTH: 34
<212> TYPE: DNA
<213> ORGANISM: Artificial sequence
<220> FEATURE:
<221> NAME/KEY: Primer_Bind
<223> OTHER INFORMATION: Synthetic primer complementary to the
      extracellular domain of D-SLAM starting at A23; includes a NdeI
      restriction site.

<400> SEQUENCE: 20
gcagcacata tggcccaagt gctgagcaaa gtcg                                34

<210> SEQ ID NO 21
<211> LENGTH: 51
<212> TYPE: DNA
<213> ORGANISM: Artificial sequence
<220> FEATURE:
<221> NAME/KEY: Primer_Bind
<223> OTHER INFORMATION: Synthetic primer complementary to the
      extracellular domain of D-SLAM ending at D233; includes an Asp718
      restriction site.

<400> SEQUENCE: 21
gcagcaggta ccttactaat ctttgtagga ggccttccct ggtgctgcct c             51

<210> SEQ ID NO 22
<211> LENGTH: 51
<212> TYPE: DNA
<213> ORGANISM: Artificial sequence
<220> FEATURE:
<221> NAME/KEY: Primer_Bind
<223> OTHER INFORMATION: Synthetic primer complementary to the full
      length D-SLAM; includes a BamHI restriction site.

<400> SEQUENCE: 22
gcagcaggat ccgccatcat ggtcatgagg ccctgtgga gtctgcttct c              51

<210> SEQ ID NO 23
<211> LENGTH: 46
<212> TYPE: DNA
<213> ORGANISM: Artificial sequence
<220> FEATURE:
<221> NAME/KEY: Primer_Bind
<223> OTHER INFORMATION: Synthetic primer complementary to the full
      length D-SLAM; includes a XbaI restriction site.

<400> SEQUENCE: 23
gcagcatcta gattatggca gatcctgcac aaggggttc tctgtc                    46

<210> SEQ ID NO 24
<211> LENGTH: 45
<212> TYPE: DNA
<213> ORGANISM: Artificial sequence
<220> FEATURE:
<221> NAME/KEY: Primer_Bind
<223> OTHER INFORMATION: Synthetic primer complementary to the
      extracellular domain of D-SLAM; ending at K232; includes a XbaI
      restriction site.

<400> SEQUENCE: 24
gcagcatcta gattatttgt aggaggcctt ccctggtgct gcctc                    45
```

<210> SEQ ID NO 25
<211> LENGTH: 45
<212> TYPE: DNA
<213> ORGANISM: Artificial sequence
<220> FEATURE:
<221> NAME/KEY: Primer_Bind
<223> OTHER INFORMATION: Synthetic primer complementary to the
      extracellular domain of D-SLAM; ending at D233; includes a XbaI
      restriction site.

<400> SEQUENCE: 25
gcagcatcta gaatctttgt aggaggcctt ccctggtgct gcctc            45

<210> SEQ ID NO 26
<211> LENGTH: 68
<212> TYPE: DNA
<213> ORGANISM: Artificial sequence
<220> FEATURE:
<221> NAME/KEY: Primer_Bind
<223> OTHER INFORMATION: Synthetic primer complementary to the
      extracellular domain of D-SLAM; ending at D233 for fusion to
      FLAG; includes a XbaI restriction site.

<400> SEQUENCE: 26
gcagcatcta gattacttgt catcgtcgtc cttgtagtca tctttgtagg aggccttccc    60
tggtgctg                                                              68

<210> SEQ ID NO 27
<211> LENGTH: 31
<212> TYPE: DNA
<213> ORGANISM: Artificial sequence
<220> FEATURE:
<221> NAME/KEY: Primer_Bind
<223> OTHER INFORMATION: Synthetic primer complementary to the murine
      D-SLAM locus; includes an Asp718 restriction site

<400> SEQUENCE: 27
agccggtacc tccgatgtgc ataatcaggc t                            31

<210> SEQ ID NO 28
<211> LENGTH: 33
<212> TYPE: DNA
<213> ORGANISM: Artificial sequence
<220> FEATURE:
<221> NAME/KEY: Primer_Bind
<223> OTHER INFORMATION: Synthetic primer complementary to the murine
      D-SLAM locus; includes an Asp718 restriction site

<400> SEQUENCE: 28
gcttggcgcg ccccctggtta gtctgcctat gta                         33

<210> SEQ ID NO 29
<211> LENGTH: 31
<212> TYPE: DNA
<213> ORGANISM: Artificial sequence
<220> FEATURE:
<221> NAME/KEY: Primer_Bind
<223> OTHER INFORMATION: Synthetic primer complementary to the murine
      D-SLAM locus; includes an Asp718 restiction site

<400> SEQUENCE: 29
atccatcgat ccaccaagat tcacaggctt g                            31

<210> SEQ ID NO 30
<211> LENGTH: 37
<212> TYPE: DNA
<213> ORGANISM: Artificial sequence

```
-continued

<220> FEATURE:
<221> NAME/KEY: Primer_Bind
<223> OTHER INFORMATION: Synthetic primer complementary to the murine
      D-SLAM locus; includes an Asp718 restiction site

<400> SEQUENCE: 30
ataagaatgc ggccgcaagg gctatgcaag cttggct                                37
```

What is claimed is:

1. An isolated antibody or fragment thereof that specifically binds to a protein selected from the group consisting of:
   (a) a protein consisting of amino acid residues 1 to 285 of SEQ ID NO:2;
   (b) a protein consisting of amino acid residues 23 to 285 of SEQ ID NO:2;
   (c) a protein consisting of amino acid residues 23 to 232 of SEQ ID NO:2;
   (d) a protein consisting of a portion of SEQ ID NO:2, wherein said portion is at least 30 contiguous amino acid residues of SEQ ID NO:2 in length; and
   (e) a protein consisting of a portion of SEQ ID NO:2, wherein said portion is at least 50 contiguous amino acid residues of SEQ ID NO:2 in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 1 that specifically binds protein (e).

7. The antibody or fragment thereof of claim 2 that specifically binds protein (b).

8. The antibody or fragment thereof of claim 4 wherein said protein bound by said antibody or fragment thereof is glycosylated.

9. The antibody or fragment thereof of claim 4 which is a human antibody.

10. The antibody or fragment thereof of claim 4 which is a polyclonal antibody.

11. The antibody or fragment thereof of claim 4 which is selected from the group consisting of:
    (a) a chimeric antibody;
    (b) a humanized antibody;
    (c) a single chain antibody; and
    (d) a Fab fragment.

12. The antibody or fragment thereof of claim 4 which is coupled or conjugated to a detectable substance.

13. The antibody of fragment thereof of claim 12 wherein the detectable substance is selected from the group consisting of:
    (a) an enzyme;
    (b) a fluorescent label;
    (c) a luminescent label;
    (d) a bioluminescent label;
    (e) a radioactive label; and
    (f) a prosthetic label.

14. The antibody or fragment thereof of claim 4 wherein said antibody or fragment thereof specifically binds to said protein in a Western blot.

15. The antibody or fragment thereof of claim 4 wherein said antibody or fragment thereof specifically binds to said protein in an ELISA.

16. An isolated cell that produces the antibody or fragment thereof of claim 4.

17. A hybridoma that produces the antibody or fragment thereof of claim 4.

18. A method of detecting a protein in a biological sample comprising:
    (a) contacting the biological sample with the antibody or fragment thereof of claim 4; and
    (b) detecting the protein in the biological sample.

19. The method of claim 18 wherein the antibody or fragment thereof is a polyclonal antibody.

20. An isolated antibody or fragment thereof obtained from an animal that has been immunized with a protein selected from the group consisting of:
    (a) a protein consisting of amino acid residues 1 to 285 of SEQ ID NO:2;
    (b) a protein consisting of amino acid residues 23 to 285 of SEQ ID NO:2;
    (c) a protein consisting of amino acid residues 23 to 232 of SEQ ID NO:2;
    (d) a protein consisting of a portion of SEQ ID NO:2, wherein said portion is at least 30 contiguous amino acid residues of SEQ ID NO:2 in length; and
    (e) a protein consisting of a portion of SEQ ID NO:2, wherein said portion is at least 50 contiguous amino acid residues of SEQ ID NO:2 in length;
    wherein said antibody or fragment thereof specifically binds to said amino acid sequence.

21. The antibody or fragment thereof of claim 20 obtained from an animal immunized with protein (a).

22. The antibody or fragment thereof of claim 20 obtained from an animal immunized with protein (b).

23. The antibody or fragment thereof of claim 20 obtained from an animal immunized with protein (c).

24. The antibody or fragment thereof of claim 20 obtained from an animal immunized with protein (d).

25. The antibody or fragment thereof of claim 20 obtained from an animal immunized with protein (e).

26. The antibody or fragment thereof of claim 20 which is a monoclonal antibody.

27. The antibody or fragment thereof of claim 20 which is selected from the group consisting of:
    (a) a chimeric antibody;
    (b) a polyclonal antibody;
    (c) a humanized antibody;
    (d) a single chain antibody; and
    (e) a Fab fragment.

28. An isolated monoclonal antibody or fragment thereof that specifically binds to a protein selected from the group consisting of:
- (a) a protein consisting of amino acid residues 1 to 285 of SEQ ID NO:2;
- (b) a protein consisting of amino acid residues 23 to 285 of SEQ ID NO:2;
- (c) a protein consisting of amino acid residues 23 to 232 of SEQ ID NO:2;
- (d) a protein consisting of a portion of SEQ ID NO:2, wherein said portion is at least 30 contiguous amino acid residues of SEQ ID NO:2 in length; and
- (e) a protein consisting of a portion of SEQ ID NO:2, wherein said portion is at least 50 contiguous amino acid residues of SEQ ID NO:2 in length.

29. The antibody or fragment thereof of claim 28 that specifically binds protein (a).

30. The antibody or fragment thereof of claim 28 that specifically binds protein (b).

31. The antibody or fragment thereof of claim 28 that specifically binds protein (c).

32. The antibody or fragment thereof of claim 28 that specifically binds protein (d).

33. The antibody or fragment thereof of claim 28 that specifically binds protein (e).

34. The antibody or fragment thereof of claim 29 that specifically binds protein (b).

35. The antibody or fragment thereof of claim 31 wherein said protein bound by said antibody or fragment thereof is glycosylated.

36. The antibody or fragment thereof of claim 31 which is a human antibody.

37. The antibody or fragment thereof of claim 31 which is selected from the group consisting of:
- (a) a chimeric antibody;
- (b) a humanized antibody;
- (c) a single chain antibody; and
- (d) a Fab fragment.

38. The antibody or fragment thereof of claim 31 which is coupled or conjugated to a detectable substance.

39. The antibody or fragment thereof of claim 38 wherein the detectable substance is selected from the group consisting of:
- (a) an enzyme;
- (b) a fluorescent label;
- (c) a luminescent label;
- (d) a bioluminescent label;
- (e) a radioactive label; and
- (f) a prosthetic label.

40. The antibody or fragment thereof of claim 31 wherein said antibody or fragment thereof specifically binds to said protein in a Western blot.

41. The antibody or fragment thereof of claim 31 wherein said antibody or fragment thereof specifically binds to said protein in an ELISA.

42. An isolated cell that produces the antibody or fragment thereof of claim 31.

43. A hybridoma that produces the antibody or fragment thereof of claim 31.

44. A method of detecting a protein in a biological samples comprising:
- (a) contacting the biological sample with the antibody or fragment thereof of claim 31; and
- (b) detecting the protein in the biological sample.

45. An isolated antibody or fragment thereof that specifically binds to a protein selected from the group consisting of:
- (a) a protein consisting of the full-length polypeptide encoded by the cDNA contained in ATCC Deposit Number 209623;
- (b) a protein consisting of a portion of the polypeptide encoded by the cDNA contained in ATCC Deposit Number 209623, wherein said portion is at least 30 contiguous amino acid residues in length of the polypeptide encoded by the cDNA contained in ATCC Deposit Number 209623; and
- (c) a protein consisting of a portion of the polypeptide encoded by the cDNA contained in ATCC Deposit Number 209623, wherein said portion is at least 50 contiguous amino acid residues in length of the polypeptide encoded by the cDNA contained in ATCC Deposit Number 209623.

46. The antibody or fragment thereof of claim 45 that specifically binds protein (a).

47. The antibody or fragment thereof of claim 45 that specifically binds protein (b).

48. The antibody or fragment thereof of claim 45 that specifically binds protein (c).

49. The antibody or fragment thereof of claim 45 wherein said protein bound by said antibody or fragment thereof is glycosylated.

50. The antibody or fragment thereof of claim 45 which is a human antibody.

51. The antibody or fragment thereof of claim 45 which is a polyclonal antibody.

52. The antibody or fragment thereof of claim 45 which is selected from the group consisting of:
- (a) a chimeric antibody;
- (b) a humanized antibody;
- (c) a single chain antibody; and
- (d) a Fab fragment.

53. The antibody or fragment thereof of claim 45 which is coupled or conjugated to a detectable substance.

54. The antibody or fragment thereof of claim 53 wherein the detectable substance is selected from the group consisting of:
- (a) an enzyme;
- (b) a fluorescent label;
- (c) a luminescent label;
- (d) a bioluminescent label;
- (e) a radioactive label; and
- (f) a prosthetic label.

55. The antibody or fragment thereof of claim 45 wherein said antibody or fragment thereof specifically binds to said protein in a Western blot.

56. The antibody or fragment thereof of claim 45 wherein said antibody or fragment thereof specifically binds to said protein in an ELISA.

57. An isolated cell that produces the antibody or fragment thereof of claim 45.

58. A hybridoma that produces the antibody or fragment thereof of claim 45.

59. A method of detecting a protein in a biological sample comprising:
- (a) contacting the biological sample with the antibody or fragment thereof of claim 45; and
- (b) detecting the protein in the biological sample.

60. The method of claim 59 wherein the antibody or fragment thereof is a polyclonal antibody.

61. An isolated antibody or fragment thereof obtained from an animal that has been immunized with a protein selected from the group consisting of:

(a) a protein consisting of the full-length polypeptide encoded by the cDNA contained in ATCC Deposit Number 209623;

(b) a protein consisting of a portion of the polypeptide encoded by the cDNA contained in ATCC Deposit Number 209623, wherein said portion is at least 30 contiguous amino acid residues in length of the polypeptide encoded by the cDNA contained in ATCC Deposit Number 209623; and (c) a protein consisting of a portion of the polypeptide encoded by the cDNA contained in ATCC Deposit Number 209623, wherein said portion is at least 50 contiguous amino acid residues in length of the polypeptide encoded by the cDNA contained in ATCC Deposit Number 209623;

wherein said antibody or fragment thereof specifically binds to said amino acid sequence.

62. The antibody or fragment thereof of claim 61 obtained from an animal immunized with protein (a).

63. The antibody or fragment thereof of claim 61 obtained from an animal immunized with protein (b).

64. The antibody or fragment thereof of claim 61 obtained from an animal immunized with protein (c).

65. The antibody or fragment thereof of claim 61 which is a monoclonal antibody.

66. The antibody or fragment thereof of claim 61 which is selected from the group consisting of:

(a) a chimeric antibody;

(b) a polyclonal antibody;

(c) a humanized antibody;

(d) a single chain antibody; and (e) a Fab fragment.

67. An isolated monoclonal antibody or fragment thereof that specifically binds to a protein selected from the group consisting of:

(a) a protein consisting of the full-length polypeptide encoded by the cDNA contained in ATCC Deposit Number 209623;

(b) a protein consisting of a portion of the polypeptide encoded by the cDNA contained in ATCC Deposit Number 209623, wherein said portion is at least 30 contiguous amino acid residues in length of the polypeptide encoded by the cDNA contained in ATCC Deposit Number 209623; and (c) a protein consisting of a portion of the polypeptide encoded by the cDNA contained in ATCC Deposit Number 209623, wherein said portion is at least 50 contiguous amino acid residues in length of the polypeptide encoded by the cDNA contained in ATCC Deposit Number 209623.

68. The antibody or fragment thereof of claim 67 that specifically binds protein (a).

69. The antibody or fragment thereof of claim 67 that specifically binds protein (b).

70. The antibody or fragment thereof of claim 67 that specifically binds protein (c).

71. The antibody or fragment thereof of claim 67 wherein said protein bound by said antibody or fragment thereof is glycosylated.

72. The antibody or fragment thereof of claim 67 which is a human antibody.

73. The antibody or fragment thereof of claim 67 which is selected from the group consisting of:

(a) a chimeric antibody;

(b) a humanized antibody;

(c) a single chain antibody; and (d) a Fab fragment.

74. The antibody or fragment thereof of claim 67 which is coupled or conjugated to a detectable substance.

75. The antibody or fragment thereof of claim 74 wherein the detectable substance is selected from the group consisting of:

(a) an enzyme;

(b) a fluorescent label;

(c) a luminescent label;

(d) a bioluminescent label;

(e) a radioactive label; and (f) a prosthetic label.

76. The antibody or fragment thereof of claim 67 wherein said antibody or fragment thereof specifically binds to said protein in a Western blot.

77. The antibody or fragment thereof of claim 67 wherein said antibody or fragment thereof specifically binds to said protein in an ELISA.

78. An isolated cell that produces the antibody or fragment thereof of claim 67.

79. A hybridoma that produces the antibody or fragment thereof of claim 67.

80. A method of detecting a protein in a biological sample comprising:

(a) contacting the biological sample with the antibody or fragment thereof of claim 67; and (b) detecting the protein in the biological sample.

81. An isolated antibody or fragment thereof that specifically binds Dendritic Enriched Secreted Lymphocyte Activation Molecule protein purified from a cell culture wherein the cells in said cell culture comprise a polynucleotide encoding amino acids 23 to 232 of SEQ ID NO:2 operably associated with a regulatory sequence that controls the expression of said polynucleotide.

82. The antibody or fragment thereof of claim 81 which is a monoclonal antibody.

83. The antibody or fragment thereof of claim 81 which is a human antibody.

84. The antibody or fragment thereof of claim 81 which is selected from the group consisting of:

(a) a chimeric antibody;

(b) a polyclonal antibody;

(c) a humanized antibody;

(d) a single chain antibody; and (e) a Fab fragment.

85. The antibody or fragment thereof of claim 81 wherein said antibody or fragment thereof binds to said protein in a Western blot.

86. The antibody or fragment thereof of claim 81 wherein said antibody or fragment thereof binds to said protein in an ELISA.

87. An isolated antibody or fragment thereof that binds a protein comprising amino acid residues 23 to 232 of SEQ ID NO:2 with a dissociation constant (KD) less than or equal to $10^{-8}$ M.

88. The isolated antibody or fragment thereof of claim 87, wherein the isolated antibody or fragment has a dissociation constant (KD) less than or equal to $10^{-9}$ M.

89. The isolated antibody or fragment thereof of claim 87, wherein the isolated antibody or fragment has a dissociation constant (KD) less than or equal to $10^{-10}$ M.

90. The isolated antibody or fragment thereof of claim 87, wherein the isolated antibody or fragment has a dissociation constant (KD) less than or equal to $10^{-11}$ M.

91. The isolated antibody or fragment thereof of claim 87, wherein the isolated antibody or fragment has a dissociation constant (KD) less than or equal to $10^{-12}$ M.

92. The antibody or fragment thereof of claim 87, wherein said protein bound by said antibody or fragment thereof is glycosylated.

93. The antibody or fragment thereof of claim 87 which is a human antibody.

* * * * *

UNITED STATES PATENT AND TRADEMARK OFFICE
CERTIFICATE OF CORRECTION

PATENT NO. : 7,012,134 B2 Page 1 of 1
APPLICATION NO. : 10/062523
DATED : March 14, 2006
INVENTOR(S) : Steven M. Ruben et al.

It is certified that error appears in the above-identified patent and that said Letters Patent is hereby corrected as shown below:

On the Title page,

[*] Notice:  Subject to any disclaimer, the term of this patent is extended or adjusted under 35 USC 154(b) by (459) days Delete the phrase "by 459 days" and insert -- by 579 days--

Signed and Sealed this

Second Day of October, 2007

JON W. DUDAS
*Director of the United States Patent and Trademark Office*